United States Patent
Hart et al.

(10) Patent No.: US 7,704,996 B2
(45) Date of Patent: Apr. 27, 2010

(54) COMPOUNDS AND COMPOSITIONS USEFUL AS CATHEPSIN S INHIBITORS

(75) Inventors: Terance William Hart, London (GB); Allan Hallett, Horsham (GB); Fumiaki Yokokawa, Ibaraki (JP); Hajime Hirao, Ibaraki (JP); Takeru Ehara, Ibaraki (JP); Atsuko Iwasaki, Ibaraki (JP); Junichi Sakaki, Ibaraki (JP); Keiichi Masuya, Bottmingen (CH); Masashi Kishida, Ibaraki (JP); Osamu Irie, Ibaraki (JP)

(73) Assignee: Novartis AG, Basel (CH)

( * ) Notice: Subject to any disclaimer, the term of this patent is extended or adjusted under 35 U.S.C. 154(b) by 324 days.

(21) Appl. No.: 11/573,451

(22) PCT Filed: Aug. 16, 2005

(86) PCT No.: PCT/EP2005/008896

§ 371 (c)(1),
(2), (4) Date: Feb. 9, 2007

(87) PCT Pub. No.: WO2006/018284

PCT Pub. Date: Feb. 23, 2006

(65) Prior Publication Data

US 2009/0048230 A1    Feb. 19, 2009

(30) Foreign Application Priority Data

Aug. 17, 2004 (GB) .................................. 0418353.9

(51) Int. Cl.
*C07D 239/42* (2006.01)
*A61K 31/506* (2006.01)

(52) U.S. Cl. ................... 514/217.06; 514/235.8; 514/252.14; 514/252.15; 514/256; 540/601; 544/122; 544/295; 544/328; 544/329

(58) Field of Classification Search ........... 544/122, 544/295, 328, 329; 540/601; 514/217.06, 514/235.8, 252.14, 252.15, 256
See application file for complete search history.

(56) References Cited

FOREIGN PATENT DOCUMENTS

WO    2004/000819    12/2003
WO    2004/020441    3/2004

OTHER PUBLICATIONS

Ulrich, Chapter 4: Crystallization, Kirk-Othmer Encyclopedia of Chemical Technology, Aug. 2002.*
Vippagunta et al., Crystalline Solids, Advanced Drug Deliversy Reviews, 48, pp. 3-26, 2001.*
West, Solid Solutions, Solid State Chemistry and its applications, pp. 358 & 365, 1988.*
"Carbamate-Based Reversible Inhibitors of Cathepsin S and Cathepsin K" Expert Opinion on Therapeutic Patents, Ashley Publications, GB, vol. 13, No. 7, pp. 1077-1080, (2003).

* cited by examiner

*Primary Examiner*—Deepak Rao
(74) *Attorney, Agent, or Firm*—Paul D. Strain, Esq.; Fanelli Strain & Haag PLLC

(57) ABSTRACT

The present invention relates to the use of a 2-cyanopyrimidine compound of the formula

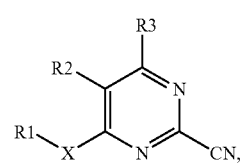

(I)

wherein
$R_1$, $R_2$, $R_3$ and X are as defined in the specification and in the claims, in free form or in salt form, and, where possible, in tautomeric form, as an inhibitor of the activity of cathepsin S.

7 Claims, No Drawings

COMPOUNDS AND COMPOSITIONS USEFUL AS CATHEPSIN S INHIBITORS

This application is a 371 of PCT/EP05/08896 filed Aug. 16, 2005.

The present invention relates to novel 2-cyano-pyrimidine derivatives, their preparation, their use as pharmaceuticals, pharmaceutical compositions containing them, the use of such compounds for the manufacture of a pharmaceutical preparation for the treatment of pain and to a method for the treatment of such a disorder in warm-blooded animals, especially in humans.

Surprisingly, it has been found that the 2-cyano-pyrimidine derivatives described herein have advantageous pharmacological properties and inhibit, for example, the activity of cathepsin S enzymes. The 2-cyano-pyrimidine derivatives of formula I are hence suitable to be used in the treatment of diseases wherein the inhibition of cathepsin S activity causes a beneficial effect.

The 2-cyano-pyrimidine derivatives of formula I are suitable, in particular, for the treatment and in the prevention of neuropathic pain and other diseases mentioned hereinafter.

Hence, the present invention relates to 2-cyano-pyrimidines of formula

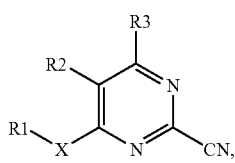
(I)

wherein $R_1$ denotes a radical of formula

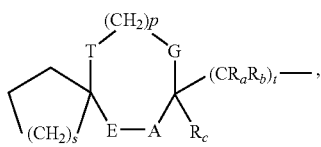
(Ia)

wherein A, E and G independently of each other represent O, S or $CH_2$, under the proviso that at least one of A and E represents $CH_2$;

T is O, S or a bond, if G is $CH_2$, and T is a bond, if G is O or S;

Ra, Rb and Rc independently of each other represent hydrogen or $C_1$-$C_4$alkyl;

s is 0, 1 or 2, t is 1, 2, 3 or 4 and p is 0, 1 or 2;

$R_2$ denotes halogen, $C_1$-$C_4$ alkyl, unsubstituted or substituted aryl, 5 or 6 membered heterocyclyl, —C(O)$NR_4R_5$, —NHC(O)$R_4$ or —$CH_2$NHC(O)$R_4$, wherein $R_4$ represents (a) $C_1$-$C_7$alkyl which is unsubstituted or substituted by halogen; amino, which is mono- or disubstituted by $C_3$-$C_5$Cycloalkyl or $C_1$-$C_6$alkyl which in each case are unsubstituted or mono-, di- or trisubstituted by halogen; unsubstituted or substituted $C_4$-$C_8$-aliphatic heterocyclyl comprising at least one nitrogen atom; unsubstituted or substituted aryl; unsubstituted or substituted hetaryl; unsubstituted or substituted spiro[4.5]decane which comprises 1 or 2 heteroatoms selected from oxygen, nitrogen and sulfur; unsubstituted or substituted $C_3$-$C_6$cycloalkyl; or 1-aza-($C_5$-$C_8$)bicycloalkyl;

(b) unsubstituted or substituted N—($C_1$-$C_4$alkyl)piperidinyl or N—($C_4$-$C_6$cycloalkyl)piperidinyl;

(c) unsubstituted or substituted aryl;

(d) unsubstituted or substituted $C_3$-$C_6$cycloalkyl; or (e) unsubstituted or substituted 5 or 6 membered hetaryl containing one nitrogen atom; and $R_5$ represents hydrogen or $C_1$-$C_4$alkyl; or $R_4$ and $R_5$ together with the nitrogen to which they are attached represent unsubstituted or substituted $C_4$-$C_8$-aliphatic heterocyclyl comprising at least one nitrogen atom; or $R_2$ denotes —$N(R_9)SO_2R_{10}$, $R_9$ represents hydrogen or $C_1$-$C_4$alkyl; and $R_{10}$ represents $C_1$-$C_4$alkyl, which is unsubstituted or substituted by aryl; or $R_9$ and $R_{10}$ together form a radical —$(CRR')_m$—, wherein m is an integer from and including 2 up to and including 5 and R and R' both represent independently of each other hydrogen or $C_1$-$C_4$alkyl;

$R_3$ denotes hydrogen, halogen, phenyl, pyridyl, which is unsubstituted or mono-, di- or trisubstituted by halogen, Y—$R_6$ or $NR_7R_8$ wherein Y represents O, $CH_2$, S, SO, $SO_2$ or $NR_N$, wherein $R_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl-$(CH_2)_q$—, wherein q is an integer from 0 to 4, or five or six-membered aliphatic heterocyclyl-$(CH_2)_n$—, wherein n is an integer from 0 to 4 and the heterocyclyl moiety comprises at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety comprises at least one nitrogen atom;

X denotes O, HN, $C_1$-$C_4$alkyl-N, S, SO, $SO_2$, O($CH_2$)$_g$NH, wherein g is 1 or 2, $(CH_2)_h$, wherein h is 1 or 2, or aryl, which is unsubstituted or mono-, di- or trisubstituted by halogen, $C_1$-$C_4$alkyl or $C_1$-$C_4$alkoxy;

and to salts and tautomers of such 2-cyano-pyrimidines.

The general terms used hereinbefore and hereinafter preferably have within the context of this disclosure the following meanings, unless otherwise indicated:

Where the plural form is used for compounds, salts, and the like, this is taken to mean also a single compound, salt, or the like.

Halogen or halo is especially fluorine, chlorine, bromine, or iodine, especially fluorine, chlorine, or bromine.

Alkyl is especially alkyl with from and including 1 up to and including 7, preferably from and including 1 to and including 4, C atoms and is linear or branched; preferably, alkyl is methyl, ethyl, propyl, such as n-propyl or isopropyl, butyl, such as n-butyl, sec-butyl, isobutyl or tert-butyl.

Alkoxy is especially methoxy, ethoxy or propoxy.

Cycloalkyl is especially $C_3$-$C_6$cycloalkyl, namely cyclopropyl, cyclobutyl, cyclopentyl or cyclohexyl.

Aliphatic heterocyclyl comprising at least one nitrogen atom is especially a five or six-membered heterocyclic radical with one ring nitrogen atom and optionally further 1 or 2 ring heteroatoms selected from the group comprising nitrogen, oxygen, and sulfur, which may be wholly or partly saturated, preferably imidazolidinyl, pyrrolidinyl, piperidinyl, morpholinyl, thiomorpholinyl or piperazinyl, and which radical can be unsubstituted or substituted.

In unsubstituted or substituted aryl, aryl is preferably a mono-, bi- or tricyclic aromatic hydro-carbon group with 6 to 14 ring carbon atoms, especially phenyl, naphthyl or fluorenyl, more preferably phenyl.

Hetaryl as used herein is especially thienyl, pyrrolyl, furyl, oxazolyl, isoxazolyl, isothiazolyl, thiazoyl, pyrazolyl, imidazolyl, benzimidazolyl, benzthiazolyl, pyridinyl, pyrimidinyl, pyrazinyl, more preferably thienyl, furyl, pyridinyl and pyrazolyl.

Unless otherwise mentioned, the term "unsubstituted or substituted" as used herein means that the respective radical is unsubstituted or substituted by one or more, preferably up to four, especially one or two substituents, selected from oxo, amino, $C_1$-$C_4$alkyl amino, di($C_1$-$C_4$alky)-amino, hydroxy-$C_1$-$C_4$alkyl amino, phenyl-$C_1$-$C_4$alkyl amino, $C_3$-$C_5$cycloalkyl amino, di($C_3$-$C_5$)cycloalkyl amino, N—$C_1$-$C_4$alkyl-N—$C_3$-$C_5$cycloalkyl amino, $C_1$-$C_4$alkanoyl amino, halogen, hydroxy, $C_1$-$C_4$alkoxy, unsubstituted or substituted $C_3$-$C_6$cycloalkyl, $C_3$-$C_5$cycloalkyloxy, $C_1$-$C_4$alkoxy $C_1$-$C_4$alkoxy, di($C_1$-$C_4$alkyl)-amino $C_1$-$C_4$alkoxy, carbamoyl, N—$C_1$-$C_4$alkyl-carbamoyl, N,N-di($C_1$-$C_4$alkyl)-carbamoyl, nitro, cyano, carboxy, $C_1$-$C_4$alkoxy carbonyl, $C_1$-$C_4$alkanoyl, $C_1$-$C_4$alkanoyloxy, benzoyl, amidino, guanidino, ureido, mercapto, $C_1$-$C_4$alkylthio, pyridyl, $C_1$-$C_4$alkyl pyridyl, phenyl, unsubstituted or substituted phenyl, phenoxy, $C_1$-$C_4$alkoxy phenyl, phenylthio, phenyl-$C_1$-$C_4$alkylthio, $C_1$-$C_4$alkylsulfonyl, phenylsulfonyl, $C_1$-$C_4$alkylphenylsulfonyl, $C_1$-$C_4$alkenyl, unsubstituted or substituted $C_4$-$C_8$heterocyclyl, e.g. $C_5$-$C_7$oxacyloalkyl or $C_5$-$C_7$dioxacyloalkyl, unsubstituted or substituted $C_4$-$C_8$heterocyclyloxy, e.g. tetrahydropyranyloxy, unsubstituted or substituted $C_4$-$C_8$heterocyclyl $C_1$-$C_4$alkoxy, $C_1$-$C_4$alkylene dioxy bound at adjacent C-atoms of the ring, and $C_1$-$C_4$alkyl, which is unsubstituted or substituted by halogen, hydroxy, $C_1$-$C_4$alkoxy, nitro, imino, cyano, carboxy, $C_1$-$C_4$alkoxy carbonyl, $C_1$-$C_4$alkanoyl, $C_1$-$C_4$alkanoyloxy or unsubstituted or substituted $C_4$-$C_8$heterocyclyl.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Salts are formed, for example, as acid addition salts, preferably with organic or inorganic acids, from compounds of formula I with a basic nitrogen atom, especially the pharmaceutically acceptable salts. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The compounds of formula I exhibit valuable pharmacological properties in mammals and are particularly useful as inhibitors of cathepsin S. The cathepsin S inhibitory effects of the compounds of formula I can be demonstrated in vitro by measuring the inhibition of e.g. recombinant human cathepsin S (in vitro cathepsin S assay).

The in vitro assay is carried out in clear, flat-bottomed, 96-well microtiter plates (Greiner GmbH, Germany) at ambient temperature using recombinant human cathepsin S. Inhibition of human cathepsin S is assayed at a constant enzyme and various substrate concentrations (substrate is Z-Leu-Leu-4-methylcoumaryl-7-amide (Bachem (Switzerland)) in 100 parts 0.2M sodium phosphate, pH 7.0, containing 2 mM EDTA, 2 parts 1% Triton X-100, 10 parts 20 mM dithiothreitol (DTT) and 58 parts distilled water. The assay is started by adding the enzyme solution (13 times higher concentration of final concentration of recombinant human Cathepsin S) to the reaction mixture containing various concentrations of the corresponding substrate and the compound. Substrate concentrations between 3.4 and 17 µM are used. The recombinant human Cathepsin S is used at a final concentration of 0.04 nM. Test compounds are used at concentrations between 0.4 and 2 times the determined IC50 of the compound at the enzyme. The relative fluorescence is continuously measured for 30 minutes and the initial velocity is obtained from each progress curve. The inhibition patterns and the $K_i$ values are determined by Dixon plot analysis.

Compounds of formula I typically have $IC_{50}$s for inhibition of human cathepsin S of less than about 350 nM down to about 1 nM or less, preferably of about 50 nM or less.

In view of their activity as inhibitors of cathepsin S, compounds of formula I are particularly useful in mammals as agents for the treatment and prophylaxis of diseases and medical conditions Involving elevated levels of cathepsin S activity. Such diseases include chronic neuropathic pain, exemplified by conditions such as diabetic neuropathy, postherpetic neuralgia, trigeminal neuralgia, painful diabetic polyneuropathy, post-stroke pain (central pain), postamputation pain, myelopathic or radiculopathic pain (e.g. spinal stenosis, arachnoiditis, root sleeve fibrosis), atypical facial pain and causalgia-like syndromes (complex regional pain syndromes).

Cathepsin S is present in antigen presenting cells and plays a key role in events involved in antigen presentation. In this respect inhibitors of cathepsin S could be useful agents in the prevention, inhibition or treatment of immune and autoimmune disorders, including, but not limited to asthma, rheumatoid arthritis, multiple sclerosis, systemic lupus erythmatosus, psoriasis and Crohn's disease and for the prevention, inhibition or treatment of tissue transplant rejection.

Furthermore cathepsin S can be secreted by some antigen presenting cells and thus play a role in extracellular matrix interactions. Therefore, cathepsin S inhibitors could be useful agents in the prevention, inhibition or treatment of neurodegenerative diseases with a possible inflammatory component, Alzheimer's disease, multiple sclerosis, Parkinson's disease, Huntington's disease, motor neuron disease, amyotrophic lateral sclerosis (ALS), HIV neuropathy, diabetic neuropathies, Guillain-Barré syndrome, CIPD (Chronic inflammatory demyelinating polyradiculoneuropathy), other demyelinating diseases, meningitis, brain/spinal cord trauma, stroke, schizophrenia.

Cathepsin S inhibitors could be useful agents in the prevention, inhibition or treatment of a variety of other diseases involving extra-cellular proteolysis such as the development of emphysema in chronic obstructive pulmonary disease, atherosclerosis, restenosis and tumor cell invasion.

Cathepsin S is present in inflammatory cells and cathepsin S inhibitors could be useful agents compounds for the treatment of Creutzfeldt-Jakob Disease, interstitial cystitis, inflammatory bowel disease and vasculitic disorders.

Beneficial effects are evaluated in in vitro and in vivo pharmacological tests generally known in the art, and as illustrated herein. The above cited properties are demonstrable in in vitro and in vivo tests, using advantageously mammals, e.g. rats, mice, dogs, rabbits, monkeys or isolated organs and tissues, as well as mammalian enzyme preparations, either natural or prepared by e.g. recombinant technology. Compounds of formula I can be applied in vitro in the form of solutions, e.g. preferably aqueous solutions or suspensions, and in vivo either enterally or parenterally, advantageously orally, e.g. as a suspension or in aqueous solution, or as a solid capsule or tablet formulation. The dosage in vitro may range between about $10^{-5}$ molar and $10^{-9}$ molar concentrations. The dosage in vivo may range, depending on the route of administration, between about 0.1 and 100 mg/kg.

The efficacy of the compounds of formula I for the treatment of chronic inflammatory or neuropathic pain can be determined using the following In vivo animal models:

Chronic Inflammatory Pain Model:

The intraplantar injection of zymosan-induced mechanical hyperalgesia may be used as a model of chronic inflammatory pain (Meller et al, Neuropharmacology 33:1471-1478, 1994). In this model, typically a male Sprague-Dawley or Wistar rat (200-250 g) receives an intraplantar injection of 3 mg/100 μl zymosan into one hind paw. A marked inflammation occurs in this hind paw. Drugs are generally administered for evaluation of efficacy, 24 hours after the inflammatory insult, when mechanical hyperalgesia is considered fully established.

Chronic Neuropathic Pain Models:

Two animal models of chronic neuropathic pain may be used that involve some form of peripheral nerve damage. In the Seltzer model (Seltzer et al. (1990) Pain 43: 205-218) rats are anaesthetised and a small incision made mid-way up one thigh (usually the left) to expose the sciatic nerve. The nerve is carefully cleared of surrounding connective tissues at a site near the trochanter just distal to the point at which the posterior biceps semitendinosus nerve branches off the common sciatic nerve. A 7-0 silk suture is inserted into the nerve with a ⅜ curved, reversed-cutting mini-needle, and tightly ligated so that the dorsal ⅓ to ½ of the nerve thickness is held within the ligature. The muscle and skin are closed with sutures and clips and the wound dusted with antibiotic powder. In sham animals the sciatic nerve is exposed but not ligated and the wound closed as in nonsham animals.

In the Chronic Constriction Injury (CCI) model (Bennett, G. J. and Xie, Y. K. Pain (1988) 33: 87-107) rats are anaesthetised and a small incision is made mid-way up one thigh (usually the left) to expose the sciatic nerve. The nerve is cleared of surrounding connective tissue and four ligatures of 4/0 chromic gut are tied loosely around the nerve with approximately 1 mm between each, so that the ligatures just barely constrict the surface of the nerve. The wound is closed with sutures and clips as described above. In sham animals the sciatic nerve is exposed but not ligated and the wound closed as in nonsham animals.

In contrast to the Seltzer and CCI models, the Chung model involves ligation of the spinal nerve. (Kim, S. O. and Chung, J. M. Pain (1992): 50:355-363). In this model, rats are anesthetized and placed into a prone position and an incision is made to the left of the spine at the L4-S2 level. A deep dissection through the paraspinal muscles and separation of the muscles from the spinal processes at the L4-S2 level will reveal part of the sciatic nerve as it branches to form the L4, L5 and L6 spinal nerves. The L6 transverse process is carefully removed with a small rongeur enabling visualisation of these spinal nerves. The L5 spinal nerve is isolated and tightly ligated with 7-0 silk suture. The wound is closed with a single muscle suture (6-0 silk) and one or two skin closure clips and dusted with antibiotic powder. In sham animals the L5 nerve is exposed as before but not ligated and the wound closed as before.

Behavioral Index

In all chronic pain models (inflammatory and neuropathic) mechanical hyperalgesia is assessed by measuring paw withdrawal thresholds of both hindpaws to an increasing pressure stimulus using an Analgesymeter (Ugo-Basile, Milan). Mechanical allodynia is assessed by measuring withdrawal thresholds to non-noxious mechanical stimuli applied with von Frey hairs to the plantar surface of both hindpaws. Thermal hyperalgesia is assessed by measuring withdrawal latencies to a noxious thermal stimulus applied to the underside of each hindpaw. With all models, mechanical hyperalgesia and allodynia and thermal hyperalgesia develop within 1-3 days following surgery and persist for at least 50 days. For the assays described, herein, drugs may be applied before and after surgery to assess their effect on the development of hyperalgesia, particularly approximately 14 days following surgery, to determine their ability to reverse established hyperalgesia.

The percentage reversal of hyperalgesia is calculated as follows:

$$\% \text{ reversal} = \frac{\text{postdose threshold} - \text{predose threshold}}{\text{naive threshold} - \text{predose threshold}} \times 100$$

In the experiments disclosed herein, Wistar rats (male) are employed in the pain models described above. Rats weigh approximately 120-140 grams at the time of surgery. All surgery is performed under enflurane/$O_2$ inhalation anaesthesia. In all cases the wound is closed after the procedure and the animal allowed to recover. In all pain models employed, after a few days in all but the sham operated animals, a marked mechanical and thermal hyperalgesia and allodynia develops in which there is a lowering of pain threshold and an enhanced reflex withdrawal response of the hind-paw to touch, pressure or thermal stimuli. After surgery the animals also exhibit characteristic changes to the affected paw. In the majority of animals the toes of the affected hind paw are held together and the foot turned slightly to one side; in some rats the toes are also curled under. The gait of the ligated rats varies, but limping is uncommon. Some rats are seen to raise the affected hind paw from the cage floor and to demonstrate an unusual rigid extension of the hind limb when held. The rats tend to be very sensitive to touch and may vocalise. Otherwise the general health and condition of the rats is good.

The efficacy of the compounds of the invention for the treatment of osteoarthritis can be determined using models such as or similar to the rabbit partial lateral meniscectomy model, as described previously (Colombo et al. Arth. Rheum. 1993 26, 875-886). The efficacy of the compounds in the model can be quantified using histological scoring methods, as described previously (O'Byrne et al. Inflamm Res 1995, 44, S117-S118).

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. For the treatment of pain, in particular a combination which comprises a cathepsin S inhibitor as disclosed herein and gabapentin, pregabalin, non steroidal anti-inflammatory drugs, COX-2 inhibitors, steroids, tricyclic antidepressants, other anticonvulsants (e.g carbamazepine, lamotrigine, Trileptal) or an opioid is highly suitable.

The term "opioid" as used herein refers to all drugs, both natural and synthetic, with morphine-like actions. An opioid suitable for the present invention is especially selected from the group comprising alfentanil, allylprodine, alphaprodine, anileridine, benzylmorphine, bezitramide, buprenorphine, butorphanol, clonitazene, codeine, cyclorphan, desomorphine, dextromoramide, dezocine, diampromide, dihydrocodeine, dihydromorphine, eptazocine, ethylmorphine, fentanyl, hydrocodone, hydromorphone, hydroxypethidine, levophenacylmorphan, levorphanol, lofentanil, methylmorphine, morphine, necomorphine, normethadone, normorphine, opium, oxycodone, oxymorphone, pholcodine, profadol and sufentanil.

For instance, alfentanil can be administered, e.g., in the form as marketed, e.g. under the trademark Rapifen™; allylprodine can be administered, e.g., in the form as marketed, e.g. under the trademark Alperidine™; anileridine can be administered, e.g., in the form as marketed, e.g. under the trademark Leritine™; benzylmorphine can be administered, e.g., in the form as marketed, e.g. under the trademark Peronine™; bezitramide can be administered, e.g., in the form as marketed, e.g. under the trademark Burgodin™; buprenorphine can be administered, e.g., in the form as marketed, e.g. under the trademark Buprenex™; butorphanol can be administered, e.g., in the form as marketed, e.g. under the trademark Torate™; dextromoramide can be administered, e.g., in the form as marketed, e.g. under the trademark Palfium™; dezocine can be administered, e.g., in the form as marketed, e.g. under the trademark Daigan™; dihydrocodeine can be administered, e.g., in the form as marketed, e.g. under the trademark Novicodin™; dihydromorphine can be administered, e.g., in the form as marketed, e.g. under the trademark Paramorphan™; eptazocine can be administered, e.g., in the form as marketed, e.g. under the trademark Sedapain™; ethylmorphine can be administered, e.g., in the form as marketed, e.g. under the trademark Dionin™; fentanyl can be administered, e.g., in the form as marketed, e.g. under the trademark Fentanest™ or Leptanal™; hydrocodone can be administered, e.g., in the form as marketed, e.g. under the trademark Bekadid™ or Calmodid™; hydromorphone can be administered, e.g., in the form as marketed, e.g. under the trademark Novolaudon™; hydroxypethidine can be administered, e.g., in the form as marketed, e.g. under the trademark Bemidone™; levorphanol can be administered, e.g., in the form as marketed, e.g. under the trademark Dromoran™; normethadone can be administered, e.g., in the form as marketed, e.g. under the trademark Ticarda™; oxycodone can be administered, e.g., in the form as marketed, e.g. under the trademark Dihydrone™ and oxymorphone can be administered, e.g., in the form as marketed, e.g. under the trademark Numorphan™.

In formula I the following significances are preferred independently, collectively or in any combination or sub-combination:

$R_1$ denotes a radical of formula

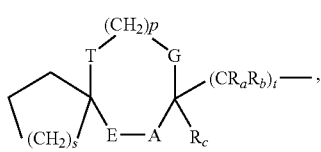

(Ia)

wherein A and G both represent O or both represent $CH_2$, E is $CH_2$ and T is a bond;
Ra, Rb and Rc all represent hydrogen;
s is 0 or 1, t is 1 or 2, more preferably 1, and p is 1;
$R_2$ preferably denotes —C(O)—$NR_4R_5$, —N($R_9$)—$SO_2$—$R_{10}$, bromo, chloro, $C_1$-$C_4$alkyl, in particular isopropyl, unsubstituted phenyl or a 6 membered heterocyclyl group containing at least one oxygen atom;

$R_3$ preferably denotes hydrogen, Y—$R_6$, $NR_7R_8$ or $C_1$-$C_4$alkyl, more preferably Y—$R_6$ or $NR_7R_8$;

$R_4$ preferably represents (a) $C_1$-$C_7$alkyl which is unsubstituted or substituted by amino, which is mono- or disubstituted by $C_3$-$C_5$cycloalkyl or $C_1$-$C_6$alkyl which is unsubstituted or trisubstituted by halogen;

1-aza-($C_4$-$C_8$)cycloalkyl, which is unsubstituted or substituted by $C_1$-$C_4$alkyl;

pyrrolidinyl, which is unsubstituted or substituted by halogen, $C_1$-$C_4$alkoxy, $C_1$-$C_4$alkoxy $C_1$-$C_4$alkyl or $C_1$-$C_4$alkyl amino;

piperidinyl, which is unsubstituted or mono- or disubstituted by halogen, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;

piperazinyl, which is mono- or disubstituted by $C_1$-$C_4$alkyl or phenyl;

phenyl, which is unsubstituted or mono- or disubstituted by halogen, morpholinyl, trifluoromethyl or $C_1$-$C_4$alkoxy;

halogen, $C_3$-$C_5$cycloalkyl, morpholinyl, thienyl, furyl, pyridyl, 2-oxa-6-aza-spiro[4.5]decane or 1-aza-($C_5$-$C_7$)bicycloalkyl;

(b) N—($C_1$-$C_4$alkyl)piperidinyl, which is substituted by phenyl;

(c) phenyl, which is mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl)piperazinyl, N—($C_1$-$C_4$alkyl)piperidinyloxy or N—($C_1$-$C_4$alkyl)piperidinyl $C_1$-$C_4$alkoxy;

(d) $C_3$-$C_5$cycloalkyl;

(e) pyrazolyl, which is mono- or disubstituted by pyridyl or phenyl; or (f) N—($C_1$-$C_4$alkyl)piperidinyl or N—($C_4$-$C_6$cycloalkyl)piperidinyl which in both cases is substituted by phenyl $C_1$-$C_4$alkyl, wherein phenyl is unsubstituted or monosubstituted by halogen;

$R_9$ preferably represents hydrogen or $C_1$-$C_4$alkyl;
$R_{10}$ preferably represents $C_1$-$C_4$alkyl, which is unsubstituted or substituted by phenyl;
X preferably denotes HN, $C_1$-$C_4$alkyl-N or O; and
Y preferably represents O or NH.

In $R_3$, pyridyl is preferably unsubstituted or mono-, di- or trisubstituted by halogen, $C_1$-$C_4$alkyl or piperazinyl.

In $R_4$, $C_1$-$C_7$alkyl preferably is unsubstituted or substituted by amino, which is mono- or disubstituted by $C_3$-$C_5$cycloalkyl or $C_1$-$C_6$alkyl which in each case is unsubstituted or mono-, di- or trisubstituted by halogen; $C_4$-$C_8$-aliphatic heterocyclyl comprising at least one nitrogen atom, which radical is unsubstituted or mono-, di- or trisubstituted by $C_1$-$C_4$alkyl, halogen, $C_1$-$C_4$alkoxy, $C_1$-$C_4$alkoxy $C_1$-$C_4$alkyl, $C_1$-$C_4$alkyl amino, phenyl, pyrrolidinyl, piperidinyl, di(halo)-piperidinyl, morpholinyl, $C_4$-$C_6$cycloalkyl or $C_1$-$C_6$alkyl which is mono-, di- or trisubstituted by hydroxy or halogen; or phenyl, which is unsubstituted or mono-, di- or trisubstituted by halogen, $C_1$-$C_4$alkoxy, $C_1$-$C_4$alkoxy $C_1$-$C_4$alkyl, trifluoromethyl or $C_4$-$C_8$-aliphatic heterocyclyl; hetaryl, which radical is unsubstituted or mono-, di- or trisubstituted by $C_1$-$C_4$alkyl, halogen, $C_1$-$C_4$alkoxy, $C_1$-$C_4$alkoxy $C_1$-$C_4$alkyl, $C_1$-$C_4$alkyl amino, phenyl, pyrrolidinyl, piperidinyl, di(halo)-piperidinyl, morpholinyl, $C_4$-$C_6$cycloalkyl or $C_1$-$C_6$alkyl which is mono-, di- or trisubstituted by hydroxy or halogen; spiro[4.5]decane which comprises 1 or 2 heteroatoms selected from oxygen, nitrogen and sulfur; halogen, $C_3$-$C_6$cycloalkyl or 1-aza-($C_5$-$C_8$)bicycloalkyl;

N—($C_1$-$C_4$alkyl)piperidinyl is preferably substituted by phenyl;

phenyl is preferably mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl)piperazinyl, N—($C_1$-$C_4$alkyl)piperidinyloxy or N—($C_1$-$C_4$alkyl)piperidinyl $C_1$-$C_4$alkoxy;

$C_3$-$C_6$cycloalkyl is preferably unsubstituted;

isoxazolyl, imidazolyl or pyrazolyl is preferably unsubstituted or mono- or disubstituted by pyridyl or phenyl; and N—($C_1$-$C_6$alkyl)piperidinyl or N—($C_4$-$C_6$cycloalkyl)piperidinyl are preferably substituted by phenyl $C_1$-$C_4$alkyl, wherein phenyl is unsubstituted or mono-, di- or trisubstituted by halogen.

If $R_4$ and $R_5$ together with the nitrogen to which they are attached represent pyrrolidinyl or piperidinyl, such radical is preferably unsubstituted or mono-, di- or trisubstituted by hydroxy, $C_1$-$C_4$alkoxy or $C_1$-$C_4$alkyl.

In $R_6$, $C_1$-$C_6$alkyl is preferably unsubstituted or mono-, di- or trisubstituted by pyridyl, $C_1$-$C_4$alkyl pyridyl, imidazolyl, $C_1$-$C_4$alkyl imidazolyl, phenyl, hydroxy phenyl, hydroxy, $C_1$-$C_4$alkoxy, $C_1$-$C_4$alkoxy carbonyl, hydroxy $C_1$-$C_4$alkyl amino, $C_1$-$C_4$alkyl-amino, di-($C_1$-$C_4$alkyl)-amino, $C_1$-$C_4$alkanoyl-amino, phenyl-$C_1$-$C_4$alkyl amino, $C_1$-$C_4$alkylthio, morpholinyl, morpholinyl carbonyl, 2-oxo-imidazolidinyl, 2-oxo-pyrrolidinyl, $C_5$-$C_7$cycloalkyl-amino, $C_3$-$C_5$cycloalkyl, amino-$C_4$-$C_7$cycloalkyl, hydroxy-$C_4$-$C_7$cycloalkyl, tetrahydropyranyl-oxy, N—($C_1$-$C_4$alkyl)piperazinyl, oxa-$C_5$-$C_6$cycloalkyl, dioxa-$C_6$-$C_7$cycloalkyl, or piperidinyl, which is unsubstituted or substituted by halogen, especially fluoro, hydroxy, imino-$C_1$-$C_4$alkyl, $C_1$-$C_4$alkyl, $C_1$-$C_4$alkanoyl, $C_1$-$C_4$alkyl sulfonyl or hydroxy $C_1$-$C_4$alkyl.

In one preferred embodiment, $R_6$ represents (a) $C_1$-$C_4$alkyl, which is unsubstituted or substituted by di-($C_1$-$C_4$alkyl)-amino, N—($C_1$-$C_4$alkyl)piperazinyl or hydroxy, or (b) N-(Q)-piperidinyl-$(CH_2)_n$—, wherein n is an integer from 0 to 4, and Q is hydrogen, $C_1$-$C_4$alkyl or N—($C_1$-$C_4$alkyl)piperidinyl.

Preferably, $R_7$ and $R_8$ together with the nitrogen to which they are attached represent piperidinyl, which is unsubstituted or substituted by $C_1$-$C_4$alkyl, hydroxy, aminocarbonyl, amino $C_1$-$C_4$alkyl, hydroxy $C_1$-$C_4$alkyl, or unsubstituted or substituted by $C_4$-$C_8$ aliphatic heterocyclyl, morpholinyl or thiomorpholinyl which is unsubstituted or substituted by $C_1$-$C_4$alkyl or oxo; piperazinyl, which is unsubstituted or substituted by $C_1$-$C_4$alkyl or $C_1$-$C_4$alkoxy $C_1$-$C_4$alkyl, or pyrrolidinyl, which is unsubstituted or substituted by hydroxy $C_1$-$C_4$alkyl, $C_1$-$C_4$alkoxy $C_1$-$C_4$alkyl, formyl, di-$C_1$-$C_4$alkyl amino, $C_1$-$C_4$alkyl amino, amino, $C_1$-$C_4$alkanoyl amino or aminocarbonyl.

If $R_7$ and $R_8$ together with the nitrogen to which they are attached represent piperidinyl, such radical is preferably substituted by N—($C_1$-$C_4$alkyl)piperazinyl.

In $R_{10}$, $C_1$-$C_4$alkyl is preferably unsubstituted or substituted by phenyl.

In X, phenyl is preferably unsubstituted or mono-, di- or trisubstituted by halogen, $C_1$-$C_4$alkyl or $C_1$-$C_4$alkoxy.

The invention relates in particular to 2-cyano-pyrimidines of formula I wherein
$R_1$ denotes a radical of formula

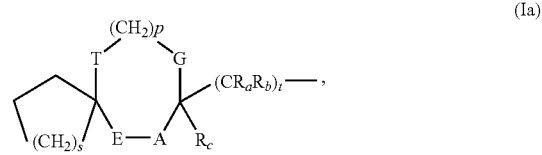

(Ia)

wherein A, E and G independently of each other represent O, S or $CH_2$, under the proviso that at least one of A and E represents $CH_2$;

T is O, S or a bond, if G is $CH_2$, and T is a bond, if G is O or S;

Ra, Rb and Rc independently of each other represent hydrogen or $C_1$-$C_4$alkyl;

s is 0 or 1, t is 1, 2, 3 or 4 and p is 0, 1 or 2;

$R_2$ denotes halogen, $C_1$-$C_4$ alkyl, unsubstituted or substituted phenyl, 5 or 6 membered heterocyclyl, —C(O)$NR_4R_5$, —NHC(O)$R_4$, —$CH_2$NHC(O)$R_4$ or —N($R_9$)$SO_2R_{10}$, wherein $R_4$ represents
  (a) $C_1$-$C_7$alkyl which is unsubstituted or substituted by amino, which is mono- or disubstituted by $C_3$-$C_5$cycloalkyl or $C_1$-$C_6$alkyl which is unsubstituted or trisubstituted by halogen;
    aza-($C_4$-$C_8$)cycloalkyl, which is unsubstituted or substituted by halogen, $C_1$-$C_4$alkoxy, $C_1$-$C_4$alkoxy $C_1$-$C_4$alkyl, $C_1$-$C_4$alkyl amino, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;
    piperazinyl, which is mono- or disubstituted by $C_1$-$C_4$alkyl or phenyl; or
    phenyl, which is unsubstituted or mono- or disubstituted by halogen, morpholinyl, trifluoromethyl or $C_1$-$C_4$alkoxy;
    halogen, $C_3$-$C_5$cycloalkyl, morpholinyl, thienyl, furyl, pyridyl, 2-oxa-6-aza-spiro[4.5]decane or 1-aza-($C_5$-$C_7$)bicycloalkyl;
  (b) N—($C_1$-$C_4$alkyl)piperidinyl, which is substituted by phenyl;
  (c) phenyl, which is mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl)piperazinyl, N—($C_1$-$C_4$alkyl)piperidinyloxy or N—($C_1$-$C_4$alkyl) piperidinyl $C_1$-$C_4$alkoxy;
  (d) $C_3$-$C_5$cycloalkyl;
  (e) isoxazolyl, imidazolyl or pyrazolyl, which in each case is mono- or disubstituted by pyridyl or phenyl; or
  (f) N—($C_1$-$C_6$alkyl)piperidinyl or N—($C_4$-$C_6$cycloalkyl)piperidinyl which in both cases is substituted by phenyl $C_1$-$C_4$alkyl, wherein phenyl is unsubstituted or mono-substituted by halogen; and $R_5$ represents hydrogen or $C_1$-$C_4$alkyl; or $R_4$ and $R_5$ together with the nitrogen to which they are attached represent pyrrolidinyl or piperidinyl which is unsubstituted or substituted by hydroxy;

$R_9$ represents hydrogen or $C_1$-$C_4$alkyl; and $R_{10}$ represents $C_1$-$C_4$alkyl, which is unsubstituted or substituted by phenyl; or $R_9$ and $R_{10}$ together form a radical —(CRR')$_m$—, wherein m is an integer from and including 2 up to and including 4 and R and R' both represent hydrogen;

$R_3$ denotes hydrogen, halogen, phenyl, pyridyl, which is unsubstituted or monosubstituted by halogen or piperazinyl, Y—$R_6$ or $NR_7R_8$ wherein Y represents O, CH$_2$, S, SO, SO$_2$ or NR$_N$, wherein R$_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl-(CH$_2$)$_q$—, wherein q is an integer from 0 to 4, or five or six-membered aliphatic heterocyclyl-(CH$_2$)$_n$—, wherein n is an integer from 0 to 4 and the heterocyclyl moiety comprises at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety comprises at least one nitrogen atom;

X denotes O, HN, $C_1$-$C_4$alkyl-N, S, SO, SO$_2$, OCH$_2$CH$_2$NH, CH$_2$ or phenyl, which is unsubstituted or monosubustituted by halogen;

or to salts of such 2-cyano-pyrimidines.

In particular compounds of formula I are preferred, wherein $R_1$ denotes a radical of formula

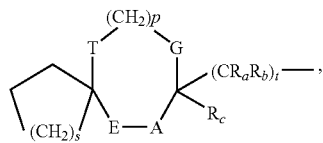

(Ia)

wherein A, E and G independently of each other represent O, S or CH$_2$, under the proviso that at least one of A and E represents CH$_2$;

T is O, S or a bond, if G is CH$_2$, and T is a bond, if G is O or S;

Ra, Rb and Rc independently of each other represent hydrogen or $C_1$-$C_4$alkyl;

s is 0 or 1, t is 1, 2, 3 or 4 and p is 0, 1 or 2;

$R_2$ denotes bromo, chloro, $C_1$-$C_4$ alkyl, unsubstituted phenyl or a 6 membered heterocyclyl group containing at least one oxygen atom, —C(O)—NR$_4$R$_5$ or —N(R$_9$)—SO$_2$—R$_{10}$, wherein $R_4$ represents (a) $C_1$-$C_7$alkyl which is unsubstituted or substituted by amino, which is mono- or disubstituted by $C_3$-$C_5$cycloalkyl or $C_1$-$C_6$alkyl which is unsubstituted or trisubstituted by halogen;

aza-($C_4$-$C_8$)cycloalkyl, which is unsubstituted or substituted by halogen, $C_1$-$C_4$alkoxy, $C_1$-$C_4$alkoxy $C_1$-$C_4$alkyl, $C_1$-$C_4$alkyl amino, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;

piperazinyl, which is mono- or disubstituted by $C_1$-$C_4$alkyl or phenyl; or phenyl, which is unsubstituted or mono- or disubstituted by halogen, morpholinyl, trifluoromethyl or $C_1$-$C_4$alkoxy;

halogen, $C_3$-$C_5$cycloalkyl, morpholinyl, thienyl, furyl, pyridyl, 2-oxa-6-aza-spiro[4.5]decane or 1-aza-($C_5$-$C_7$)bicycloalkyl;

(b) N—($C_1$-$C_4$alkyl)piperidinyl, which is substituted by phenyl;

(c) phenyl, which is mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl)piperazinyl, N—($C_1$-$C_4$alkyl)piperidinyloxy or N—($C_1$-$C_4$alkyl) piperidinyl $C_1$-$C_4$alkoxy;

(d) $C_3$-$C_5$cycloalkyl;

(e) pyrazolyl, which is mono- or disubstituted by pyridyl or phenyl; or (f) N—($C_1$-$C_6$alkyl)piperidinyl or N—($C_4$-$C_6$cycloalkyl)piperidinyl which in both cases is substituted by phenyl $C_1$-$C_4$alkyl, wherein phenyl is unsubstituted or mono-substituted by halogen; and $R_5$ represents hydrogen or $C_1$-$C_4$alkyl; or $R_4$ and $R_5$ together with the nitrogen to which they are attached represent pyrrolidinyl;

$R_9$ represents hydrogen or $C_1$-$C_4$alkyl; and $R_{10}$ represents $C_1$-$C_4$alkyl, which is unsubstituted or substituted by phenyl; or $R_9$ and $R_{10}$ together form a radical —(CRR')$_m$—, wherein m is an integer from and including 2 up to and including 4 and R and R' both represent hydrogen;

$R_3$ denotes hydrogen, Y—$R_6$ or $NR_7R_8$ wherein

Y represents O or NR$_N$, wherein R$_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl-(CH$_2$)$_q$—, wherein q is an integer from 0 to 4, or five or six-membered aliphatic heterocyclyl-(CH$_2$)$_n$—, wherein n is an integer from 0 to 4 and the heterocyclyl moiety comprises at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety comprises at least one nitrogen atom;

X denotes HN, $C_1$-$C_4$alkyl-N or O;

and the corresponding salts of such 2-cyano-pyrimidine.

More preferred are 2-cyano-pyrimidines of formula I, wherein $R_1$ denotes a radical of formula

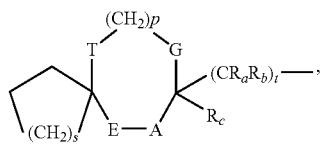

wherein A, E and G independently of each other represent O or CH$_2$, under the proviso that at least one of A and E represents CH$_2$;

T is O or a bond, if G is CH$_2$, and T is a bond, if G is O;

Ra, Rb and Rc all represent hydrogen;

s is 0 or 1, t is 1 or 2 and p is 1;

$R_2$ denotes bromo, chloro, isopropyl, unsubstituted phenyl or a 6 membered heterocyclyl group containing two oxygen atoms, —C(O)—NR$_4$R$_5$ or —N(R$_9$)—SO$_2$—R$_{10}$, wherein $R_4$ represents (a) $C_1$-$C_7$alkyl which is unsubstituted or substituted by amino, which is mono- or disubstituted by $C_3$-$C_5$cycloalkyl or $C_1$-$C_6$alkyl which is unsubstituted or trisubstituted by halogen;

1-aza-($C_7$-$C_8$)cycloalkyl, which is unsubstituted or substituted by $C_1$-$C_4$alkyl;

1-aza-($C_4$)cycloalkyl, which is unsubstituted or substituted by $C_1$-$C_4$alkyl;

pyrrolidinyl, which is unsubstituted or substituted by halogen, $C_1$-$C_4$alkoxy, $C_1$-$C_4$alkoxy $C_1$-$C_4$alkyl or $C_1$-$C_4$alkyl amino;

piperidinyl, which is unsubstituted or mono- or disubstituted by halogen, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;

piperazinyl, which is mono- or disubstituted by $C_1$-$C_4$alkyl or phenyl; or phenyl, which is unsubstituted or mono- or disubstituted by halogen, morpholinyl, trifluoromethyl or $C_1$-$C_4$alkoxy;

halogen, $C_3$-$C_5$cycloalkyl, morpholinyl, thienyl, furyl, pyridyl, 2-oxa-6-aza-spiro[4.5]decane or 1-aza-($C_5$-$C_7$)bicycloalkyl;

(b) N—($C_1$-$C_4$alkyl)piperidinyl, which is substituted by phenyl;

(c) phenyl, which is mono-, di- or trisubstituted by phenyl, $C_3$-$C_6$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl)piperazinyl, N—($C_1$-$C_4$alkyl)piperidinyloxy or N—($C_1$-$C_4$alkyl)piperidinyl $C_1$-$C_4$alkoxy;

(d) $C_3$-$C_5$cycloalkyl;

(e) pyrazolyl, which is mono- or disubstituted by pyridyl or phenyl; or (f) N—($C_1$-$C_6$alkyl)piperidinyl or N—($C_4$-$C_6$cycloalkyl)piperidinyl which in both cases is substituted by phenyl $C_1$-$C_4$alkyl, wherein phenyl is unsubstituted or mono-substituted by halogen; and $R_5$ represents hydrogen or $C_1$-$C_4$alkyl; or $R_4$ and $R_5$ together with the nitrogen to which they are attached represent pyrrolidinyl;

$R_9$ represents hydrogen or $C_1$-$C_4$alkyl; and $R_{10}$ represents $C_1$-$C_4$alkyl, which is unsubstituted or substituted by phenyl; or $R_9$ and $R_{10}$ together form a radical —(CRR')$_m$—, wherein m is an integer from and including 2 up to and including 4 and R and R' both represent hydrogen;

$R_3$ denotes hydrogen, Y—$R_6$ or NR$_7$R$_8$ wherein

Y represents O or NR$_N$, wherein R$_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl-(CH$_2$)$_q$—, wherein q is an integer from 0 to 4, or five or six-membered aliphatic heterocyclyl-(CH$_2$)$_n$—, wherein n is an integer from 0 to 4 and the heterocyclyl moiety comprises at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety comprises at least one nitrogen atom;

X denotes HN, $C_1$-$C_4$alkyl-N or O;

or the salts of such 2-cyano-pyrimidines.

Particularly preferred compounds of the invention are the compounds of the Examples.

Accordingly, in further aspects the invention provides:

2-cyano-pyrimidines of formula I or tautomers thereof, or a pharmaceutically acceptable salt of such a compound, for use in a method for the treatment of the human or animal body;

the use of a 2-cyano-pyrimidine of formula I or a tautomer thereof, or a pharmaceutically acceptable salt of such a compound, for the preparation of a pharmaceutical product for the treatment of neuropathic pain or another disease mentioned herein;

a method for the treatment of neuropathic pain or another disease mentioned herein, which comprises administering a 2-cyano-pyrimidine of formula I or a tautomer thereof, or a pharmaceutically acceptable salt thereof, in a quantity effective against such disease, to a warm-blooded animal requiring such treatment;

a pharmaceutical preparation, comprising a 2-cyano-pyrimidine of formula I or a tautomer thereof, or a pharmaceutically acceptable salt of such a compound, or a hydrate or solvate thereof, and at least one pharmaceutically acceptable carrier;

a method of using compounds of formula I and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g. chronic inflammatory or neuropathic pain; and a method of selectively inhibiting cathepsin S activity in a mammal which comprises administering to a mammal in need thereof an effective cathepsin S inhibiting amount of a compound of formula I, more specifically this relates to a method of treating chronic inflammatory or neuropathic pain (or another disease mentioned herein) in mammals comprises administering to a mammal in need thereof a correspondingly effective amount of a compound of formula I.

A compound of formula I may be prepared by processes that, though not applied hitherto for the new compounds of the present invention, are known per se, especially a process characterized in that a) for the synthesis of a compound of the formula I wherein $R_2$ represents —C(O)NR$_4$R$_5$, $R_3$ denotes hydrogen, halogen, phenyl, pyridyl, which is unsubstituted or mono-, di- or trisubstituted by halogen, Y—$R_6$, wherein Y represents O, NH or S, or NR$_7$R$_8$, X denotes HN, $C_1$-$C_4$alkyl-N, O(CH$_2$)$_g$NH, O or S and the remaining radicals and symbols $R_1$, $R_4$, $R_5$, %, $R_7$, $R_8$ and g are as defined for a compound of the formula I, the 5-pyrimidyl carboxylic acid of formula II

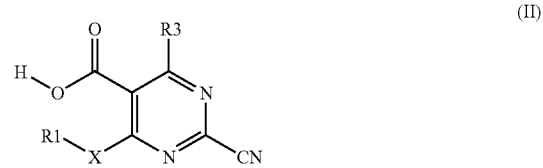

(II)

wherein $R_3$ denotes hydrogen, halogen, phenyl, pyridyl, which is unsubstituted or mono-, di- or trisubstituted by halogen, Y—$R_6$, wherein Y represents O, NH or S, or NR$_7$R$_8$, X denotes HN, $C_1$-$C_4$alkyl-N, O(CH$_2$)$_g$NH, O or S, and the remaining radicals and symbols $R_1$, $R_6$, $R_7$, $R_8$ and g are as defined for a compound of the formula I, is reacted as defined under process variant (a) with an amine of formula III

(III)

wherein the symbols $R_4$ and $R_5$ are as defined for a compound of the formula I;

b) alternatively for the synthesis of a compound of the formula I wherein $R_2$ represents $C(O)NR_4R_5$, $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl-N, $O(CH_2)_g NH$, O or S and the remaining radicals and symbols $R_1$, $R_4$, $R_5$, $R_6$, $R_7$, $R_8$ and g are as defined for a compound of the formula I, the 6-chloro pyrimidine derivative of formula IV

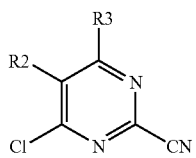
(IV)

wherein $R_2$ denotes —$C(O)NR_4R_5$, $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, and the remaining radicals $R_6$, $R_7$ and $R_8$ are as defined for a compound of the formula I, is reacted as defined under process variant (b) with a compound of formula V $$R_1\text{—}X\text{—}H \qquad (V)$$

wherein X denotes HN, $C_1$-$C_4$alkyl-N, $O(CH_2)_g NH$, O or S and $R_1$ has the meaning as defined for a compound of the formula I;

c) for the synthesis of a compound of the formula I wherein $R_2$ denotes —$N(R_9)SO_2R_{10}$, $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl-N, $O(CH_2)_g NH$, O or S and the remaining radicals and symbols $R_1$, $R_6$, $R_7$, $R_8$, $R_9$, $R_{10}$ and g are as defined for a compound of the formula I, the 5-amino pyrimidine of formula VI

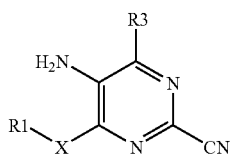
(VI)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl-N, $O(CH_2)_g NH$, O or S and the remaining radicals and symbols $R_1$, $R_6$, $R_7$, $R_8$ and g are as defined for a compound of the formula I, is reacted as defined under process variant (c) with a sulfonyl halide of formula VII

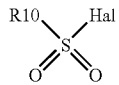
(VII)

wherein the radical $R_{10}$ is as defined for a compound of the formula I and Hal denotes halide, optionally followed by replacing the hydrogen atom in the sulfonamide function of the obtained compound of formula I by the group $R_9$ by means of an alkylation reaction;

wherein in all cases the starting materials of formula II to VII may also be present with functional groups in protected form, if necessary, and/or in the form of salts, provided a salt-forming group is present and the reaction in salt form is possible;

wherein any protecting groups in a protected derivative of a compound of the formula I are subsequently removed;

and, if so desired, an obtainable compound of formula I is converted into another compound of formula I, a free compound of formula I is converted into a salt, an obtainable salt of a compound of formula I is converted into the free compound or another salt, and/or a mixture of isomeric compounds of formula I is separated into the individual isomers.

Detailed Description of the Process Variants (a), (b) and (c):

Process Variant (a)

The amination of the carboxylic acid of formula II can be accomplished by standard procedures known in the art, e.g., by reacting both compounds in a suitable solvent by the addition of a suitable coupling agent, such as $POCl_3$, sulfuryl chloride fluoride, $P_2I_4$ or, in particular, N-(3-dimethylaminopropyl)-N'-ethylcarbodiimide hydrochloride (EDC-HCl) or N,N'-dicyclohexylcarbodiimide (DCC). When using EDC-HCl or DCC the reaction can be carried out, e.g., in dimethylformamide, at a temperature between about 10° C. and about 35° C., e.g. about 20 to 24° C., for a period of about 3 to 48 hours, e.g. 24 hours or 36 hours.

Process Variant (b)

The reaction preferably takes place under standard conditions useful in the nucleophilic re-placement of leaving groups with amino compounds. The 6-chloro pyrimidine derivative of formula IV can be reacted with the nucleophil of formula V in the presence of a base in a suitable solvent. If, e.g., X denotes NH, $C_1$-$C_4$alkyl-N or $O(CH_2)_g NH$, the reaction can be carried out by addition of a base, e.g. a nitrogen base, such as triethylamine, or a basic salt, such as an alkali metal carbonate, e.g. potassium carbonate, to the starting materials of formula IV and V in a suitable solvent; such as an ether, for example dioxane or tetrahydrofurane, or nitrites, such as acetonitrile, and heating the reaction mixture to about reflux temperature of the solvent for a period of about 6 to 12 hours, especially between 8 hours and 10 hours.

Process Variant (c)

The sulfonylamide of formula I wherein $R_2$ denotes —$N(R_9)SO_2R_{10}$ can be prepared by adding the sulfonylhalide of formula VII to a solution of the amine of formula VI in a suitable solvent such as dichloromethane or chloroform in the presence of an equimolar amount of pyridine or a similar base and, optionally, catalytic amounts of dimethylamino pyridine, at a temperature between about 10° C. and about 50° C., e.g. between about 20 and 25° C., for a period of about 1 to 12 hours, e.g. between 2 hours and 6 hours.

Protecting Groups

If one or more other functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Additional Process Steps

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

The solvents from which those can be selected which are suitable for the reaction in question include for example water, esters, typically lower alkyl-lower alkanoates, e.g diethyl acetate, ethers, typically aliphatic ethers, e.g. diethyl-ether, or cyclic ethers, e.g. tetrahydrofuran, liquid aromatic hydrocarbons, typically benzene or toluene, alcohols, typically methanol, ethanol or 1- or 2-propanol, nitrites, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

In the preferred embodiment, a compound of formula I is prepared according to or in analogy to the processes and process steps defined in the Examples.

The dosage of the active Ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

The invention relates also to pharmaceutical compositions comprising an effective amount, especially an amount effective in the treatment of one of the above-mentioned disorders, of compound of the formula I or a tautomer thereof together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectioning, dissolving or lyophilising processes, and comprise approximately from 1% to 95%, especially from approximately 1% to approximately 20%, active ingredient(s).

Starting Materials

Starting materials of the formula II to VII are known, commercially available, or can be synthesized in analogy to or according to methods that are known in the art, described in the Examples or, in particular, as described hereinbelow.

The 5-pyrimidyl carboxylic acid of formula II

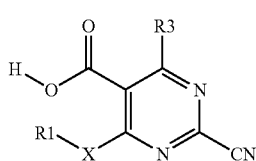

(II)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl-N or $O(CH_2)_g$NH, and the remaining radicals and symbols $R_1$, $R_6$, $R_7$, $R_8$ and g are as defined for a compound of the formula I, can be obtained by reacting the 5-pyrimidyl carboxylic acid halide of the formula VIII

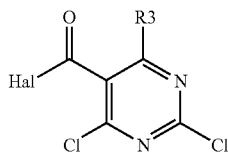

(VIII)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, and the remaining radicals $R_6$, $R_7$ and $R_8$ are as defined for a compound of the formula I, in a first step with an alcohol AlkOH, wherein Alk denotes alkyl, preferably $C_1$-$C_4$alkyl, and in a second step with an amine of the formula V

$R_1$—X—H (V)

wherein X denotes HN, $C_1$-$C_4$alkyl-N, $O(CH_2)_g$NH, and $R_1$ is as defined for a compound of the formula I, in order to prepare the 2-chloro-pyrimidine of formula IX,

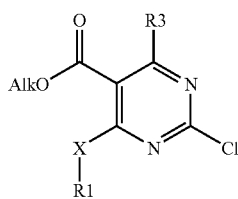

(IX)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, Alk denotes alkyl, preferably $C_1$-$C_4$alkyl, X denotes HN, $C_1$-$C_4$alkyl-N, $O(CH_2)_g$NH, and g, $R_1$, $R_6$, $R_7$ and $R_8$ are as defined for a compound of the formula I.

The reaction of the 5-pyrimidyl carboxylic acid halide of the formula VIII with the alcohol AlkOH can be carried out under customary conditions, e.g., by dissolving the acid halide in a suitable solvent, such as dichloromethane, and adding staggered or simultaneously the alcohol and an equivalent amount of a suitable base, such as a tri($C_1$-$C_4$alkyl) amine, at a temperature between −10 and 25° C., preferably at about 0° C. The obtained carboxylic acid ester can advantageously be further reacted without intermediate isolation thereof by addition of the amine of formula V and an equivalent amount of a suitable base, such as the same or a different tri($C_1$-$C_4$alkyl)amine as used above, at a temperature between −10 and +25° C., such as about 0° C.

The 2-chloro-pyrimidine of formula IX, wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, Alk denotes alkyl, preferably $C_1$-$C_4$alkyl, X denotes HN, $C_1$-$C_4$alkyl-N, $O(CH_2)_g$NH and g, $R_1$, $R_6$, $R_7$ and $R_8$ are as defined for a compound of the formula I, is then further reacted for a period of 15 to 360 minutes with an alkali metal cyanide, such as potassium cyanide, in a suitable solvent, such as dimethylformamide or dimethylsulfoxide, in the presence of a suitable base, such as 1,4-diazabicyclo[2.2.2]octane, at a temperature between +15 and +35° C., preferably at about 20 to 25° C., furnishing the 2-cyano-pyrimidine-5-carboxylic acid ester of formula X

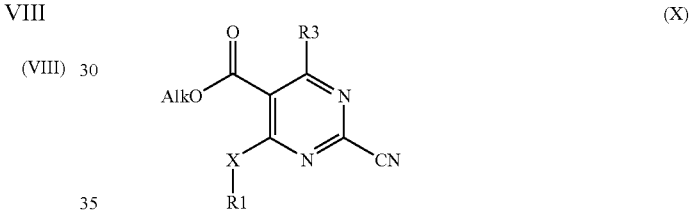

(X)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, Alk denotes alkyl, preferably $C_1$-$C_4$alkyl, X denotes HN, $C_1$-$C_4$alkyl-N, $O(CH_2)_g$NH, and g, $R_1$, $R_6$, $R_7$ and $R_8$ are as defined for a compound of the formula I. Said carboxylic acid ester of formula X is then finally subjected to a saponification reaction by addition of a great excess of water under conditions known in the art catalyzed by a suitable base furnishing the 5-pyrimidyl carboxylic acid of formula II as defined above. For instance, the carboxylic acid ester can be solved in a solvent miscible with water, such a tetrahydrofuran, and a solution of a suitable base, such as lithium hydroxide, in water is added at a temperature between −5 and 20° C., preferably at about 0° C.

The 5-pyrimidyl carboxylic acid of formula II

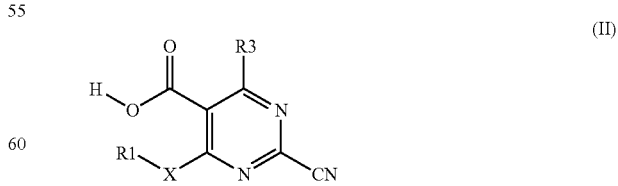

(II)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes O or S, and the remaining radicals $R_1$, $R_5$, $R_7$ and $R_5$ are as defined for a compound of the formula I, can be obtained by reacting the 5-pyrimidyl carboxylic acid halide of the formula VIII wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, and the remaining radicals $R_6$, $R_7$ and $R_8$ are as defined for a compound of the formula I, in a first step with water, and in a second step with an alcohol or thiol of the formula V, wherein X denotes O or S and $R_1$ is as defined for a compound of the formula I, in order to prepare the 2-chloro-pyrimidyl-5-carboxylic acid of formula XI,

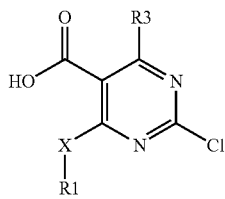

(XI)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes O or S, and the remaining radicals $R_1$, $R_6$, $R_7$ and $R_8$ are as defined for a compound of the formula I.

The reaction of the 5-pyrimidyl carboxylic acid halide of the formula VIII with water can be carried out under customary conditions, e.g., by dissolving the acid halide in a suitable solvent which is miscible with water, such as tetrahydrofuran, and adding an excess amount of water, at a temperature between 15 and 35° C., preferably at about 20 to 25° C. The obtained carboxylic acid is reacted with a strong base, such as potassium tert-butoxide, and the alcohol or thiol of the formula V in a suitable solvent, such as tetrahydrofuran, for a period of 30 to 360 minutes at a temperature between −10 and 20° C., preferably at about 0° C.

The 2-chloro-pyrimidyl-5-carboxylic acid of formula XI, wherein the radicals have the meanings as provided above, is then reacted in a suitable solvent such as dimethylformamide at a temperature between 30 and 60° C., preferably at about 45 to 55° C. for a period of 10 to 120 minutes, more preferably 30 to 45 minutes, with an excess amount of an allyl halide, e.g. allylbromide, in the presence of a suitable base, such as potassium carbonate, delivering the carboxylic allyl ester of formula (XII),

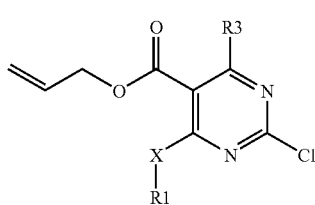

(XII)

wherein the radicals have the meanings as provided for the compound of formula XI above.

The carboxylic allyl ester of formula (XII), wherein the radicals have the meanings as provided for the compound of formula XI above, is then reacted for a period of 15 to 360 minutes with an alkali metal cyanide, such as potassium cyanide, in a suitable solvent, such as dimethylformamide or dimethylsulfoxide, in the presence of a suitable base, such as 1,4-diazabicyclo[2.2.2]octane, at a temperature between +15 and +35° C., preferably at about 20 to 25° C., to furnish the carboxylic allyl ester of formula (XIII),

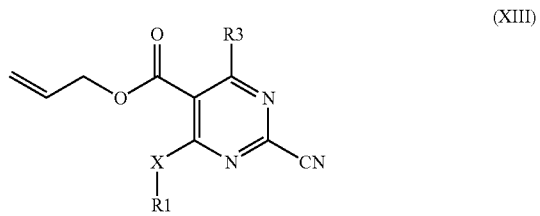

(XIII)

wherein the radicals have the meanings as provided for the compound of formula XI above.

Finally, the compound of formula II as defined above is obtained by hydrolysis of said carboxylic allyl ester of formula XIII by addition of a Pd(0) catalyst, e.g. tetrakis(triphenylphosphine)palladium(0), and morpholine to a solution of the allyl ester in a suitable solvent, such as tetrahydrofuran, at a temperature between +15 and +35° C., preferably at about 20 to 25° C., followed by addition of an aqueous solution of sodium hydrogencarbonate.

The 5-pyrimidyl carboxylic acid of formula II wherein $R_3$ denotes Y—$R_6$, wherein Y represents O, NH or S, X denotes HN, $C_1$-$C_4$alkyl-N or $O(CH_2)_gNH$, and the remaining radicals and symbols $R_1$, $R_6$ and g are as defined for a compound of the formula I, can also be obtained by reacting firstly the 2-methylthio-5-pyrimidyl carboxylic acid of the formula XIV

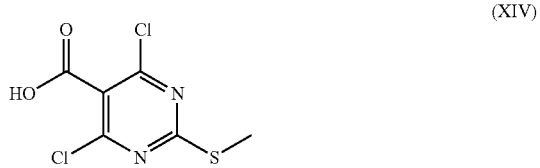

(XIV)

with the amine, alcohol or thiol of formula XV

 (XV)

wherein $R_3$ denotes Y—$R_6$, wherein Y represents O, NH or S and $R_6$ is as defined for a compound of the formula I, in the presence of a strong base, such as sodium hydrid, in a suitable solvent such as tetrahydrofuran at a temperature between −10 and 30° C., preferably at about 20° C., and, subsequently, the reaction product is reacted in a suitable solvent such as dimethylformamide at a temperature between 30 and 60° C., preferably at about 45 to 55° C., for a period of 10 to 120 minutes, more preferably 45 to 75 minutes, with an excess amount of an allyl halide, e.g. allylbromide, in the presence of a suitable base, such as potassium carbonate, delivering the carboxylic allyl ester of formula XVI,

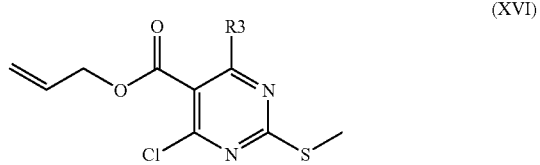

(XVI)

wherein $R_3$ denotes Y—$R_6$, wherein Y represents O, NH or S and $R_6$ is as defined for a compound of the formula I.

The methylthio group in the carboxylic allyl ester of formula XVI is subsequently replaced by a cyano group by means of a two step reaction. In the first step, the carboxylic allyl ester of formula XVI, wherein the radicals have the meanings as provided above, is oxidized with a suitable oxidizing agent, preferably with a 3-fold molar excess of meta chloro perbenzoic acid, in a suitable solvent, such as dichloromethane, at a temperature between −10 and +10° C., preferably at about 0° C. In a second step, the resulting methyl sulfonyl group is replaced by a cyano group by reaction of the obtained intermediate in a suitable solvent, for instance dichloromethane, with a suitable cyanide, e.g. sodium cyanide, in the presence of a suitable catalyst, such as tetra(alkyl) ammonium bromide, at a temperature between 15 and 30° C., preferably at about 20 to 25° C., furnishing the 2-cyano pyrimidyl-5-carboxylic acid allyl ester of formula XVII,

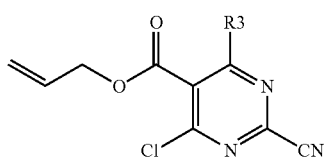
(XVII)

wherein $R_3$ denotes Y—$R_6$, wherein Y represents O, NH or S and $R_6$ is as defined for a compound of the formula I.

The obtained 2-cyano pyrimidyl-5-carboxylic acid allyl ester of formula XVII, wherein $R_3$ denotes Y—$R_6$, wherein Y represents O, NH or S and $R_6$ is as defined for a compound of the formula I, is finally transferred into the carboxylic acid of formula II by first reacting 2-cyano pyrimidyl-5-carboxylic acid allyl ester of formula XVII with the amine of formula V and an equivalent amount of a suitable base, such as the same or a different tri($C_1$-$C_4$alkyl)amine as used above, at a temperature between −10 and +25° C., such as about 0° C., and secondly by hydrolysis of the obtained allyl ester by addition of a Pd(0) catalyst, e.g. tetrakis(triphenylphosphine)palladium(0), and morpholine to a solution of the allyl ester in a suitable solvent, such as tetrahydrofuran, at a temperature between +15 and +35° C., preferably at about 20 to 25° C., followed by addition of an aqueous solution of sodium hydrogencarbonate.

The 6-chloro pyrimidine derivative of formula IV

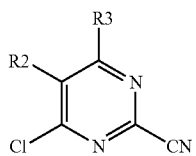
(IV)

wherein $R_2$ denotes —C(O)$NR_4R_5$, $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, and the remaining radicals $R_6$, $R_7$ and $R_8$ are as defined for a compound of the formula I, can be obtained starting from the 2-methylthio-5-pyrimidyl carboxylic acid of the formula XIV

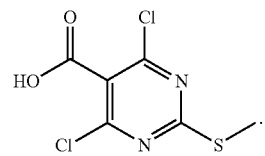
(XIV)

Said carboxylic acid can be reacted as specified in the Examples with oxalyl chloride to furnish the corresponding carboxylic acid chloride, which can be transferred by reaction with the amine of formula III, wherein $R_4$ and $R_5$ have the meanings as defined for a compound of formula I above, into the carboxylic acid amide of formula XVIII,

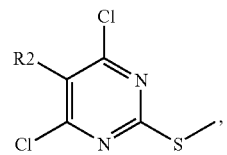
(XVIII)

wherein $R_2$ denotes —C(O)$NR_4R_5$ and $R_4$ and $R_5$ have the meanings as defined for a compound of formula I above. Such carboxylic acid amide of formula XVIII can be further reacted with the amine, alcohol or thiol of formula XV wherein $R_3$ denotes Y—$R_6$, wherein Y represents O, NH or S and $R_6$ is as defined for a compound of the formula I, in the presence of a strong base, such as sodium hydride, in a suitable solvent such as tetrahydrofuran at a temperature between −10 and 30° C., preferably at about 20° C., furnishing the 2-methylthiopyrimidine derivative of formula XIX,

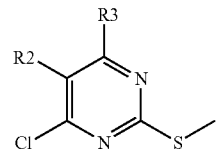
(XIX)

wherein $R_2$ denotes —C(O)$NR_4R_5$, $R_3$ denotes Y—$R_6$, wherein Y represents O, NH or S, and $R_4$, $R_5$ and $R_6$ have the meanings as defined for a compound of formula I above.

The methylthio group in the carboxylic allyl ester of formula XIX is finally replaced by a cyano group by means of a two step reaction as described for the carboxylic allyl ester of formula XVI, to result in the 6-chloro pyrimidine derivative of formula IV as described above.

The 5-amino pyrimidine derivative of formula VI

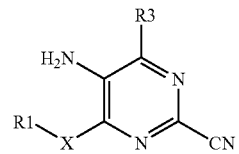
(VI)

wherein $R_3$ denotes hydrogen, halogen, phenyl, pyridyl, which is unsubstituted or mono-, di- or trisubstituted by halogen, Y—R₆, wherein Y represents O, NH or S, or NR₇R₈, X denotes HN, C₁-C₄alkyl-N, O(CH₂)ₘNH, O or S and the remaining radicals and symbols R₁, R₆, R₇, R₈ and g are as defined for a compound of the formula I, can be obtained starting from the 2-methylthio-5-pyrimidyl carboxylic acid of the formula XIV

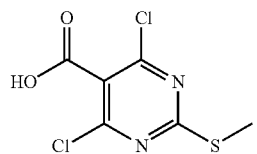

(XIV)

as follows:

In the first step, the carboxylic acid of the formula XIV is transferred to the corresponding carbamic acid allyl ester of formula XX

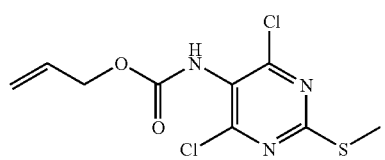

(XX)

as specified in the Examples below.

Such carbamic acid allyl ester of formula XX can be further reacted with the amine, alcohol or thiol of formula XV wherein R₃ denotes Y—R₆, wherein Y represents O, NH or S and R₆ is as defined for a compound of the formula I, in the presence of a strong base, such as sodium hydride or potassium tert-butoxide, in a suitable solvent such as tetrahydrofuran at a temperature between −10 and 30° C., preferably at about 20° C., furnishing the 2-methylthiopyrimidine derivative of formula XXI,

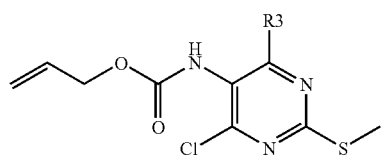

(XXI)

wherein R₃ denotes Y—R₆, wherein Y represents O, NH or S and R₆ is as defined for a compound of the formula I.

The methylthio group in the 2-methylthio-pyrimidine of formula XXI is subsequently replaced by a cyano group by means of a two step reaction as described for the carboxylic acid allyl ester of formula XIX above, furnishing the 2-cyano pyrimidyl-5-carbamic acid allyl ester of formula XXII,

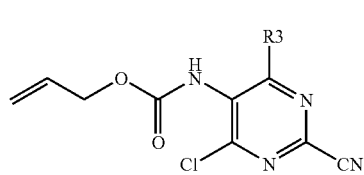

(XXII)

wherein R₃ denotes Y—R₆, wherein Y represents O, NH or S and R₆ is as defined for a compound of the formula I.

Said 2-cyano pyrimidyl-5-carbamic acid allyl ester is finally transferred into the 5-amino pyrimidine derivative of formula VI by first reacting the compound of formula XXII with an amine of formula V as specified hereinabove and subsequent hydrolysis of the carbamic acid function in the obtained intermediate by addition of a Pd(0) catalyst, e.g. tetrakis-(triphenylphosphine)palladium(0), and morpholine to a solution of the carbamic acid allyl ester in a suitable solvent, such as tetrahydrofuran, at a temperature between +15 and +35° C., preferably at about 20 to 25° C., followed by addition of an aqueous solution of sodium hydrogencarbonate.

Starting from the 5-amino pyrimidine derivative of formula VI wherein the radicals are as defined for a compound of formula I above, the 2-cyano pyrimidines of formula I wherein R₂ denotes —NHC(O)R₄, wherein R₄ is as defined for a compound of formula I above, can be obtained by simple acylation reactions which are known as such in the art.

The spirocyclic starting materials being incorporated in radical R₁ can be prepared in accordance with the procedures described in the Examples or by acetalisation reactions. The diols being used as a starting material for such procedures described in the Examples as well as for acetalisation reactions can be, for instance, be prepared by subjecting in a first step a dicarboxylic acid ester of formula XXIII,

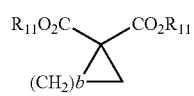

(XXIII)

wherein R₁₁ is C₁-C₄alkyl and b is an integer selected from 1, 2 or 3, to a reduction reaction, e.g. to reduction with LiAlH₄ in tetrahydrofuran, to furnish the diol of formula (XXIV).

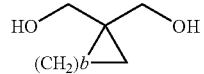

(XXIV)

wherein b is an integer selected from 1, 2 or 3. In a second step the hydroxy groups are transferred into suitable leaving groups for nucelophilic substitution reactions, e.g. by reaction with p-tosylchloride in the presence of a suitable base, such as triethylamine, under suitable reaction conditions. Subsequently, nucelophilic substitution reaction is carried out with potassium cyanide in an aprotic solvent, such as dimethylsulfoxide, to deliver the di-(cyanomethyl)cycloalkyl compound of formula XXV

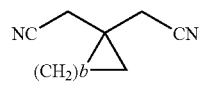

(XXV)

wherein b is an integer selected from 1, 2 or 3. The di-(cyanomethyl)cycloalkyl compound of formula XXV is then further subjected to alkaline hydrolysis providing the free di-carboxylic acid derivative and finally said di-carboxylic acid derivative is reduced, e.g. by reduction with LiAlH₄ in tetrahydrofuran, to the diol of formula (XXVI),

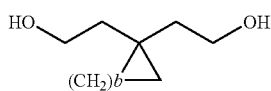

(XXVI)

wherein b is an integer selected from 1, 2 or 3.

EXAMPLES

The Examples which follow serve to illustrate the invention without limiting the scope thereof.

Temperatures are measured in degrees Celsius. Unless indicated otherwise, reactions are carried out at room temperature. The structure of final products, intermediates and starting materials is confirmed by standard analytical methods, e.g. microanalysis and spectroscopic characteristics (e.g. MS, IR, NMR).

Abbreviations

Abbreviations used are those conventional in the art and, in particular, have the meanings provided below.

Ac acetyl
aq. Aqueous
Boc tert-butoxycarbonyl
conc. concentrated
mCPBA meta-chloroperbenzoic acid
DABCO 1,4-diazabicyclo[2.2.2]octane
DMAP dimethylaminopyridine
DMF dimethylformamide
DMSO dimethylsulfoxide
Et ethyl
EtOAc ethyl acetate
h hour(s)
iPr isopropyl
LAH lithium aluminium hydride
LDA lithium diisopropyl amide
Me methyl
MS mass spectrometry
NMR nuclear magnetic resonance
Ph phenyl
RP-HPLC reversed phase high pressure liquid chromatography
sat. saturated
soln. Solution
TBAB tetrabutylammonium bromide
TFA trifluoroacetic acid
THF tetrahydrofurane Starting Materials 2-Cyano-4-[(spiro[2.5]oct-6-ylmethyl)amino]pyrimidine-5-carboxylic acid To a solution of 4-chloro-2-cyano-pyrimidine-5-carbonyl chloride (8.80 mmol) in $CH_2Cl_2$ (30 mL) are successively added MeOH (9.60 mmol) and i-$Pr_2$NEt (9.80 mmol) at 0° C. After stirring at 0° C. for 15 min, to the reaction mixture are successively added C-spiro[2.5]oct-6-yl-methylamine hydrochloride (8.50 mmol) and triethylamine (24.0 mmol) at 0° C. The reaction mixture is stirred at 0° C. to room temperature for 50 min, and then the bulk of solvent is concentrated in vacuo. After the residue is diluted with AcOEt, the mixture is washed with aq. $KHSO_4$, water, sat. aq. $NaHCO_3$, water and brine. The organic layer is dried over $Na_2SO_4$, filtered, and concentrated in vacuo. The residue is directly used for the next reaction without further purification.

To a solution of the above residue in DMSO (10 mL) are successively added a solution of KCN (14.2 mmol) in water (2 mL) and DABCO (2.80 mmol) at room temperature. After stirred at the same temperature, the reaction mixture is diluted with AcOEt. The resulting mixture is washed with water (×2) and brine, dried over $Na_2SO_4$, filtered, and concentrated in vacuo. The resulting residue is purified by silica gel column chromatography (n-hexane:AcOEt=5:1) to afford the cyanopyrimidine, which is directly used for the next reaction without further purification.

To the above cyanopyrimidine in THF (20 mL) is added a solution of LiOH—$H_2O$ (19.0 mmol) in water (10 mL) at 0° C. After stirring at room temperature for 1 h, the reaction is quenched by the addition of aq. $KHSO_4$. The resulting precipitated solid is filtered, washed with water, and triturated with the small amount of $CH_3CN$ to afford the title compound; $^1H$ NMR (400 MHz, DMSO), δ 0.22 (2H, dd), 0.32 (2H, dd), 0.95-0.98 (2H, m), 1.15-1.24 (2H, m), 1.68-1.74 (5H, m), 3.47 (2H, t), 8.88 (1H, t).

4-(3,3-Difluoro-pyrrolidin-1-yl)piperidine hydrochloride

A mixture of 3,3-difluoro-pyrrolidine hydrochloride (2.02 mmol), 4-oxo-piperidine-1-carboxylic acid tert-butyl ester (2.02 mmol) and Ti(OiPr)$_4$ (2.42 mmol) in THF is stirred at room temperature for 1 h. To the resulting mixture are added ethanol (3 mL) and NaBH$_3$CN (1.21 mmol). After stirring for 17 h, the reaction is quenched by the addition of sat. aq. NaHCO$_3$ and the resulting precipitate is filtered out. After the filtrate is diluted with AcOEt, the mixture is washed with brine, dried over MgSO$_4$, and concentrated in vacuo. The residue is purified by silica gel column chromatography to give 4-(3,3-difluoro-pyrrolidin-1-yl)-piperidine-1-carboxylic acid tert-butyl ester; $^1H$ NMR (CDCl$_3$) δ: 1.34-1.52 (2H, m), 1.45 (9H, s), 1.79 (2H, bd), 2.19-2.33 (3H, m), 2.78 (2H, dd), 2.83 (2H, dd), 2.95 (2H, dd), 4.00 (2H, bs).

4-(3,3-difluoro-pyrrolidin-1-yl)-piperidine-1-carboxylic acid tert-butyl ester (1.77 mmol) is treated with 4N HCl in 1,4-dioxane (6 mL) and stirred at room temperature for 1 h. The reaction mixture is concentrated in vacuo and the resulting residue is used for the next step without further purification.

4-Phenyl-2-pyridin-2-yl-2H-pyrazol-3-ylamine

To a solution of 3-hydroxy-2-phenylacrylonitrile (3.4 mmol) in EtOH (6.8 mL) is added AcOH (0.66 mL) and 2-hydrazinopyridine (6.8 mmol) at room temperature. After stirred at 80° C. for 5 h, the reaction mixture is cooling and concentrated in vacuo. The residue is diluted with H$_2$O and extracted with AcOEt. The organic extracts are washed with brine, dried over Na$_2$SO$_4$ and concentrated in vacuo. The resulting residue is triturated with ether to give the title compound; $^1H$ NMR (CDCl$_3$) δ 6.27 (br, 2H), 7.11-7.14 (m, 1H), 7.21-7.25 (m, 1H), 7.40-7.48 (m, 4H), 7.65 (s, 1H), 7.79-7.84 (m, 1H), 8.02 (d, 1H), 8.35-8.37 (m, 1H).

3-Cyclopropyl-2,2-dimethylpropylamine hydrochloride

To a solution of isobutyronitrile (29 mmol) in THF (60 mL) is added LDA (2 M in THF, 35 mmol) at −78° C. After stirring at −78° C. for 2 h, to this solution is added bromomethyl cyclopropane (32 mmol) at −78° C. The mixture is stirred at room temperature for 13 h, and then the reaction is quenched by the addition of aq. NH$_4$Cl. The mixture is extracted with ether, and the combined organic extracts are washed with H$_2$O and brine. The organic layer is dried over MgSO$_4$, filtered, and concentrated in vacuo to give 3-cyclopropyl-2,2-dimethylpropionitrile, which is directly used for the next reaction without further purification.

To a suspension of LAH (87 mmol) in THF (200 mL) is added dropwise conc. H$_2$SO$_4$ (44 mmol) at 0° C. After stirred at 0° C. for 0.5 h, to the suspension is added 3-cyclopropyl-2,2-dimethylpropionitrile at 0° C. The mixture is refluxed for 4.5 h. After cooling down to 0° C., the reaction is quenched by the addition of Na$_2$SO$_4$-10H$_2$O. The resulting mixture is filtered through celite, and the filtrate is treated with HCl in 1,4-dioxane. The resulting suspension is concentrated in vacuo to give the title compound; $^1$H NMR (DMSO) δ: 0-0.03 (2H, m), 0.39-0.44 (2H, m), 0.97 (6H, s), 1.19 (2H, d), 2.66 (q, 2H), 8.05 (3H, br).

2-Cyclopropyl-2-methylpropylamine hydrochloride

To a solution of cyclopropylacetonitrile (25 mmol) in THF (60 mL) is added LDA (2 M in THF, 30 mmol) at −78° C. After stirring at −78° C. for 2 h, to the solution is added iodomethane (30 mmol) at −78° C. The reaction mixture is stirred at room temperature for 1 h, and then the reaction is quenched by the addition of aq. NH$_4$Cl. After the mixture is extracted with ether, the organic extracts are washed with water and brine. The organic layer is dried over MgSO$_4$, filtered, and concentrated in vacuo to give 2-cyclopropylpropionitrile, which is directly used for the next reaction without further purification.

To a solution of the 2-cyclopropylpropionitrile (25 mmol) in THF (60 mL) is added LDA (2 M in THF, 74 mmol) at −78° C. After stirring at −78° C. for 2.5 h, to the solution is added iodomethane (99 mmol) at −78° C. The reaction mixture is stirred at room temperature for 11 h, and then the reaction is quenched by the addition of aq. NH$_4$Cl. After the mixture is extracted with ether, the organic extracts are washed with water and brine. The organic layer is dried over MgSO$_4$, filtered, and concentrated in vacuo to give 2-cyclopropyl-2-methylpropionitrile, which is directly used for the next reaction without further purification.

To a suspension of LAH (87 mmol) in THF (200 mL) is added dropwise conc. H$_2$SO$_4$ (44 mmol) at 0° C. After stirring at 0° C. for 0.5 h, to the suspension is added the 3-cyclopropyl-2,2-dimethylpropionitrile at 0° C. The reaction mixture is refluxed for 4.5 h. After cooling down to 0° C., the reaction is quenched by the addition of Na$_2$SO$_4$-10H$_2$O. The resulting mixture is filtered through celite, and the filtrate is treated with HCl in 1,4-dioxane. The resulting suspension is concentrated in vacuo to give the title compound, which is directly used for the next reaction without further purification.

2-(1-Methylcyclobutyl)ethylamine hydrochloride

To a solution of cyclobutanecarboxylic acid (50 mmol) in THF (100 mL) is added LDA (2 M in THF, 125 mmol) at 0° C. After stirring at 0° C. for 2 h, to the solution is added iodomethane (125 mmol) at 0° C. The reaction mixture is stirred at room temperature for 14 h. The reaction is quenched by the addition of water, and then the aqueous layer is separated from THF layer. To this aqueous layer is added aq. NH$_4$Cl, and the mixture is acidified to pH<2 with aq. HCl. After the mixture is extracted with AcOEt, the organic extracts are washed with water and brine. The organic layer is dried over MgSO$_4$, filtered, and concentrated in vacuo to give 1-methylcyclobutanecarboxylic acid, which is directly used for the next reaction without further purification.

To a suspension of LAH (200 mmol) in THF (250 mL) is added 1-methylcyclobutanecarboxylic acid (32 mmol) at 0° C. The reaction mixture is stirred at 60° C. for 6 h. After cooled down to 0° C., the reaction is quenched by the addition of Na$_2$SO$_4$-10H$_2$O. The resulting mixture is filtered through celite, and the filtrate is concentrated in vacuo to give the (1-methylcyclobutyl)methanol, which is directly used for the next reaction without further purification.

To a solution of (1-methylcyclobutyl)methanol (32 mmol) in CH$_2$Cl$_2$ (100 mL) are added triethylamine (65 mmol), trimethylamine hydrochloride (6 mmol), and a solution of p-toluenesulfonyl chloride (49 mmol) in CH$_2$Cl$_2$ (50 mL) at 0° C., then the mixture is stirred at 0° C. for 0.5 h. The reaction is quenched by the addition of water, and the mixture is extracted with CH$_2$Cl$_2$. The combined organic extracts are washed with water and brine. The organic layer is dried over Na$_2$SO$_4$, filtered, and concentrated in vacuo to give toluene-4-sulfonic acid 1-methylcyclobutylmethyl ester, which is directly used for the next reaction without further purification.

To a solution of the toluene-4-sulfonic acid 1-methylcyclobutylmethyl ester in DMF (60 mL) is added potassium cyanide (60 mmol). The reaction mixture is stirred at 60° C. for 11 h. After cooled to room temperature, the mixture is diluted with water, and then extracted with ether. The combined organic extracts were washed with water and brine, dried over Na$_2$SO$_4$, filtered, and concentrated in vacuo to (1-methylcyclobutyl)acetonitrile, which is directly used for the next reaction without further purification.

To a suspension of LAH (97 mmol) in THF (200 mL) is added dropwise conc. H$_2$SO$_4$ (49 mmol) at 0° C. After stirred at 0° C. for 1 h, to the suspension is added (1-methylcyclobutyl)acetonitrile at 0° C. The reaction mixture is refluxed for 4.5 h. After cooled down to 0° C., the reaction is quenched by the addition of Na$_2$SO$_4$-10H$_2$O. The resulting mixture is filtered through celite, and the filtrate is treated with HCl in 1,4-dioxane, and then the suspension is concentrated in vacuo to give the title compound, which is directly used for the next reaction without further purification.

2-Phenyl-2-pyrrolidin-1-ylethylamine dihydrochloride

To a suspension of benzaldehyde (9.4 mmol) in H$_2$O (6 mL) are added sodium hydrogensulfate (9.4 mmol) and pyrrolidine (9.4 mmol). After stirring at room temperature for 0.5 h, to the suspension is added sodium cyanide (9.4 mmol), and the resulting mixture is stirred at room temperature for 15 h. The reaction mixture is diluted with sat. aq. NaHCO$_3$, then extracted with AcOEt. The organic extracts are washed with water (×2) and brine, dried over Na$_2$SO$_4$, filtered, and concentrated in vacuo to give phenylpyrrolidin-1-ylacetonitrile, which is directly used for the next reaction without further purification.

To a solution of LAH (26 mmol) in THF (100 mL) is added dropwise conc. H$_2$SO$_4$ (1.3 mmol) at 0° C. After stirred at 0° C. for 0.5 h, to the solution is added phenylpyrrolidin-1-ylacetonitrile at 0° C., then the mixture is stirred at 60° C. for 3 h. After cooled down to 0° C., the reaction is quenched by the addition of Na$_2$SO$_4$-10H$_2$O. The resulting mixture is filtered through celite, and the filtrate is concentrated in vacuo. After the residue is diluted with ether, the mixture is treated with HCl in 1,4-dioxane. The precipitate is collected by filtration to give the title compound, which is directly used for the next reaction without further purification; $^1$H NMR (DMSO) δ: 1.74-1.99 (4H, m), 2.87 (2H, br), 3.14 (2H, br), 3.40-3.78 (4H, m), 4.64 (1H, br), 7.50-7.53 (3H, m), 7.75-7.77 (2H, m), 8.26 (3H, br).

2-phenyl-3-pyrrolidin-1-yl propylamine

To a solution of tropic acid (0.12 mmol) and pyrrolidine (0.12 mmol) in DMF (20 mL) are added HOAt (0.18 mmol) and EDCI-HCl (0.18 mmol). The reaction mixture is stirred at room temperature for 14 h. The reaction mixture is diluted with water, then extracted with AcOEt. The organic extracts are successively washed with water, sat. aq, NaHCO$_3$, H$_2$O and brine, dried over Na$_2$SO$_4$, filtered, and concentrated in vacuo. The residue is purified by silica gel column chromatography to give 3-hydroxy-2-phenyl-1-pyrrolidin-1-yl propan-1-one.

To a solution of LAH (10 mmol) in THF (50 mL) is added 3-hydroxy-2-phenyl-1-pyrrolidin-1-yl propan-1-one (5 mmol) at 0° C. The reaction mixture is stirred at 0° C. for 1.5 h. After cooled down to 0° C., the reaction is quenched by the addition of Na$_2$SO$_4$-10H$_2$O. The resulting mixture is filtered through celite, and the filtrate is concentrated in vacuo to give 2-phenyl-3-pyrrolidin-1-yl propan-1-ol, which is directly used for the next reaction without further purification.

To a solution of 2-phenyl-3-pyrrolidin-1-yl propan-1-ol (3.4 mmol) in THF (10 mL) is successively added phthalimide (4.1 mmol), triphenylphosphine (5.1 mmol) and diethyl azodicarboxylate (5.1 mmol) at 0° C., then the mixture is stirred at 0° C. for 1.5 h. After dilution with water, the mixture is acidified to pH<3 with aq. KHSO$_4$ then washed with AcOEt. The aqueous layer basified to pH>11 with sat aq. NaHCO$_3$ then extracted with AcOEt. The organic extracts are washed with water and brine, dried over Na$_2$SO$_4$, filtered, and concentrated in vacuo. The residue is triturated with ether to give 2-(2-phenyl-3-pyrrolidin-1-yl propyl)isoindole-1,3-dione, which is directly used for the next reaction without further purification.

A solution of 2-(2-phenyl-3-pyrrolidin-1-yl propyl)isoindole-1,3-dione (3 mmol) and hydrazine monohydrate (6 mmol) in ethanol (10 mL) is refluxed for 3.5 h. The reaction mixture is cooled and filtered through celite. The filtrate is concentrated in vacuo to give the title compound, which is directly used for the next reaction without further purification.

C-[1-(4-methoxybenzyl)-4-phenyl-piperidin-4-yl]-methylamine dihydrochloride

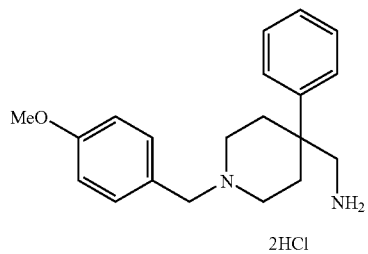

To a solution of 4-phenylpiperidine-4-carbonitrile (9.0 mmol) in MeOH (20 mL) is added 4-methoxybenzaldehyde (14 mmol) and sodium triacetoxyborohydride (27 mmol). The reaction mixture is stirred at room temperature for 2.5 h, and then the bulk of solvent is concentrated in vacuo. After dilution with water, and the mixture is extracted with AcOEt. The organic extracts are washed with water, sat. aq. NaHCO$_3$, water and brine, then dried over MgSO$_4$, filtered, and concentrated in vacuo. The residue is dissolved in ether, and then treated with HCl in AcOEt. The precipitate is collected by filtration to give 1-(4-methoxybenzyl)-4-phenylpiperidine-4-carbonitrile hydrochloride, which is directly used for the next reaction without further purification; $^1$H NMR (CDCl$_3$) δ: 2.19 (2H, d), 3.10-3.24 (4H, m), 3.59 (2H, d), 3.84 (3H, s), 4.17 (2H, d), 6.99 (2H, d), 7.35-7.45 (3H, m), 7.57-7.62 (4H, m), 13.08 (1H, br).

To a solution of LAH (27 mmol) in THF (100 mL) is added dropwise conc. H$_2$SO$_4$ (14 mmol) at 0° C. for 0.5 h, then 1-(4-methoxybenzyl)-4-phenylpiperidine-4-carbonitrile is added at 0° C., then the reaction mixture is refluxed for 2 h. After cooled down to 0° C., the reaction is quenched by the addition of Na$_2$SO$_4$-10H$_2$O. The resulting mixture is filtered through celite, and the filtrate is treated with HCl in 1,4-dioxane, then concentrated in vacuo to give the titled compound, which is directly used for the next reaction without further purification.

1-(4-aminomethyl-4-phenylpiperidin-1-yl)-ethanone hydrochloride

To a solution of C-[1-(4-methoxybenzyl)-4-phenyl-piperidin-4-yl]-methylamine dihydrochloride (3.9 mmol) in ether (20 mL) and 1 N aq. NaOH (20 mL) is added Boc$_2$O (4.6 mmol) at 0° C., then the mixture is stirred at room temperature for 18 h. The reaction mixture is acidified to pH<3 with 10% aq. KHSO$_4$, then the aqueous layer is separated from the organic layer. The acidic aqueous layer is basified to pH>12 with aq. NaOH, then the mixture is quickly extracted with AcOEt (×2). The combined organic extracts are washed with water and brine. The organic layer is dried over MgSO$_4$, filtered, and concentrated to give [1-(4-Methoxybenzyl)-4-phenylpiperidin-4-ylmethyl]carbamic acid tert-butyl ester, which is directly used for the next reaction without further purification.

To a solution of [1-(4-methoxy-benzyl)-4-phenylpiperidin-4-ylmethyl]carbamic acid tert-butyl ester (3.2 mmol) in CH$_2$Cl$_2$ is added 1-chloroethyl chloroformate (4.7 mmol), then the mixture is stirred at room temperature for 2.5 h. After the bulk of solvent is concentrated in vacuo, the residue suspended in ether and filtered. After the filtrate is concentrated in vacuo, the residue is suspended in hexane and filtered. The filtrate is concentrated in vacuo to give the 4-(tert-butoxycarbonylaminomethyl)-4-phenylpiperidine-1-carboxylic acid 1-chloroethyl ester, which is directly used for the next reaction without further purification.

A mixture of 4-(tert-butoxycarbonylaminomethyl)-4-phenylpiperidine-1-carboxylic acid 1-chloroethyl ester in MeOH is stirred at 60° C. for 5 h, then the reaction mixture is concentrated in vacuo to give (4-phenylpiperidin-4-ylmethyl) carbamic acid tert-butyl ester, which is directly used for the next reaction without further purification.

To a solution of (4-phenylpiperidin-4-ylmethyl) carbamic acid tert-butyl ester (2.1 mmol) in CH$_2$Cl$_2$ is added acetic anhydride (3.1 mmol) and triethylamine (3.1 mmol) at 0° C. The reaction mixture is stirred at room temperature for 2.5 h then the bulk of solvent is concentrated in vacuo. After the residue is suspended in AcOEt, the mixture is washed with water and brine, dried over MgSO$_4$, filtered, and concentrated in vacuo to give (1-acetyl-4-phenylpiperidin-4-ylmethyl)carbamic acid tert-butyl ester, which is directly used for the next reaction without further purification.

To a solution of (1-acetyl-4-phenylpiperidin-4-ylmethyl) carbamic acid tert-butyl ester in ether is added 4 N HCl in 1,4-dioxane. The reaction mixture is stirred at room temperature for 1 h, and concentrated in vacuo. The resulting solid is washed with ether to give the title compound, which is directly used for the next reaction without further purification.

4-(2-Fluorophenyl)-1-methylpiperidine-4-carbonitrile hydrochloride

To a solution of (2-fluorophenyl)acetonitrile (15 mmol) in THF (20 mL) are successively added bis-(2-chloroethyl)methylamine hydrochloride (16 mmol), tetrabutylammonium hydrogensulfate (1.5 mmol), and 40% aq. NaOH (20 mL), then the mixture is refluxed for 5.5 h. The reaction mixture is cooled at room temperature, diluted with water, then extracted with THF. The organic extracts are washed with water (×2) and brine, dried over Na$_2$SO$_4$, filtered, and concentrated in vacuo. The residue is dissolved in ether, then HCl in 1,4-dioxane is added. The precipitate is collected by filtration to give the titled compound, which is directly used for the next reaction without further purification; $^1$H NMR (DMSO) δ: 2.43-2.60 (4H, m), 2.86 (3H, d), 3.20-3.28 (2H, m), 4.02-4.04 (2H, m), 7.31-7.40 (2H, m), 7.48-7.60 (2H, m), 11.16 (1H, br).

1,4-diphenylpiperidine-4-carbonitrile

To a suspension of 4-phenylpiperidine-4-carbonitrile hydrochloride (6.7 mmol) in toluene (30 mL) are successively added bromobenzene (8.0 mmol), sodium tert-butoxide (17 mmol), tri-o-tolylphosphine (1.3 mmol), and tris(dibenzylideneacetone)dipalladium (0.7 mmol), then the mixture is refluxed for 20 h. The reaction mixture is cooled, diluted with water, then extracted with AcOEt. The organic extracts are washed with water and brine, dried over Na$_2$SO$_4$, filtered, and concentrated in vacuo. The residue is purified by silica gel column chromatography to give the title compound; $^1$H NMR (CDCl$_3$) δ: 2.12-2.20 (2H, m), 2.23-2.28 (2H, m), 2.94-3.01 (2H, m), 3.86 (2H, d), 6.83 (1H, t), 7.04 (2H, d), 7.22-7.28 (2H, m), 7.36-7.41 (1H, m), 7.45-7.49 (2H, m), 7.56-7.59 (2H, m).

C-(1-methyl-4-phenylpiperidin-4-yl)methylamine dihydrochloride

To a solution of LAH (7.5 mmol) in THF (10 mL) is added dropwise conc. H$_2$SO$_4$ (3.8 mmol) at 0° C. After stirred at 0° C. for 0.5 h, 1-methyl-4-phenylpiperidine-4-carbonitrile hydrochloride (2.5 mmol) is added at 0° C. The reaction mixture is stirred at 60° C. for 6 h. After cooled down to 0° C., the reaction is quenched by the addition of Na$_2$SO$_4$-10H$_2$O. The resulting mixture is filtered through celite, and the filtrate is concentrated in vacuo. The residue is suspended in ether and treated with HCl in 1,4-dioxane. The resulting white solid is collected by filtration to give the title compound, which is directly used for the next reaction without further purification.

C-[4-phenyl-1-(2,2,2-trifluoroethyl)piperidin-4-yl]methylaminedihydrochloride

To a solution of 4-phenylpiperidine-4-carbonitrile hydrochloride (6.7 mmol) in pyridine (13 mL) is added trifluoroacetic anhydride (10 mmol) at 0° C., then the mixture is stirred at 0° C. for 1 h. The reaction mixture is diluted with water, and extracted with AcOEt. The organic extracts are successively washed with water and brine. The organic layer is dried over Na$_2$SO$_4$, filtered, and concentrated in vacuo to give 4-phenyl-1-(2,2,2-trifluoroacetyl)piperidine-4-carbonitrile, which is directly used for the next reaction without further purification.

To a solution of LAH (40 mmol) in THF (40 mL) is added dropwise conc. H$_2$SO$_4$ (20 mmol) at 0° C. and the mixture is stirred for 0.5 h. To the solution is added 4-phenyl-1-(2,2,2-trifluoroacetyl)piperidine-4-carbonitrile at 0° C., then the mixture is refluxed for 3 h. The reaction mixture is cooled down at 0° C. and the reaction is quenched by the addition of Na$_2$SO$_4$-10H$_2$O. The resulting mixture is filtered through celite, and the filtrate is concentrated in vacuo. The residue is suspended in ether and treated with HCl in 1,4-dioxane. The white solid is collected by filtration to give the titled compound, which is directly used for the next reaction without further purification.

C-spiro[3.5]non-7-yl-methylamine hydrochloride

To a solution of 1,1-di-(2-hydroxyethyl)-cyclobutane (37.8 g, 262 mmol) and Me$_3$N.HCl (5.136 g, 53.7 mmol) in CH$_2$Cl$_2$ (680 mL) is added Et$_3$N (146 mL, 1052 mmol) at 0° C. After 5 min, p-TsCl (106.4 g, 558 mmol) is added at the same temperature. The reaction mixture is stirred at 0° C. for 2 h, then warmed up to room temperature for 2 h. The resulting mixture is diluted with CH$_2$Cl$_2$ (1600 mL), and washed with aq. sat. NaHCO$_3$ (400 mL, pH of the eq. layer=9), and brine (400 mL). The organic layer is dried over Na$_2$SO$_4$, filtered, and concentrated in vacuo. The residue is purified by silica gel column chromatography (silica gel, n-hexane: EtOAc=2:1) to give the desired di-tosylate.

To a suspension of NaH (60%, 34.3 g, 858 mmol) in THF (890 mL) is added dropwise a solution of diethyl malonate (160 mL) in THF (640 mL) at 0° C. during 30 min. Hydrogen gas is vigorously liberated. After stirring at 0° C. for 10 min the white suspension dissolves to give a colorless solution and a solution of the di-tosylate from the previous reaction (110.9 g, 245 mmol) in THF (660 mL) is added dropwise at 0° C.

After stirring at 0° C. to room temperature for 1 h the reaction mixture (yellow suspension) is refluxed for 20 h. The mixture is cooled to 0° C., and then sat. aq. NH₄Cl (800 mL) and water (400 ml) are added at 0° C. The layers are separated. The aqueous layer is extracted with EtOAc (500 mL×4). The combined organic layers are washed with brine (500 mL), dried over MgSO₄, and concentrated in vacuo. The excess diethyl malonate is removed by distillation to give the desired spiro[3.5]cyclononane-7,7-di-carboxylic acid di-ethyl ester.

To a solution of spiro[3.5]cyclononane-7,7-di-carboxylic acid di-ethyl ester (62.4 g, 233 mmol) in DMSO (620 mL) is added LiCl (19.7 g) and H₂O (4.2 mL) at room temperature. The reaction mixture is stirred at 185° C. for 13 h. The mixture is cooled to 0° C., and poured into water (1600 mL). The resulting mixture is extracted with EtOAc (300 mL×4). The combined extracts are washed with water (150 ml×2), dried over MgSO₄, and concentrated in vacuo to give spiro [3.5]cyclononane-7-carboxylic acid ethyl ester, which is immediately subjected to the next reaction.

To a suspension of LiAlH₄ (15.6 g) in THF (450 mL) is added dropwise a solution of spiro[3.5]cyclononane-7-carboxylic acid ethyl ester in THF (220 mL) at 0° C. during 1 h. The reaction mixture is stirred at 0° C. to room temperature for 14 h and excess LiAlH₄ is quenched with Na₂SO₄.10H₂O at 0° C. The mixture is stirred at 0° C. for 30 min, and then filtered through a celite pad. The filtrate is concentrated to provide 7-(hydroxymethyl)-spiro[3.5]cyclononane.

To a solution of 7-(hydroxymethyl)-spiro[3.5]cyclononane (11 g, 71.3 mmol) in CH₂Cl₂ (100 mL) are added Et₃N (21.8 mL) and Me₃N.HCl (682 mg) at 0° C. A solution of p-toluenesulfonyl chloride (14.28 g) in CH₂Cl₂ (20 ml) is added dropwise to the reaction mixture at 0° C. The reaction mixture is stirred at 0° C. for 30 min, then the bulk of solvent is removed. After the residue is diluted with EtOAc (300 mL), the mixture is washed with aq. KHSO₄ (80 mL×2), water (80 mL), sat. aq. NaHCO₃ (80 mL), water (80 mL), and brine (80 mL). The organic layer is dried over Na₂SO₄, filtered, and concentrated to give the corresponding tosylate, which is directly used for the next reaction without further purification.

To a solution of the above tosylate in DMF (100 mL) is added NaN₃ (27.5 g) at room temperature. The reaction mixture is stirred at 60° C. for 13 h. After dilution with ether (300 mL), the mixture is washed with water (80 mL×2) and brine (80 mL). The organic layer is dried over Na₂SO₄, filtered, and concentrated to give 7-azidomethyl-spiro[3.5]cyclononane, which is directly used for the next reaction without further purification.

To a solution of the above azide in THF (100 mL)-H₂O (50 mL) is added Ph₃P (20 g) at room temperature. The reaction mixture is stirred at the same temperature for 3 h. After dilution with EtOAc (200 mL), the mixture is extracted with 1 N HCl (80 mL×3). The combined aqueous extracts are washed with CH₂Cl₂ (50 mL), and then basified with 6 N NaOH. The resulting mixture is extracted with ether (100 mL×3). The combined organic extracts are dried K₂CO₃, and filtered. To this filtrate 4 N hydrogen chloride in EtOAc is added, and the resulting hydrochloride salt is filtered, washed with ether, and dried at 55° C. under reduced pressure to furnish C-spiro[3.5]non-7-yl-methylamine hydrochloride.

Reference Example 1

2-Cyano-4-(cyclohexylmethylamino)pyrimidine-5-carboxylic acid(2-morpholin-4-yl-1-phenylethyl)amide

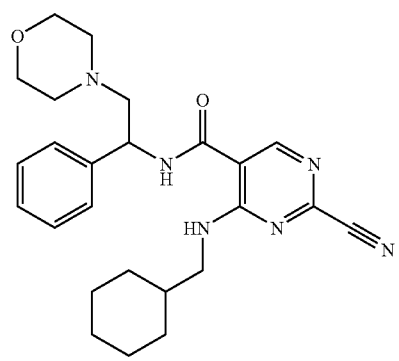

To a solution of 2-cyano-4-(cyclohexylmethylamino)-pyrimidine-5-carboxylic acid (0.33 mmol, step 1.4) in DMF (2.0 mL) are added 2-morpholin-4-yl-1-phenylethylamine (69 mg, step 1.3), EDCl—H₂O (0.50 mmol) and HOAt (0.50 mmol) at room temperature. After stirring at room temperature for 24 h, the reaction mixture is diluted with AcOEt. The mixture is washed with water, dried over Na₂SO₄, filtered, and concentrated in vacuo. The resulting residue is purified by RP-HPLC to give the title compound; ¹H NMR (DMSO) δ 0.6-1.08 (m, 2H), 1.20-1.35 (m, 3H), 1.65-1.78 (m, 6H), 2.48-2.53 (m, 2H), 2.60-2.62 (m, 2H), 2.87-2.93 (m, 2H), 3.31-3.35 (m, 1H), 3.36-3.44 (M, 1H), 3.60-3.68 (m, 4H), 5.29-5.35 (m, 1H), 7.34-7.36 (m, 1H), 7.43-7.47 (m, 2H), 7.50-7.52 (m, 2H), 8.86 (s, 1H), 9.00-9.04 (m, 1H), 9.21 (d, 1H).

Step 1.1:
(2-Morpholin-4-yl-2-oxo-1-phenylethyl)carbamic acid tert-butyl ester

To a solution of tert-butoxycarbonylaminophenylacetic acid (4.0 mmol) in CH₂Cl₂ (8.0 mL) is added morpholine (4.0 mmol), EDCl—H₂O (4.8 mmol) and DMAP (0.40 mmol) at room temperature. After stirring at room temperature for 24 h, the reaction is quenched by the addition of water. The mixture is extracted with AcOEt. The combined organic extracts are washed with brine, dried over Na₂SO₄ and concentrated in vacuo. The resulting solid is triturated with ether-n-hexane to give the title compound; ¹H NMR (CDCl₃) δ 1.41 (s, 9H), 3.08-3.12 (m, 1H), 3.20-3.28 (m, 1H), 3.39-3.45 (m, 1H), 3.49-3.60 (m, 3H), 3.66-3.76 (m, 2H), 5.54 (d, 1H), 6.01 (d, 1H), 7.29-7.36 (m, 5H).

Step 1.2:
2-Amino-1-morpholin-4-yl-2-phenylethanone

To a solution of (2-morpholin-4-yl-2-oxo-1-phenylethyl) carbamic acid tert-butyl ester (3.0 mmol) in CH₂Cl₂ (6.0 mL) is added TFA (2.0 mL) at 0° C. After stirring at room temperature for 24 h, the reaction mixture is basified to pH 8 with sat. aq NaHCO₃. The mixture is extracted with CH₂Cl₂, and then the combined organic extracts are dried over Na₂SO₄ and concentrated in vacuo to give the title compound; ¹H NMR (CDCl₃) δ 2.02 (s, 2H), 3.09-3.14 (m, 1H), 3.20-3.25 (m, 1H), 3.34-3.40 (m, 1H), 3.46-3.60 (m, 3H), 3.65-3.71 (m, 1H), 3.74-3.80 (m, 1H), 7.27-7.34 (m, 5H).

Step 1.3: 2-Morpholin-4-yl-1-phenylethylamine

To a stirred suspension of LAH (6.1 mmol) in THF (25 mL) is added dropwise a solution of 2-amino-1-morpholin-4-yl-2-phenylethanone (670 mmol) in THF (5 mL) at 0° C. The reaction mixture is refluxed for 2 hr, and then the reaction is quenched by the addition of $Na_2SO_4$-$10H_2O$ at 0° C. After stirring at room temperature for 0.5 h, the resulting mixture is filtered through celite, and the filtrate is concentrated in vacuo to give the title compound, which is directly used for the next reaction without further purification.

Step 1.4: 2-Cyano-4-(cyclohexylmethylamino)-pyrimidine-5-carboxylic acid

To a solution of 2,4-dichloro-pyrimidine-5-carbonyl chloride (8.80 mmol) in $CH_2Cl_2$ (30 mL) are successively added MeOH (9.60 mmol) and i-$Pr_2$NEt (9.80 mmol) at 0° C. After stirring at 0° C. for 15 min, to the reaction mixture are successively added cyclohexylmethylamine hydrochloride (8.50 mmol) and triethylamine (24.0 mmol) at 0° C. The reaction mixture is stirred at 0° C. to room temperature for 50 min, and then the bulk of solvent is concentrated in vacuo. After the residue is diluted with AcOEt, the mixture is washed with aq. $KHSO_4$, water, sat. aq, $NaHCO_3$, water and brine. The organic layer is dried over $Na_2SO_4$, filtered, and concentrated in vacuo. The residue is directly used for the next reaction without further purification.

To a solution of the above residue in DMSO (10 mL) are successively added a solution of KCN (14.2 mmol) in water (2 mL) and DABCO (2.80 mmol) at room temperature. After stirring at the same temperature for 1 h, the reaction mixture is diluted with AcOEt. The resulting mixture is washed with water (×2) and brine, dried over $Na_2SO_4$, filtered, and concentrated in vacuo. The resulting residue is purified by silica gel column chromatography (n-hexane:AcOEt=5:1) to afford the cyanopyrimidine, which is directly used for the next reaction without further purification.

To the above cyanopyrimidine in THF (20 mL) is added a solution of LiOH—$H_2O$ (19.0 mmol) in water (10 mL) at 0° C. After stirring at room temperature for 1 h, the reaction is quenched by the addition of aq. $KHSO_4$. The resulting precipitated solid is filtered, washed with water, and triturated with the small amount of $CH_3CN$ to afford the titled compound.

Reference Example 2

4-[2-(6-Chloro-2-methanesulfonylpyrimidin-4-yloxy)ethyl]-piperidine-1-carboxylic acid tert-butyl ester To a solution of the crude 4-[2-(6-chloro-2-methylsulfanylpyrimidin-4-yloxy)ethyl]piperidine-1-carboxylic acid tert-butyl ester (4.7 g, step Ref. Ex. 2.1) in $CH_2Cl_2$ (100 mL) is added m-CPBA (40 mmol) at 0° C. After stirring at room temperature for 3 h, the reaction mixture is quenched by 10% $Na_2SO_3$ at 0° C. The separated organic layer is washed twice with sat. $NaHCO_3$ and dried over $MgSO_4$. The organic layer is evaporated in vacuo. The resulting residue is dissolved in n-hexane:AcOEt (1:1) and silica gel is added to the mixture. After filtration, the filtrate is evaporated in vacuo to give a crude 4-[2-(6-chloro-2-methane-sulfonylpyrimidin-4-yloxy)ethyl]piperidine-1-carboxylic acid tert-butyl ester.

Ref. Example 2

Step 2.0: 4-[2-(6-Chloro-2-methylsulfanylpyrimidin-4-yloxy)-ethyl]piperidine-1-carboxylic acid tert-butyl ester NaH (6.4 mmol) is added to a solution of 4-(2-hydroxyethyl)piperidine-1-carboxylic acid tert-butyl ester (5.3 mmol) in THF (10 mL) at 0° C. After stirring at room temperature for 30 min, a solution of 4,6-dichloro-2-methylsulfanyl-pyrimidine (5.3 mmol) in THF (10 mL) is added dropwise to the reaction mixture. The reaction mixture is stirred at room temperature for 12 h and quenched by $H_2O$. The mixture is extracted with AcOEt. The organic layer is washed with $H_2O$, dried over $MgSO_4$ and evaporated in vacuo to give a crude 4-[2-(6-chloro-2-methylsulfanylpyrimidin-4-yloxy)ethyl]piperidine-1-carboxylic acid tert-butyl ester.

Ref. Example 2

Step 2.1: 4-[2-(6-Chloro-2-cyanopyrimidin-4-yloxy)ethyl]piperidine-1-carboxylic acid tert-butyl ester To a solution of the crude 4-[2-(6-chloro-2-methanesulfonylpyrimidin-4-yl oxy)ethyl]-piperidine-1-carboxylic acid tert-butyl ester (4.9 g) and NaCN (14 mmol) in $CH_2Cl_2$:$H_2O$ (50 mL, 4:1) is added TBAB (tetrabutylammonium bromide) (0.06 mmol) at room temperature. After stirring at the same temperature for 10 h, TBAB (0.19 mml) is added to the reaction mixture. The reaction mixture is stirred at room temperature for 2 h and $H_2O$ is added. The organic layer is separated, dried over $MgSO_4$ and evaporated in vacuo. The resulting residue is purified by silica gel column chromatography to give 4-[2-(6-chloro-2-cyanopyrimidin-4-yloxy)ethyl]piperidine-1-carboxylic acid tert-butyl ester; $^1$H-NMR ($CDCl_3$), δ: 1.14-1.28 (2H, m), 1.45 (9H, s), 1.56-1.78 (7H, m), 2.69 (2H, t), 4.11 (2H, m), 4.49 (2H, t), 6.93 (1H, s).

Ref. Example 2

Step 2.2: 4-(2-{2-Cyano-6-[(spiro[3.5]non-7-ylmethyl)amino]pyrimidin-4-yloxy}ethyl)piperidine-1-carboxylic acid tert-butyl ester To a solution of 4-[2-(6-chloro-2-cyanopyrimidin-4-yloxy)ethyl]piperidine-1-carboxylic acid tert-butyl ester (0.82 mmol) and C-spiro[3.5]non-7-ylmethylamine (0.86 mmol) in $CH_3CN$ (10 mL) is added $K_2CO_3$ (2.2 mmol) at room temperature. After stirring at 80° C. for 12 h, the reaction mixture is cooled to room temperature and diluted with AcOEt. The organic layer is washed twice with $H_2O$ and dried over $MgSO_4$ and evaporated in vacuo to give a crude 4-(2-{2-cyano-6-[(spiro[3.5]non-7-ylmethyl)amino]pyrimidin-4-yloxy}ethyl)piperidine-1-carboxylic acid tert-butyl ester.

Examples 2 to 57

By repeating the procedures described above using appropriate starting materials and conditions, the following compounds are obtained.

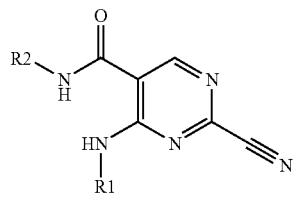
| Example | R1 | R2—NH | MS(M + 1)+ | Rf (solvent) |
|---|---|---|---|---|
| 2 | spiro[2.5]oct-6-yl ethyl | morpholinyl-CH2-CH(NH)-CH2-Ph | 489 | 0.75 (CH2Cl2:MeOH = 10:1) |
| 3 | spiro[2.5]oct-6-yl ethyl | morpholinyl-CH2-CH(NH)-(2-F-Ph) | 493 | 0.58 (CH2Cl2:MeOH = 10:1) |
| 4 | spiro[2.5]oct-6-yl ethyl | 4-Me-piperazinyl-CH2-CH(NH)-Ph | 488 | 0.18 (CH2Cl2:MeOH = 10:1) |
| 5 | spiro[2.5]oct-6-yl ethyl | morpholinyl-CH2-CH2-CH(NH)-Ph | 489 | 0.58 (CH2Cl2:MeOH = 10:1) |
| 6 | spiro[2.5]oct-6-yl ethyl | 4-Me-piperazinyl-CH2-CH(NH)-CH2-Ph | 502 | 0.13 (CH2Cl2:MeOH = 10:1) |

-continued

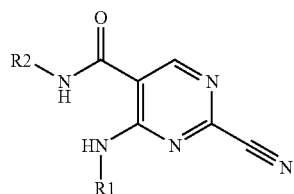

| Example | R1 | R2—NH | MS(M + 1)⁺ | Rf (solvent) |
|---|---|---|---|---|
| 7 | spiro[2.5]octyl-ethyl | 1-phenyl-2-pyrrolidin-1-yl-ethylamine | 459 | 0.48 (CH₂Cl₂:MeOH = 10:1) |
| 8 | spiro[2.5]octyl-ethyl | 1-(3-fluorobenzyl)-2-pyrrolidin-1-yl-ethylamine | 491 | 0.55 (CH₂Cl₂:MeOH = 4:1) |
| 9 | spiro[2.5]octyl-ethyl | 1-(2-methoxybenzyl)-2-pyrrolidin-1-yl-ethylamine | 503 | 0.60 (CH₂Cl₂:MeOH = 4:1) |
| 10 | spiro[2.5]octyl-ethyl | (S)-1-(2-fluorobenzyl)-2-pyrrolidin-1-yl-ethylamine | 491 | 0.28 (CH₂Cl₂:MeOH = 10:1) |
| 11 | spiro[2.5]octyl-ethyl | (S)-1-(thiophen-2-ylmethyl)-2-pyrrolidin-1-yl-ethylamine | 479 | 0.23 (CH₂Cl₂:MeOH = 10:1) |

-continued
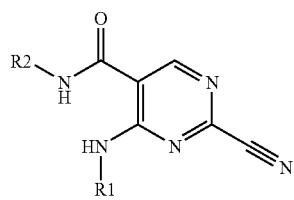
| Example | R1 | R2—NH | MS(M + 1)+ | Rf (solvent) |
|---|---|---|---|---|
| 12 | (spiro[2.5]octyl-ethyl) | (1-pyrrolidinyl-CH2-CH(NH)-CH2-2-pyridyl) | 474 | 0.30 (CH2Cl2:MeOH = 10:1) |
| 13 | (spiro[2.5]octyl-ethyl) | (1-pyrrolidinyl-CH2-CH(NH)-CH2-3-thienyl) | 479 | 0.15 (CH2Cl2:MeOH = 10:1) |
| 14 | (spiro[2.5]octyl-ethyl) | (1-pyrrolidinyl-CH2-CH(NH)-CH2-2-furyl) | 463 | 0.25 (CH2Cl2:MeOH = 10:1) |
| 15 | (spiro[2.5]octyl-ethyl) | (N-cyclopropyl-N-ethyl-aminomethyl-CH(NH)-CH2-phenyl) | 487 | 0.63 (CH2Cl2:MeOH = 10:1) |

-continued
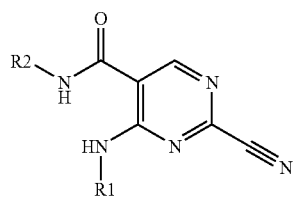
| Example | R1 | R2—NH | MS(M + 1)+ | Rf (solvent) |
|---|---|---|---|---|
| 16 | | | 473 | 0.52 (CH$_2$Cl$_2$:MeOH = 8:1) |
| 17 | | | 473 | 0.52 (CH$_2$Cl$_2$:MeOH = 8:1) |
| 18 | | | 523 | 0.70 (CH$_2$Cl$_2$:MeOH = 8:1) |
| 19 | | | 564 | 0.73 (CH$_2$Cl$_2$:MeOH = 8:1) |

-continued
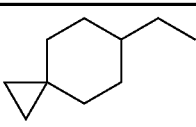
| Example | R1 | R2—NH | MS(M + 1)+ | Rf (solvent) |
|---|---|---|---|---|
| 20 | 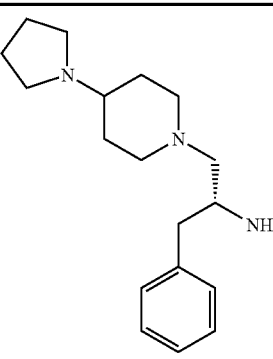 | 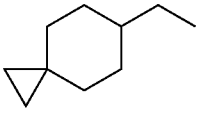 | 556 | 0.20 (CH$_2$Cl$_2$:MeOH = 8:1) |
| 21 | 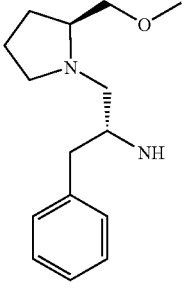 | 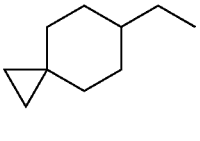 | 517 | 0.60 (CH$_2$Cl$_2$:MeOH = 8:1) |
| 22 | 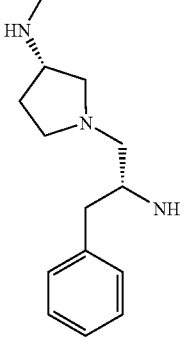 | 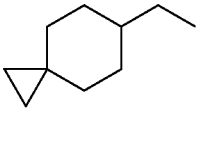 | 516 | 0.23 (CH$_2$Cl$_2$:MeOH = 8:1) |
| 23 | 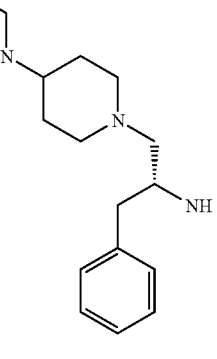 | | 506 | 0.62 (CH$_2$Cl$_2$:MeOH = 8:1) |

-continued
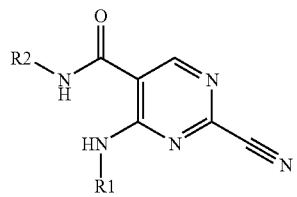
| Example | R1 | R2—NH | MS(M + 1)+ | Rf (solvent) |
|---|---|---|---|---|
| 24 | spiro[2.5]octyl-ethyl | 1-pyrrolidinyl-neopentyl-phenyl-NH | 501 | 0.53 (CH$_2$Cl$_2$:MeOH = 8:1) |
| 25 | spiro[2.5]octyl-ethyl | azepan-1-yl-benzyl-NH | 501 | 0.57 (CH$_2$Cl$_2$:MeOH = 8:1) |
| 26 | spiro[2.5]octyl-ethyl | 3,3-dimethylazetidinyl-benzyl-NH | 487 | 0.57 (CH$_2$Cl$_2$:MeOH = 8:1) |
| 27 | spiro[2.5]octyl-ethyl | 2-azabicyclo[2.2.1]heptyl-benzyl-NH | 499 | 0.45 (CH$_2$Cl$_2$:MeOH = 8:1) |

-continued

| Example | R1 | R2—NH | MS(M + 1)+ | Rf (solvent) |
|---|---|---|---|---|
| 28 | spiro[3.5]nonane-ethyl | 2-benzyl-1-pyrrolidin-1-yl-propyl amine | 487 | 0.40 (CH₂Cl₂:MeOH = 5:1) |
| 29 | spiro[2.5]octane-ethyl | 1-(2-methoxymethyl-pyrrolidin-1-yl)-3-phenyl-propan-2-yl amine | 517 | $^1$H NMR (CDCl$_3$), δ 0.17-0.30 (4H, m), 0.90-0.94 (2H, m), 1.13-1.28 (2H, m), 1.42-1.50 (1H, m), 1.57-1.89 (10H, m), 2.50-2.57 (1H, m), 2.70 (1H, dd), 2.81-2.93 (3H, m), 3.05 (1H, dd), 3.15-3.20 (1H, m), 3.28 (3H, s), 3.40 (2H, t), 4.29-4.37 (1H, m), 7.19-7.31 (5H, m), 7.65 (1H, d), 8.34 (1H, s), 8.94 (1H, t) |
| 30 | spiro[2.5]octane-ethyl | 2-morpholin-4-yl-benzyl amine | 461 | 0.45 (n-hexane:AcOEt = 1:1) |
| 31 | spiro[2.5]octane-ethyl | 1-methyl-4-phenyl-piperidin-4-yl amine | 459 | $^1$H NMR (CDCl$_3$), δ 0.14-0.18 (2H, m), 0.24-0.28 (2H, m), 0.85-0.89 (2H, m), 1.06-1.16 (2H, m), 1.54-1.70 (5H, m), 2.28 (4H, d), 2.35 (3H, s), 2.43-2.45 (2H, m), 2.83-2.85 (2H, m), 3.34 (2H, t), 6.22 (1H, s), 7.25-7.29 (1H, m), 7.34-7.42 (4H, m), 8.45 (1H, s), 8.57 (1H, br) |
| 32 | spiro[2.5]octane-ethyl | 1-phenyl-4-pyrrolidin-1-yl-butan-2-yl amine | 488 | 0.33 (CH₂Cl₂:MeOH = 10:1) |

-continued

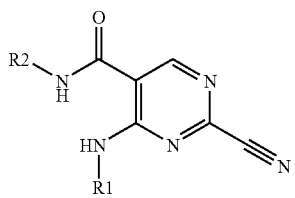

| Example | R1 | R2—NH | MS(M + 1)+ | Rf (solvent) |
|---|---|---|---|---|
| 33 | spiro[2.5]octyl-ethyl | 4,5-dimethoxy-2-phenyl-anilino | | 0.15 (n-hexane:AcOEt = 3:1) |
| 34 | spiro[2.5]octyl-ethyl | 1-methyl-4-phenyl-1H-pyrazol-3-ylamino | 442 | 0.25 (n-hexane:AcOEt = 1:1) |
| 35 | spiro[2.5]octyl-ethyl | 2-phenyl-2-(pyrrolidin-1-yl)ethylamino | 459 | 0.54 (CH$_2$Cl$_2$:MeOH = 9:1) |
| 36 | spiro[2.5]octyl-ethyl | 1-benzyl-2-(3,3-difluoropiperidin-1-yl)ethylamino | 523 | 0.65 (n-hexane:AcOEt = 1:1) |
| 37 | spiro[2.5]octyl-ethyl | 2-phenyl-3-(pyrrolidin-1-yl)propylamino | 473 | 0.32 (CH$_2$Cl$_2$:MeOH = 9:1) |

-continued
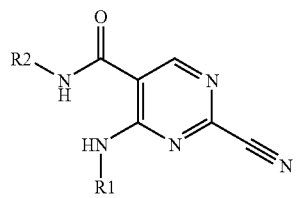
| Example | R1 | R2—NH | MS(M + 1)+ | Rf (solvent) |
|---|---|---|---|---|
| 38 | spiro[2.5]oct-6-yl ethyl | 4-methylpiperazinyl-CH(Ph)-CH2-NH | 488 | 0.22 (CH2Cl2:MeOH = 9:1) |
| 39 | spiro[2.5]oct-6-yl ethyl | morpholinyl-CH(Ph)-CH2-NH | 475 | 0.66 (CH2Cl2:MeOH = 9:1) |
| 40 | spiro[2.5]oct-6-yl ethyl | piperidinyl-CH(Ph)-CH2-NH | 473 | 0.47 (CH2Cl2:MeOH = 9:1) |
| 41 | spiro[2.5]oct-6-yl ethyl | 4-piperidinyl-piperidinyl-CH2-CH(CH2Ph)-NH | 570 | 0.12 (CH2Cl2:MeOH = 9:1) |
| 42 | spiro[2.5]oct-6-yl ethyl | (3R)-3-methoxypyrrolidinyl-CH2-CH(CH2Ph)-NH | 503 | 0.53 (CH2Cl2:MeOH = 9:1) |

-continued

| Example | R1 | R2—NH | MS(M + 1)+ | Rf (solvent) |
|---------|----|----|----|----|
| 43 | spiro[2.5]oct-6-yl-ethyl | 2-oxa-8-azaspiro[4.5]decane-CH2-CH(NH)-CH2-Ph | 543 | 0.49 (CH2Cl2:MeOH = 9:1) |
| 44 | spiro[2.5]oct-6-yl-ethyl | t-amyl-NH-CH2-CH(NH)-CH2-Ph | 489 | 0.47 (CH2Cl2:MeOH = 9:1) |
| 45 | spiro[2.5]oct-6-yl-ethyl | cyclopentyl-NH-CH2-CH(NH)-CH2-Ph | 487 | 0.30 (CH2Cl2:MeOH = 9:1) |
| 46 | spiro[2.5]oct-6-yl-ethyl | N-methyl-N-isopropyl-CH2-CH(NH)-CH2-Ph | 475 | 0.32 (CH2Cl2:MeOH = 9:1) |
| 47 | spiro[2.5]oct-6-yl-ethyl | pyrrolidin-1-yl-CH2-C(CH3)(NH)-CH2-Ph | 487 | 0.31 (CH2Cl2:MeOH = 9:1) |

-continued
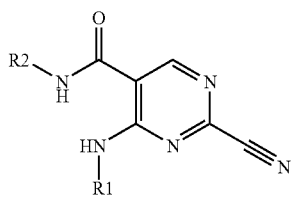
| Example | R1 | R2—NH | MS(M + 1)+ | Rf (solvent) |
|---|---|---|---|---|
| 48 | | | 501 | 0.49 (CH$_2$Cl$_2$:MeOH = 9:1) |
| 49 | | | 529 | 0.41 (n-hexane:AcOEt = 1:1) |
| 50 | | | 501 | 0.56 (n-hexane:AcOEt = 1:1) |
| 51 | | | 529 | 0.46 (CH$_2$Cl$_2$:MeOH = 9:1) |
| 52 | | | 491 | 0.18 (CH$_2$Cl$_2$:MeOH = 9:1) |

-continued

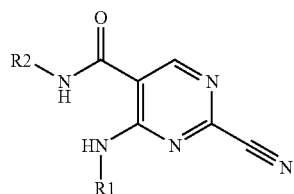

| Example | R1 | R2—NH | MS(M + 1)+ | Rf (solvent) |
|---|---|---|---|---|
| 53 | spiro[2.5]oct-6-yl-ethyl | 1-methyl-4-(2-chloro-6-fluorophenyl)piperidin-4-ylmethylamino | 525, 527 | 0.11 (CH₂Cl₂:MeOH = 9:1) |
| 54 | spiro[2.5]oct-6-yl-ethyl | 1-methyl-4-(2-trifluoromethylphenyl)piperidin-4-ylmethylamino | 541 | 0.12 (CH₂Cl₂:MeOH = 9:1) |
| 55 | spiro[2.5]oct-6-yl-ethyl | 1-(2-hydroxyethyl)-4-phenylpiperidin-4-ylmethylamino | 503 | 0.08 (CH₂Cl₂:MeOH = 9:1) |
| 56 | spiro[2.5]oct-6-yl-ethyl | 1-(2,2-difluoroethyl)-4-phenylpiperidin-4-ylmethylamino | 523 | 0.20 (n-hexane:AcOEt = 1:1) |
| 57 | spiro[2.5]oct-6-yl-ethyl | 1-cyclopentyl-4-phenylpiperidin-4-ylmethylamino | 527 | 0.37 (CH₂Cl₂:MeOH = 9:1) |

Example 58

2-Cyano-4-[(spiro[2.5]oct-6-ylmethyl)amino]pyrimidine-5-carboxylic acid [5-(1-methylpiperidin-4-yloxy)biphenyl-2-yl]amide To a solution of 5-(1-methylpiperidin-4-yloxy)biphenyl-2-ylamine (0.27 mmol, step 58.2) and 2-cyano-4-[(spiro[2.5]oct-6-ylmethyl)amino]pyrimidine-5-carboxylic acid (0.33 mmol) in DMF (2 mL) are added EDCI-HCl (0.54 mmol) and HOAt (0.54 mmol) at 0° C. After stirring at the ambient temperature overnight, the reaction mixture is purified by RP-HPLC to give the title compound as a white solid; $^1$H NMR (CDCl$_3$), δ 0.18-0.21 (2H, m), 0.27-0.30 (2H, m), 0.90-0.94 (2H, m), 1.14-1.25 (2H, m), 1.58-1.78 (5H, m), 1.85-1.92 (2H, m), 2.02-2.06 (2H, m), 2.32 (3H, s), 2.70 (2H, br s), 3.41-3.44 (2H, t), 4.35 (1H, m), 6.89 (1H, d), 6.97 (1H, dd), 7.35-7.37 (2H, m), 7.45-7.52 (3H, m), 7.65 (1H, s), 7.92 (1H, s), 8.06 (1H, d), 8.90 (1H, s).

Step 58.1: 5-Fluoro-2-nitrobiphenyl

To a solution of 5-fluoro-2-nitrophenol (10.0 mmol) and triethylamine (12.0 mmol) in CH$_2$Cl$_2$ (100 mL) is added trifluoromethanesulfonic acid anhydride (11.0 mmol) at 0° C. After stirring at the same temperature for 0.5 h under N$_2$, the reaction mixture is diluted with H$_2$O. The mixture is extracted with CH$_2$Cl$_2$ and AcOEt, respectively (×2). The combined organic extracts are dried over Na$_2$SO$_4$, filtered through a short pad of celite and silica gel, washed with AcOEt. The filtrate is concentrated in vacuo to give trifluoromethanesulfonic acid 5-fluoro-2-nitrophenyl ester as a yellow oil.

To a solution of trifluoromethanesulfonic acid 5-fluoro-2-nitrophenyl ester (4.0 mmol) in DME (10 mL) are added phenylboronic acid (4.8 mmol), Pd(PPh$_3$)$_4$ (0.4 mmol), and K$_3$PO$_4$ (3.2 mmol) at room temperature. After stirring at 80° C. for 6 h, the reaction mixture is filtered through celite, and the filter cake is washed with AcOEt. The filtrate is diluted with water and extracted with ether (×2). The combined organic extracts are dried over Na$_2$SO$_4$, filtered, and concentrated in vacuo. The residue is purified by silica gel column chromatography (n-hexane:AcOEt=6:1) to give the title compound; $^1$H NMR (CDCl$_3$), δ 7.12-7.19 (2H, m), 7.29-7.32 (2H, m), 7.42-7.45 (3H, t), 7.94 (1H, dd).

Step 58.2: 5-(1-Methylpiperidin-4-yloxy)biphenyl-2-ylamine

To a solution of 5-fluoro-2-nitrobiphenyl (0.86 mmol) in toluene/aq.KOH (2 mL/2 mL) are added 1-methylpiperidin-4-ol (1.1 mmol) and TBAB (0.17 mmol) at room temperature. After stirred at 70° C. overnight, the reaction mixture is diluted with AcOEt and water, and extracted with AcOEt (×2). The combined organic extracts are dried over Na$_2$SO$_4$, filtered, and concentrated in vacuo. The residue is purified by silica gel column chromatography (CH$_2$Cl$_2$:MeOH=10:1) to give 1-methyl-4-(6-nitrobiphenyl-3-yloxy)piperidine as a yellow solid. To a solution of 1-methyl-4-(6-nitrobiphenyl-3-yloxy)piperidine (0.63 mmol) in EtOH (5 mL) is added 5% palladium on activated carbon (50 mg) under N$_2$ atmosphere. The reaction mixture is vigorously stirred at room temperature for 2.5 h under H$_2$, and then filtered through celite (linsed with AcOEt). The filtrate is concentrated in vacuo to the title compound as a brown oil; $^1$H NMR (CDCl$_3$), δ 1.79-1.87 (2H, m), 1.96-2.01 (2H, m), 2.25-2.31 (2H, m), 2.29 (3H, s), 2.70 (2H, brs), 3.52 (2H, m), 4.15-4.18 (1H, m), 6.70 (1H, d), 6.76-6.80 (2H, m), 7.32-7.38 (1H, m), 7.42-7.45 (4H, m).

Examples 59 to 65

By repeating the procedures described above using appropriate starting materials and conditions, the following compounds are obtained.

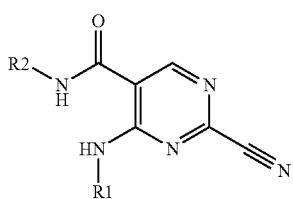

| Example | R1 | R2—NH | MS (M + 1)$^+$ | Rf (solvent) |
|---------|----|----|----|----|
| 59 | spiro[2.5]octylmethyl | biphenyl-ether-ethoxy-NH | 512 | 0.47 (n-hexane:AcOEt = 1:1) |

-continued
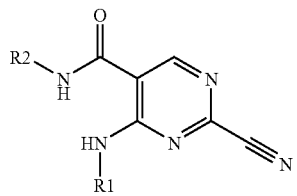
| Example | R1 | R2—NH | MS (M + 1)+ | Rf (solvent) |
|---|---|---|---|---|
| 60 | spiro[2.5]octyl-ethyl | 2-(dimethylamino)ethoxy-biphenyl-NH | 525 | 0.27 (CH$_2$Cl$_2$:MeOH = 10:1) |
| 61 | spiro[2.5]octyl-ethyl | (1-methylpiperidin-4-yl)methoxy-biphenyl-NH | 565 | 0.35 (CH$_2$Cl$_2$:MeOH = 5:1) |
| 62 | spiro[2.5]octyl-ethyl | (4-methylpiperazin-1-yl)-biphenyl-NH | 536 | 0.45 (CH$_2$Cl$_2$:MeOH = 10:1) |

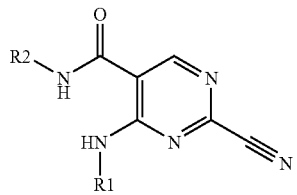

| Example | R1 | R2—NH | MS (M + 1)+ | Rf (solvent) |
|---|---|---|---|---|
| 63 | | | 581 | 0.20 (CH$_2$Cl$_2$:MeOH = 10:1) |
| 64 | | | 565 | 0.18 (CH$_2$Cl$_2$:MeOH = 4:1) |
| 65 | | | 559 | 0.23 (CH$_2$Cl$_2$:MeOH = 9:1) |

Example 66

2-cyano-4-[(spiro[2.5]oct-6-ylmethyl)amino]pyrimidine-5-carboxylic acid (4-benzyl-1-isopropylpiperidin-4-yl)amide To a solution of the 4-amino-4-benzylpiperidine-1-carboxylic acid tert-butyl ester (0.38 mmol, step 66.1) and 2-cyano-4-[(spiro[2.5]oct-6-ylmethyl)amino]pyrimidine-5-carboxylic acid (0.38 mmol) in DMF (1.3 mL) are added HOAt (0.51 mmol) and EDCI-HCl (0.51 mmol) at 0° C. After warming to room temperature and stirring for 15 h, the reaction mixture is diluted with AcOEt and washed with 1N aq. KHSO$_4$, sat. aq. NaHCO$_3$, and brine. The organic layer is dried over MgSO$_4$, filtered, and concentrated in vacuo. The residue is purified by silica gel column chromatography to give 4-benzyl-4-({2-cyano-4-[(spiro[2.5]oct-6-ylmethyl)-amino]-pyrimidine-5-carbonyl}amino)piperidine-1-carboxylic acid tert-butyl ester.

To a solution of 4-benzyl-4-({2-cyano-4-[(spiro[2.5]oct-6-ylmethyl)amino]-pyrimidine-5-carbonyl}amino)piperidine-1-carboxylic acid tert-butyl ester (0.14 mmol) in CH$_2$Cl$_2$ (1.5 mL) is added TFA (0.4 mL) at 0° C. After stirring at room temperature for 0.5 h, the reaction mixture is concentrated in vacuo. The residue is dissolved in DMF (1.5 mL) and treated with K$_2$CO$_3$ (0.35 mmol) and isopropyl iodide (0.28 mmol) at 0° C. After stirring at room temperature for 5 h, the reaction mixture is diluted with AcOEt and washed with H$_2$O and brine. The organic layer is dried over Na$_2$SO$_4$, filtered, and concentrated in vacuo. The residue is purified by RP-HPLC to give the title compound; $^1$H NMR (CDCl$_3$), δ: 0.18-0.26 (2H, m), 0.27-0.34 (2H, m), 0.91-0.99 (2H, m), 1.01-1.13 (6H, s), 1.17-1.33 (2H, m), 1.63-1.97 (7H, m), 2.15-2.40 (4H, m), 2.64-2.90 (3H, m), 3.15 (2H, s), 3.46 (2H, dd), 5.28 (1H, s), 7.02-7.10 (2H, m), 7.20-7.30 (3H, m), 8.05 (1H, s), 8.70 (1H, bs).

Step 66.1:
4-Amino-4-benzyl-piperidine-1-carboxylic acid tert-butyl ester To a solution of 4-benzyl-piperidine-1,4-dicarboxylic acid mono-tert-butyl ester (0.65 mmol) in 1,4-dioxane (2 mL) are added Et$_3$N (0.71 mmol) and DPPA (0.71 mmol) at room temperature. After warming to 100° C. and stirring for 2 h, the reaction mixture is diluted with AcOEt. The organic layer is washed with sat. aq. NaHCO$_3$ and brine, dried over MgSO$_4$, filtered, and concentrated in vacuo. The residue is dissolved in THF (4 mL) and 6N aq. NaOH (0.22 mL) is added at room temperature. After stirring for 4 h, the reaction mixture is diluted with CH$_2$Cl$_2$, washed with brine, dried over MgSO$_4$, filtered, and concentrated in vacuo. The residue is purified by silica gel column chromatography to give the title compound; $^1$H NMR (CDCl$_3$), δ: 1.18 (2H, bs), 1.28-1.37 (2H, m), 1.46 (9H, s), 1.51-1.64 (2H, m), 2.66 (2H, s), 3.20 (2H, dd), 3.74 (2H, bd), 7.13-7.19 (2H, m), 7.21-7.34 (3H, m).

Examples 67 to 72

By repeating the procedures described above using appropriate starting materials and conditions, the following compounds are obtained.

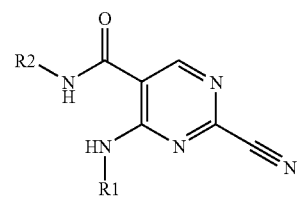

| Example | R1 | R2—NH | MS (M + 1)$^+$ | Rf (solvent) |
|---|---|---|---|---|
| 67 | spiro[2.5]oct-6-ylethyl | 1-methyl-4-benzyl-piperidin-4-ylamine | 473 | $^1$H NMR (CDCl$_3$), δ 0.19-0.23 (2 H, m), 0.28-0.32 (2 H, m), 0.93-0.96 (2 H, m), 1.19-1.29 (2 H, m), 1.67-1.88 (7 H, m), 2.12 (2 H, t), 2.21 (2 H, d), 2.29 (3 H, s), 2.72 (2 H, d), 3.15 (2 H, s), 3.46 (2 H, t), 5.27 (1 H, s), 7.05-7.07 (2 H, m), 7.22-7.24 (3 H, m), 8.06 (1 H, s), 8.70 (1 H, br). |
| 68 | spiro[2.5]oct-6-ylethyl | 1-methyl-4-(2-fluorobenzyl)-piperidin-4-ylamine | 491 | 0.17 (CH$_2$Cl$_2$:MeOH = 8:1) |
| 69 | spiro[2.5]oct-6-ylethyl | 1-methyl-4-(4-chlorobenzyl)-piperidin-4-ylamine | 508 | 0.33 (CH$_2$Cl$_2$:MeOH = 8:1) |

-continued

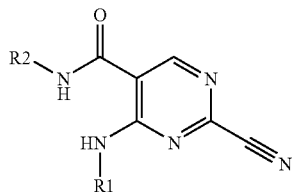

| Example | R1 | R2—NH | MS (M + 1)⁺ | Rf (solvent) |
|---|---|---|---|---|
| 70 | spiro[2.5]oct-6-ylmethyl | 1-cyclopentyl-4-benzyl-piperidin-4-yl-amino | 527 | 0.55 (CH₂Cl₂:MeOH = 8:1) |
| 71 | spiro[2.5]oct-6-ylethyl | 1-(pentan-3-yl)-4-benzyl-piperidin-4-yl-amino | 529 | 0.55 (CH₂Cl₂:MeOH = 8:1) |
| 72 | spiro[2.5]oct-6-ylmethyl | 1-methyl-3-benzyl-piperidin-3-yl-amino | 473 | 0.60 (CH₂Cl₂:MeOH = 8:1) |

Example 73

(R)-2-Cyano-4-(methylspiro[2.5]oct-6-ylmethylamino)pyrimidine-5-carboxylic acid (2-phenyl-1-pyrrolidin-1-ylmethylethyl)amide To a solution of the crude 2-cyano-4-(methylspiro[2.5]oct-6-ylmethylamino)pyrimidine-5-carboxylic acid (82 mg, step 73.4) in DMF (1.5 mL) are added (R)-2-phenyl-1-pyrrolidin-1-ylmethylethylamine (0.3 mmol), EDCI-HCl (0.4 mmol), and HOAt (0.4 mmol) at room temperature. The reaction mixture is stirred for 24 h and the reaction is quenched by the addition of water. The mixture is extracted with AcOEt and the organic extracts are dried over Na₂SO₄, filtered, concentrated in vacuo. The resulting residue is purified by RP-HPLC to give the title compound; MS (M+1)⁺ 488, Rf (solvent) 0.13 (CH₂Cl₂:MeOH=10:1).

Step. 73.1: 2,4-Dichloropyrimidine-5-carboxylic acid allyl ester

To a solution of the 2,4-dichloropyrimidine-5-carbonyl chlorode (5.1 mmol) in THF (10 mL) are added allyl alcohol (5.1 mmol) and DIEA (N,N-diisopropylethylamine) (6.1 mmol) at 0° C. After stirring at 0° C. for 3.5 h, the reaction mixture is filtered and the filtrate is concentrated in vacuo. The resulting residue is purified by silica gel column chromatography to give the title compound; ¹H NMR (CDCl₃) δ 4.87-4.89 (m, 2H), 5.35-5.48 (m, 2H), 5.97-6.08 (M, 1H), 9.05 (s, 1H).

Step 73.2: 2-Chloro-4-(methylspiro[2.5]oct-6-ylm-ethylamino)pyrimidine-5-carboxylic acid allyl ester To a solution of the 2,4-dichloropyrimidine-5-carboxylic acid allyl ester (1.6 mmol) in dioxane (6 mL) is added $Et_3N$ (2.4 mmol) at room temperature. A solution of methyl-spiro[2.5]oct-6-ylmethylamine (1.6 mmol) in dioxane (2.0 mL) is added dropwise to the reaction mixture. The reaction mixture is stirred at room temperature for 12 h and the reaction is quenched by the addition of water. The mixture is extracted with $CH_2Cl_2$. The organic extracts are dried over $Na_2SO_4$, filtered, and concentrated in vacuo. The resulting residue is purified by silica gel column chromatography to give the title compound (370 mg); $^1H$ NMR ($CDCl_3$) δ 0.15-0.19 (m, 2H), 0.25-0.29 (m, 2H), 0.87-0.91 (m, 2H), 1.08-1.20 (m, 2H), 1.60-1.85 (m, 5H), 2.95 (s, 3H), 3.59 (d, 2H), 4.77-4.78 (m, 2H), 5.29-6.08 (m, 1H), 8.48 (s, 1H).

Step 73.3: 2-Cyano-4-(methylspiro[2.5]oct-6-ylm-ethylamino)pyrimidine-5-carboxylic acid allyl ester To a solution of the 2-chloro-4-(methylspiro[2.5]oct-6-yl-methylamino)pyrimidine-5-carboxylic acid allyl ester (1.1 mmol) in DMSO (2.0 mL) are added KCN (1.6 mmol), DABCO (0.3 mmol), and $H_2O$ (0.2 mL) at room temperature. The reaction mixture is stirred at room temperature for 3 h and the reaction is quenched by the addition of water. The mixture is extracted with AcOEt. The organic extracts are washed with brine, dried over $Na_2SO_4$, filtered, and concentrated in vacuo. The resulting residue is purified by silica gel column chromatography to give the title compound.

Step 73.4: 2-Cyano-4-(methylspiro[2.5]oct-6-ylm-ethylamino)pyrimidine-5-carboxylic acid To a solution of a 2-cyamo-4-(methylspiro[2.5]oct-6-ylm-ethylamino)pyrimidine-5-carboxylic acid allyl ester (0.87 mmol) in THF (8.7 mL) are added $Pd(PPh_3)_4$ (0.087 mmol) and morphorine (1.7 mmol) at room temperature. The reaction mixture is stirred at room temperature for 0.5 h, and the reaction is quenched by the addition of water and sat aq $NaHCO_3$. The mixture is washed with ether. The aqueous layer is acidified to pH 2 with sat. aq $KHSO_4$. The mixture is extracted with AcOEt. The organic extracts are washed with brine, dried over $Na_2SO_4$, filtered, and concentrated in vacuo to give the title compound.

Example 74

(R)-2-Cyano-4-(spiro[2.5]oct-6-ylmethyl)pyrimi-dine-5-carboxylic acid (2-phenyl 1-pyrrolidin-1-ylmethylethyl)amide To a solution of the crude 2-cyano-4-(spiro[2.5]oct-6-ylm-ethyl)pyrimidine-5-carboxylic acid (22 mg, step 74.5) in DMF (1.5 mL) are added (R)-2-phenyl-1-pyrrolidin-1-ylm-ethylethylamine (0.083 mmol), EDCl—$H_2O$ (0.11 mmol), and HOAt (0.11 mmol) at room temperature. The reaction mixture is stirred for 24 h and the reaction is quenched by the addition of $H_2O$. The mixture is extracted with AcOEt, and the organic extracts are dried over $Na_2SO_4$, filtered, and concentrated in vacuo. The resulting residue is purified by RP-HPLC to give the title compound; MS (M+1)$^+$: 474, Rf (solvent): 0.63 ($CH_2Cl_2$:MeOH=10:1).

Step 74.1: 2,4-Dichloroprimidine-5-carboxylic acid

To a solution of the 2,4-dichloropyrimidine-5-carbonyl chloride (24 mmol) in THF (24 mL) is added $H_2O$ (0.64 mL) at room temperature. The reaction mixture is stirred at room temperature for 0.83 h and then diluted with $H_2O$. The mixture is extracted with AcOEt. The organic extracts are washed with brine, dried over $Na_2SO_4$, filtered, and concentrated in vacuo to give the crude titled compound; $^1H$ NMR ($CDCl_3$) δ 6.80 (brs, 1H), 9.18 (s, 1H).

Step 74.2: 2-Chloro-4-(spiro[2.5]oct-6-ylmethoxy)pyrimidine-5-carboxylic acid To a solution of a 2,4-dichloroprimidine-5-carboxylic acid (440 mg) in THF (4.0 mL) are added t-BuOK (potassium tert-butoxide) (5.7 mmol) and spiro[2.5]oct-6-ylmethanol (2.3 mmol) in THF (1.0 mL) at 0° C. After stirring at 0° C. for 1.5 h, the reaction is quenched by the addition of sat. aq. $NaHCO_3$. The mixture is washed with ether. The aqueous layer is acidified to pH 2 with sat. aq. $KHSO_4$, then extracted with AcOEt. The organic extracts are washed with brine, dried over $Na_2SO_4$, filtered, and concentrated in vacuo to give the crude title compound.

Step 74.3: 2-Chloro-4-(spiro[2.5]oct-6-ylmethoxy)pyrimidine-5-carboxylic acid allyl ester To a solution of the 2-chloro-4-(spiro[2.5]oct-6-yl-methoxy)pyrimidine-5-carboxylic acid (490 mg) in DMF (2.9 mL) are added $K_2CO_3$ (4.4 mmol) and allyl bromide (7.4 mmol) at room temperature. After stirring at 50° C. for 0.5 h, the reaction mixture is cooling and diluted with $H_2O$. The mixture is extracted with AcOEt. The organic extracts are washed with brine, dried over $Na_2SO_4$, filtered, and concentrated in vacuo. The resulting residue is purified by silica gel column chromatography to give a crude title compound.

Step 74.4: 2-Cyano-4-(spiro[2.5]oct-6-ylmethoxy)pyrimidine-5-carboxylic acid allyl ester To a solution of the 2-chloro-4-(spiro[2.5]oct-6-yl-methoxy)pyrimidine-5-carboxylic acid allyl ester (0.62 mmol) in DMSO (1.0 mL) are added KCN (0.94 mmol), DABCO (0.19 mmol), and $H_2O$ (0.10 mL) at room temperature. The reaction mixture is stirred at room temperature for 0.5 h and the reaction is quenched by the addition of water. The mixture is extracted with AcOEt. The organic extracts are washed with brine, dried over $Na_2SO_4$, filtered, and concentrated in vacuo. The resulting residue is purified by silica gel column chromatography to give the titled compound; $^1H$ NMR ($CDCl_3$) δ 0.19-0.20 (m, 2H), 0.21-0.33 (m, 2H), 0.91-0.96 (m, 2H), 1.23-1.33 (m, 3H), 1.72-1.85 (m, 4H), 4.38 (d, 2H), 4.84 (d, 2H), 5.31-5.45 (m, 1H), 9.01 (s, 1H).

Step 74.5: 2-Cyano-4-(spiro[2.5]oct-6-ylmethoxy)pyrimidine-5-carboxylic acid To a solution of a 2-cyano-4-(spiro[2.5]oct-6-ylmethoxy)pyrimidine-5-carboxylic acid allyl ester (0.096 mmol) in THF (1.0 mL) are added $Pd(PPh_3)_4$ (tetrakis(triphenylphosphine)palladium) (0.0096 mmol) and morpholine (0.19 mmol) at room temperature. The reaction mixture is stirred at room temperature for 0.5 h and the reaction is quenched by the addition of sat. aq. $NaHCO_3$. The mixture is extracted with ether. The aqueous layer is acidified to pH 2 with sat. aq. $KHSO_4$. The mixture is extracted with AcOEt. The organic extracts are washed with brine, dried over $Na_2SO_4$, filtered, and concentrated in vacuo to give the crude titled compound.

Example 75

2-Cyano-4-[2-(1-methylpiperidin-4-yl)ethoxy]-6-[(spiro[3.5]non-7-yl-methyl)amino]pyrimidine-5-carboxylic acid methylamide To a solution of 4[2-(1-tert-butoxycarbonylpiperidin-4-yl)ethoxy]-2-cyano-6-[(spiro[3.5]non-7-ylmethyl)amino]pyrimidine-5-carboxylic acid (0.23 mmol, step 75.4) and 2 M methyl amine solution (0.30 mmol) in DMF (1 mL) are added EDCI-HCl (0.34 mmol) and HoAt (0.34 mmol) at 0° C. The reaction mixture is stirred at room temperature for 1 h. After dilution with AcOEt, the mixture is washed with $H_2O$ and brine. The organic layer is dried over $MgSO_4$, filtered, and concentrated. The residue is purified by silicagel column chromatography to give 4-(2-{2-cyano-5-methylcarbamoyl-6-[(spiro[3.5]non-7-ylmethyl)amino]-pyrimidin-4-yloxy}ethyl)piperidine-1-carboxylic acid tert-butyl ester as a white solid; $^1$H-NMR (CDCl$_3$), δ: 0.98-1.07 (2H, m), 1.14-1.85 (2H, m), 1.46 (9H, s), 2.70 (2H, t), 2.93 (3H, d), 3.33 (2H, t), 4.05-4.15 (2H, m), 4.54 (2H, t), 7.80-7.85 (1H, m), 10.10-10.15 (1H, m).

To a solution of 4-(2-{2-cyano-5-methylcarbamoyl-6-[(spiro[3.5]non-7-yl-methyl)amino]-pyrimidin-4-yloxy}ethyl)piperidine-1-carboxylic acid tert-butyl esterther (0.25 mmol) in $CH_2Cl_2$ (3 mL) is added TFA (0.70 mL) at room temperature. After stirring at the same temperature for 0.5 h, the reaction mixture is evaporated in vacuo, which is directly used for the next reaction. To a solution of the crude product in THF (5 mL) is added aq. HCHO (0.10 mL) at room temperature. After stirring at the same temperature for 0.5 h, 1 M NaBH$_3$CN solution (0.10 mmol) is added to the reaction mixture at 0° C. The reaction mixture is warmed to room temperature and further stirred for 0.5 h. After dilution with AcOEt, the organic layer is washed twice with $H_2O$ and evaporated in vacuo. The residue is purified by RP-HPLC to give a 2-cyano-4-[2-(1-methylpiperidin-4-yl)ethoxy]-6-[(spiro[3.5]non-7-ylmethyl)amino]pyrimidine-5-carboxylic acid methylamide (NVP-TAF059) as a white solid, $^1$H-NMR (CDCl$_3$), δ: 0.97-1.07 (2H, m), 1.19-1.26 (2H, m), 1.43-1.88 (18H, m), 2.14-2.17 (2H, m), 2.42 (3H, S), 2.93 (3H, d), 3.05-3.08 (2H, m), 3.32 (2H, t), 4.54 (2H, t), 7.81 (1H, br d), 10.14 (1H, brt).

Step 75.1: 4-[2-(1-tert-Butoxycarbonylpiperidin-4-yl)ethoxy]-6-chloro-2-methylthiopyrimidine-5-carboxylic acid allyl ester To a mixture of NaH (9.0 mmol) and N—BOC4-piperidine ethanol (4.9 mmol) in dry THF (15 mL) is added dropwise a solution of 4,6-dichloropyrimidine-2-methylthio-5-carboxylic acid (3.8 mmol) in dry THF at 0° C. and the mixture is stirred at room temperature for 1.5 h. The mixture is diluted with AcOEt, washed with $H_2O$, and brine. The organic layer is dried over $MgSO_4$, filtered, and concentrated to give the adduct product (1.6 g), which is directly used for the next reaction without further purification.

To a solution of the above product (1.5 mmol) in DMF (7 mL) is added allylbromide (7.5 mmol) and $K_2CO_3$ (17.4 mmol) at room temperature. After stirred at 50° C. for 1 h, the mixture is diluted with AcOEt. The organic layer is washed with $H_2O$ and brine. After drying $MgSO_4$, the mixture is filtered, and concentrated under reduced pressure. The residue is directly used for the next reaction. $^1$H-NMR (CDCl$_3$), δ: 1.12-1.73 (9H, m), 1.46 (9H, s), 2.54 (3H, s), 2.67-2.69 (2H, m), 4.08-4.13 (2H, m), 4.47 (2H, t), 4.80 (2H, dt), 5.30 (1H, brd), 5.43 (1H, m), 5.98 (1H, ddt)

Step 75.2: 4-[2-(1-tert-Butoxycarbonylpiperidin-4-yl)ethoxy]6-chloro-2-methane sulfonylpyrimidine-5-carboxylic acid allyl ester Following the synthetic procedure as described in Ref. Example 2, step 2.1, 4-[2-(1-tert-butoxycarbonyl piperidin-4-yl)ethoxy]-2,6-dichloropyrimidine-5-carboxylic acid allyl ester (3.0 mmol) is treated with m-CPBA (8.9 mmol) in $CH_2Cl_2$ (10 mL) at 0° C. After usual work-up, the crude material is purified by silica gel chromatography to give 4-[2-(1-tert-butoxycarbonylpiperidin-4-yl)ethoxy]6-chloro-2-methane sulfonylpyrimidine-5-carboxylic acid allyl ester as colorless oil. $^1$H-NMR (CDCl$_3$), δ: 1.12-1.73 (9H, m), 1.46 (9H, s), 2.67-2.69 (2H, m), 3.20 (3H, s), 4.08-4.11 (2H, m), 4.46 (2H, t), 4.87 (2H, dt), 5.33-5.37 (1H, m), 5.42-5.47 (1H, m), 5.98 (1H, ddt)

Step 75.3: 4-[2-(1-tert-Butoxycarbonylpiperidin-4-yl)ethoxy]-6-chloro-2-cyano pyrimidine-5-carboxylic acid allyl ester Following the synthetic procedure as described in Ref. Example 2, a solution of 4-[2-(1-tert-butoxycarbonylpiperidin-4-yl)ethoxy]6-chloro-2-methanesulfonylpyrimidine-5-carboxylic acid allyl ester (1.8 mmol) in $CH_2Cl_2$ (5 mL) is treated with a solution of NaCN (2.2 mmol) and tetra-n-butylammonium bromide (0.10 mmol) in water (2 mL) for 0.5 h. After usual work-up, the crude material is purified by silica gel chromatography to give 4-[2-(1-tert-butoxycarbonylpiperidin-4-yl)ethoxy]-6-chloro-2-cyanopyrimidine-5-carboxylic acid allyl ester as colorless oil; $^1$H-NMR (CDCl$_3$), δ: 1.12-1.73 (9H, m), 1.48 (9H, s), 2.68 (2H, brt), 4.05-4.09 (2H, m), 4.55 (2H, t), 4.87 (2H, dt), 5.33-5.37 (1H, m), 5.41-5.47 (1H, m), 5.98 (1H, ddt).

Step 75.4: 4-[2-(1-tert-Butoxycarbonylpiperidin-4-yl)ethoxy]2-cyano-6-[(spiro[3.5]non-7-ylmethyl)amino]pyrimidine-5-carboxylic acid To a solution of 4-[2-(1-tert-butoxycarbonylpiperidin-4-yl)ethoxy]-6-chloro-2-cyanopyrimidine-5-carboxylic acid allyl ester (1.1 mmol) and C-Spiro[3.5]non-7-yl-methylamine (1.4 mmol) in $C_2H_5CN$ (10 mL) is added triethylamine (2.8 mmol) at room temperature. After stirring at 80° C. for 1 h, the reaction mixture is cooled to room temperature and diluted with AcOEt. The organic layer is washed with $H_2O$ and aq. $KHSO_4$ and brine. The organic layer is dried over $MgSO_4$ and evaporated in vacuo, which is directly used for the next reaction without further purification. To a solution of the crude 4-[2-(1-tert-butoxy carbonylpiperidin-4-yl)ethoxy]-2-cyano-6-[(spiro[3.5]non-7-ylmethyl)amino]pyrimidine-5-carboxylic acid allyl ester (1.1 mmol) in THF (5 mL) are added morpholine (3.4 mmol) and Pd(PPh$_3$)$_4$ (0.06 mmol) successively. After stirring at the same temperature for 0.5 h, the reaction mixture is diluted with AcOEt. The organic layer is washed with $H_2O$ and evaporated in vacuo. The residue is purified by silica gel column chromatography to give a 4-[2-(1-tert-butoxycarbonylpiperidin-4-yl)ethoxy]2-cyano-6-[(spiro[3.5]non-7-ylmethyl)amino]pyrimidine-5-carboxylic acid as yellow pale solid; $^1$H-NMR (CDCl$_3$), δ: 0.97-1.08 (2H, m), 1.15-1.29 (5H, m), 1.48 (9H, s), 1.48-1.86 (15H, m), 2.69 (2H, t), 3.39 (2H, t), 4.11 (2H, m), 4.66 (2H, t), 9.42 (1H, br t).

Example 76

2-Cyano-4-[2-(1-methylpiperidinyl)ethoxy]-6-[(spiro[2.5]oct-6-ylmethyl)-amino]pyrimidine-5-carboxylic acid benzyl amide To a solution of 4-(2-{5-benzylcarbamoyl-2-cyano-6-[(spiro[2.5]oct-6-ylmethyl)amino]-pyrimidin-4-yloxy}ethyl)piperidine-1-carboxylic acid tert-butyl ester (0.68 mmol) in CH2Cl2 (10 mL) is added TFA (2 mL) at 0° C. After stirring for 2 h at 0° C. under N2 atmosphere, the mixture is concentrated and dried in vacuo to give 2-cyano-4-(2-piperidin-4-yl-ethoxy)-6-[(spiro[2.5]oct-6-ylmethyl)amino]pyrimidine-5-carboxylic acid benzyl amide as a yellow solid. $^1$H-NMR (CDCl$_3$), δ 0.17-0.30 (4H, m), 0.89-0.93 (2H, m), 1.00-1.11 (2H, m), 1.14-1.24 (2H, m), 1.29-1.38 (1H, m), 1.51-1.81 (9H, m), 2.41-2.48 (2H, m), 2.99-3.02 (2H, m), 3.42 (2H, t), 4.45 (2H, t), 4.56 (2H, d), 7.29-7.39 (5H, m), 8.17 (1H, t), 10.16 (1H, t).

To a solution of 2-cyano-4-(2-piperidin-4-yl-ethoxy)-6-[(spiro[2.5]oct-6-ylmethyl)amino]-pyrimidine-5-carboxylic acid benzylamide (0.19 mmol) in THF (2 mL) is added formaldehyde solution (100 μL), and the resulting solution is stirred for 0.5 h at room temperature. After cooled to 0° C., 1 M NaBH$_3$CN solution in THF is added dropwise, and the reaction mixture is stirred for 2 h at room temperature. The reaction is quenched by the addition of H2O, and extracted twice with AcOEt. The organic layer is dried over Na2SO4, filtered, and concentrated. The residue is purified by silica gel column to give 2-cyano-4-[2-(1-methylpiperidin-4-yl)ethoxy]-6-[(spiro[2.5]oct-6-ylmethyl)amino]pyrimidine-5-carboxylic acid benzylamide as a colorless oil; $^1$H-NMR (CDCl$_3$), δ 0.17-0.30 (4H, m), 0.89-0.94 (2H, m), 1.14-1.29 (3H, m), 1.40-1.50 (2H, m), 1.58-1.78 (9H, m), 1.95-2.01 (3H, m), 2.38 (3H, s), 2.95-2.98 (2H, m), 3.42 (2H, t), 4.46 (2H, t), 4.56 (2H, d), 7.31-7.39 (5H, m), 8.13 (1H, t), 10.16 (1H, t).

Step 76.1: 4,6-Dichloro-2-methylsulfanylpyrimidine-5-carboxylic acid benzylamide To a suspension of 4,6-dichloro-2-methylsulfanylpyrimidine-5-carboxylic acid (2.1 mmol) in CH2Cl2 (20 mL) are added oxalyl chloride (4.2 mmol) and one drop of DMF at 0° C. After stirred at room temperature for 3 h under N$_2$ atmosphere, the reaction mixture is concentrated and dried in vacuo, to give 4,6-dichloro-2-methylsulfanylpyrimidine-5-carbonyl chloride as a yellow crystal.

To a solution of 4,6-dichloro-2-methylsulfanylpyrimidine-5-carbonyl chloride in THF (15 mL), triethylamine (2.3 mmol) and benzylamine (2.5 mmol) are added at 0° C. After stirred at room temperature for 2 h, the reaction mixture is diluted with AcOEt and H2O. The mixture is extracted twice with AcOEt. The organic layer is dried over Na2SO4, filtered, and concentrated. The residue is purified by silica gel column chromatography to give 4,6-dichloro-2-methylsulfanylpyrimidine-5-carboxylic acid benzylamide as a white solid. $^1$H-NMR (CDCl$_3$), δ 2.57 (3H, s), 4.66 (2H, d), 6.08 (1H, br s), 7.31-7.35 (2H, m), 7.36-7.38 (3H, m).

Step 76.2: 4-[2-(5-Benzylcarbamoyl-6-chloro-2-methylsulfanylpyrimidin-4-yloxy)ethyl]piperidine-1-carboxylic acid tert-butyl ester To a solution of 4,6-dichloro-2-methylsulfanylpyrimidine-5-carboxylic acid benzylamide (3 mmol) in THF (20 mL) is added KO$^t$Bu (3.6 mmol) at 0° C. under N2. After stirred at 0° C. for 20 min, the above mixture is added dropwise to a solution of 4-(2-hydroxyethyl)piperidine-1-carboxylic acid tert-butyl ester (3.3 mmol) in THF (20 mL) at −78° C. The resulting mixture is gradually warm up to −30° C. over 2.5 h. The reaction is quenched by the addition of H2O. The mixture is extracted twice with AcOEt. The organic layer is dried over Na$_2$SO$_4$, filtered, and concentrated to give 4-[2-(5-benzylcarbamoyl-6-chloro-2-methylsulfanylpyrimidin-4-yloxy)ethyl]piperidine-1-carboxylic acid tert-butyl ester as a white solid; $^1$H-NMR (CDCl$_3$), δ 1.07-1.17 (2H, m), 1.48 (9H, s), 1.62-1.70 (2H, m), 2.54 (3H, s), 2.64 (2H, br t), 4.06 (2H, m), 4.45 (2H, t), 4.64 (2H, d), 6.06 (1H, t), 7.30-7.34 (2H, m), 7.35-7.36 (3H, m).

Step 76.3: 4-[2-(5-Benzylcarbamoyl-6-chloro-2-cyanopyrimidin-4-yloxy)ethyl]-piperidine-1-carboxylic acid tert-butyl ester To a solution of 4-[2-(5-benzylcarbamoyl-6-chloro-2-methylsulfanylpyrimidin-4-yloxy)ethyl]piperidine-1-carboxylic acid tert-butyl ester (2.7 mmol) in CH2Cl2 (50 mL) is added m-CPBA (4.1 mmol) at 0° C. After stirring over night under N2 atmosphere, the reaction mixture is quenched by the addition of Na2S$_2$O3 and aq. sat. NaHCO3 at 0° C. The mixture is extracted twice with CH$_2$Cl$_2$, and the combined organic extracts are washed with aq. sat. NaHCO$_3$ and water. The organic layer is dried over Na$_2$SO$_4$, and concentrated to give 4-[2-(5-benzylcarbamoyl-6-chloro-2-methanesulfonylpyrimidin-4-yloxy)ethyl]piperidine-1-carboxylic acid tert-butyl ester as a white solid; $^1$H-NMR (CDCl$_3$), δ 1.08-1.18 (2H, m), 1.45 (9H, s), 1.63-1.75 (5H, m), 2.64 (2H, br t), 3.32 (3H, s), 4.05-4.08 (2H, m), 4.59 (2H, t), 4.66 (2H, d), 6.20 (1H, t), 7.31-7.37 (5H, m).

To a solution of the above product, 4-[2-(5-benzylcarbamoyl-6-chloro-2-methanesulfonylpyrimidin-4-yloxy)ethyl]piperidine-1-carboxylic acid tert-butyl ester in CH2Cl2/H2O (20 mL/2 mL) is added NaCN (3.3 mmol) and tetra-n-butylammonium bromide (0.14 mmol) at 0° C. After warmed up to room temperature, the reaction mixture is vigorously stirred for 1.5 h at room temperature. The mixture is diluted with CH2Cl2, washed with aq. NaHCO3. The organic layer is dried over Na2SO4, filtered, and concentrated. The residue is purified by silica gel column chromatography to give 4-[2-(5-benzylcarbamoyl-6-chloro-2-cyano-pyrimidin-4-yloxy)ethyl]piperidine-1-carboxylic acid tert-butyl ester as a white solid. $^1$H-NMR (CDCl$_3$), δ 1.09-1.19 (2H, m), 1.46 (9H, s), 1.63-1.74 (5H, m), 2.66 (2H, br t), 4.07 (2H, m), 4.51 (2H, t), 4.66 (2H, d), 6.11 (1H, t), 7.31-7.37 (5H, m).

Step 76.4: 4-(2-{5-Benzylcarbamoyl-2-cyano-6-[(spiro[2.5]oct-6-ylmethyl)amino]-pyrimidin-4-yloxy}ethyl)piperidine-1-carboxylic acid tert-butyl ester To a solution of 4-[2-(5-benzylcarbamoyl-6-chloro-2-cyanopyrimidin-4-yloxy)ethyl]piperidine-1-carboxylic acid tert-butyl ester (0.23 mmol) in CH$_3$CN (5 mL), C-spiro[2.5]oct-6-yl-methylamine hydrochloride (0.25 mmol) and K2CO3 (0.7 mmol) are added at room temperature. After warmed up to 70° C., the reaction mixture is stirred over night. The mixture is diluted with H2O and AcOEt, and extracted twice with AcOEt. The organic layer is dried over Na2SO4, filtered, and concentrated to give 4-(2-{5-benzylcarbamoyl-2-cyano-6-[(spiro[2.5]oct-6-ylmethyl)amino]pyrimidin-4-yloxy}ethyl)piperidine-1-carboxylic acid tert-butyl ester as a white solid; ¹H-NMR (CDCl₃), δ 0.17-0.30 (4H, m), 0.89-1.06 (4H, m), 1.14-1.38 (3H, m), 1.46 (9H, s), 1.49-1.79 (9H, m), 2.51 (2H, br t), 3.42 (2H, t), 4.00 (2H, m), 4.45 (2H, t), 4.55 (2H, d), 7.30-7.39 (5H, m), 8.12 (1H, t), 10.16 (1H, t).
Examples 77 to 164
By repeating the procedures described above using appropriate starting materials and conditions, the following compounds are obtained.
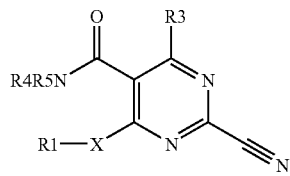
| Example | X—R1 | R3 | NR4R5 | MS (M⁺ + 1) | Rf value (solvent) |
|---------|------|-----|-------|-------------|--------------------|
| 77 | | | —NHMe | 441 | 0.50 (CH₂Cl₂:MeOH = 5:1) |
| 78 | | | | 531 | 0.51 (CH₂Cl₂:MeOH = 5:1) |
| 79 | | | | 557 | 0.35 (CH₂Cl₂:MeOH = 7:1) |
| 80 | | | | 535 | 0.24 (CH₂Cl₂:MeOH = 10:1) |
| 81 | | | | 523 | 0.34 (CH₂Cl₂:MeOH = 5:1) |

-continued

|  |  | R3 R4R5N — C(=O) — [pyrimidine] — CN, R1—X |  |  |  |
|---|---|---|---|---|---|
| Example | X—R1 | R3 | NR4R5 | MS (M⁺ + 1) | Rf value (solvent) |
| 82 | spiro[2.5] cyclohexyl-CH2-NH- | 1-methylpiperidin-4-yl-CH2CH2-O-CH3 | cyclopropyl-N(Me)H | 481 | 0.28 (CH$_2$Cl$_2$:MeOH = 5:1) |
| 83 | spiro[3.5] cyclohexyl-CH2-NH- | 1-methylpiperidin-4-yl-CH2CH2-O-CH3 | F$_3$C-CH2-N(Me)H | 523 | 0.40 (CH$_2$Cl$_2$:MeOH = 5:1) |
| 84 | spiro[3.5] cyclohexyl-CH2-NH- | 1-methylpiperidin-4-yl-CH2CH2-O-CH3 | cyclopropyl-CH2-N(Me)H | 495 | 0.40 (CH$_2$Cl$_2$:MeOH = 5:1) |
| 85 | spiro[3.5] cyclohexyl-CH2-NH- | 1-methylpiperidin-4-yl-CH2CH2-O-CH3 | pyrrolidin-1-yl | 495 | 0.55 (CH$_2$Cl$_2$:MeOH = 5:1) |
| 86 | spiro[3.5] cyclohexyl-CH2-NH- | 1-methylpiperidin-4-yl-CH2CH2-O-CH3 | neopentyl-N(Me)H | 525 | 0.61 (CH$_2$Cl$_2$:MeOH = 5:1) |
| 87 | spiro[3.5] cyclohexyl-CH2-NH- | 1-isopropylpiperidin-4-yl-CH2CH2-O-CH3 | —NHMe | 483 | 0.40 (CH$_2$Cl$_2$:MeOH = 5:1) |
| 88 | spiro[3.5] cyclohexyl-CH2-NH- | 1-isopropylpiperidin-4-yl-CH2-O-CH3 | —NHMe | 469 | 0.53 (CH$_2$Cl$_2$:MeOH = 8:1) |

-continued
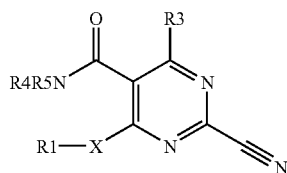
| Example | X—R1 | R3 | NR4R5 | MS (M⁺ + 1) | Rf value (solvent) |
|---|---|---|---|---|---|
| 89 | | | | 600 | 0.30 (CH$_2$Cl$_2$:MeOH = 5:1) |
| 90 | | | | 505 | 0.45 (n-hexane:AcOEt = 1:3) |
| 91 | | | | 532 | 0.29 (CH$_2$Cl$_2$:MeOH = 5:1) |
| 92 | | | | 517 | 0.22 (CH$_2$Cl$_2$:MeOH = 5:1) |
| 93 | | | | 531 | 0.39 (CH$_2$Cl$_2$:MeOH = 5:1) |

-continued
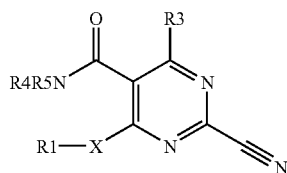
| Example | X—R1 | R3 | NR4R5 | MS (M⁺ + 1) | Rf value (solvent) |
|---|---|---|---|---|---|
| 94 | (spiro[2.5]octyl-CH2-NH-) | OMe | (3,3-difluoropyrrolidinyl-CH2-CH(NHMe)-CH2-Ph, (S)) | 539 | 0.72 (n-hexane:AcOEt = 1:1) |
| 95 | (4,4-dioxaspiro[2.5]-CH2-NH-) | (1-methylpiperidin-4-yl) | PhCH2CH2NHMe | 507 | 2.94 |
| 96 | (4,4-dioxaspiro[2.5]-CH2-NH-) | (piperidin-4-yl-CH2-OMe) | PhCH2NHMe | 493 | 2.78 |
| 97 | (spiro[3.5]nonyl-CH2-NH-) | (1-isopropylpiperidin-4-yl-CH2-OMe) | —NHMe | | |
| 98 | (spiro[3.5]nonyl-CH2-NH-) | (1-methylpiperidin-4-yl with CH2F, CH2OMe) | —NHMe | | |

-continued
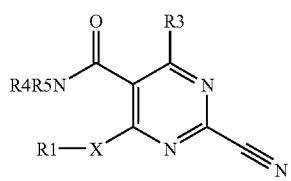
| Example | X—R1 | R3 | NR4R5 | MS (M⁺ + 1) | Rf value (solvent) |
|---|---|---|---|---|---|
| 99 | spiro[3.5]nonyl-CH2-NH- | 1-methylpiperidin-4-yl-CH2-O-CH3 | —NHMe | | |
| 100 | spiro[3.5]nonyl-CH2-NH- | 1-isopropylpiperidin-4-yl-CH2CH2-O-CH3 | —NHMe | | |
| 101 | spiro[3.5]nonyl-CH2-NH- | 1-(2-hydroxyethyl)piperidin-4-yl-CH2-O-CH3 | —NHMe | | |
| 102 | spiro[3.5]nonyl-CH2-NH- | 1-acetimidoylpiperidin-4-yl-CH2-O-CH3 | —NHMe | | |
| 103 | spiro[3.5]nonyl-CH2-NH- | 1-methylpiperidin-4-yl-CH2CH2-O-CH3 | —NHMe | | |

-continued
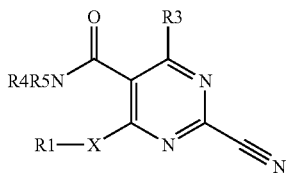
| Example | X—R1 | R3 | NR4R5 | MS (M⁺ + 1) | Rf value (solvent) |
|---|---|---|---|---|---|
| 104 | spiro[3.5]nonyl-CH2-NH- | 4-methylpiperazinyl-CH2CH2-O-Me | —NHMe | | |
| 105 | spiro[3.5]nonyl-CH2-NH- | piperidinyl-CH2-O-Me | —NHMe | | |
| 106 | spiro[3.5]nonyl-CH2-NH- | 2,2,6,6-tetramethylpiperidinyl-O- | —NHMe | | |
| 107 | spiro[3.5]nonyl-CH2-NH- | 1-isopropylpiperidin-4-yl-O- | —NHMe | | |
| 108 | spiro[3.5]nonyl-CH2-NH- | morpholinyl-CH2CH2CH2-O-Me | —NHMe | | |
| 109 | spiro[3.5]nonyl-CH2-NH- | MeNH-CH2CH2-NH-C(O)-Me | —NHMe | | |

-continued

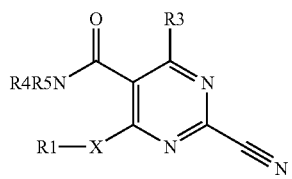

| Example | X—R1 | R3 | NR4R5 | MS (M+ + 1) | Rf value (solvent) |
|---|---|---|---|---|---|
| 110 | spiro[3.5]nonyl-CH2-NH- | 1-(2-methylaminoethyl)-2-imidazolidinone | —NHMe | | |
| 111 | spiro[3.5]nonyl-CH2-NH- | (S)-1-methylpyrrolidine-2-carboxamide | —NHMe | | |
| 112 | spiro[3.5]nonyl-CH2-NH- | —OMe | —NHMe | | |
| 113 | spiro[3.5]nonyl-CH2-NH- | 4-(2-methylaminoethyl)imidazole | —NHMe | | |
| 114 (i) | spiro[3.5]nonyl-CH2-NH- | 2-(2-hydroxyethoxy)methyl | —NHMe | 374 | |
| 115 | spiro[3.5]nonyl-CH2-NH- | 1-acetyl-4-(methoxymethyl)piperidine | —NHMe | | |
| 116 | spiro[3.5]nonyl-CH2-NH- | 1-(2-methoxyethyl)-2-pyrrolidinone | —NHMe | | |

-continued
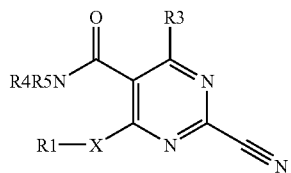
| Example | X—R1 | R3 | NR4R5 | MS (M⁺ + 1) | Rf value (solvent) |
|---|---|---|---|---|---|
| 117 | spiro[3.5]nonyl-CH2-NHMe | CH2-CH(OH)-CH2-NHMe | —NHMe | | |
| 118 | spiro[3.5]nonyl-CH2-NHMe | tBu-NH-CH2-CH2-O-Me | —NHMe | | |
| 119 | spiro[3.5]nonyl-CH2-NHMe | 2,6-dimethyl-4-methylpiperazinyl | —NHMe | | |
| 120 | spiro[3.5]nonyl-CH2-NHMe | 4-amino-cyclohexyl-CH2-O-Me | —NHMe | | |
| 121 | spiro[3.5]nonyl-CH2-NHMe | 1,3-dioxan-2-yl-CH2-O-Me | —NHMe | | |
| 122 | spiro[3.5]nonyl-CH2-NHMe | HO-C(Me)2-CH2-O-Me | —NHMe | | |

-continued

| Example | X—R1 | R3 | NR4R5 | MS (M⁺ + 1) | Rf value (solvent) |
|---|---|---|---|---|---|
| 123 | spiro[3.5]nonyl-CH2-NH(Me) | 1-amino-1-(methoxymethyl)cyclopentyl | —NHMe | | |
| 124 | spiro[3.5]nonyl-CH2-NH(Me) | cyclohexyl-NH-CH2CH2-OMe | —NHMe | | |
| 125 | spiro[3.5]nonyl-CH2-NH(Me) | 4-(2-methoxyethyl)piperazin-1-yl | —NHMe | | |
| 126 | spiro[3.5]nonyl-CH2-NH(Me) | MeNH-CH2-CH(Me)- | —NHMe | | |
| 127 | spiro[3.5]nonyl-CH2-NH(Me) | 4-(1-methylpiperidin-4-yl)-1-methylpiperazin-1-yl | —NHMe | | |
| 128 | spiro[3.5]nonyl-CH2-NH(Me) | (S)-tetrahydrofuran-2-yl-CH2-NHMe | —NHMe | | |

-continued

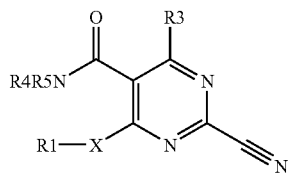

| Example | X—R1 | R3 | NR4R5 | MS (M⁺ + 1) | Rf value (solvent) |
|---|---|---|---|---|---|
| 129 | spiro[3.5]non-7-ylmethyl-NH-Me | 1-methyl-2-(methoxymethyl)imidazole | —NHMe | | |
| 130 | spiro[3.5]non-7-ylmethyl-NH-Me | 1-methylpiperidine-4-carboxamide | —NHMe | | |
| 131 | spiro[3.5]non-7-ylmethyl-NH-Me | morpholinyl methoxy ketone | —NHMe | | |
| 132 | spiro[3.5]non-7-ylmethyl-NH-Me | N,N-dimethylamino | —NHMe | | |
| 133 | spiro[3.5]non-7-ylmethyl-NH-Me | morpholine | —NHMe | | |
| 134 | spiro[3.5]non-7-ylmethyl-NH-Me | 2-amino-2-methyl-methoxymethyl | —NHMe | | |
| 135 | spiro[3.5]non-7-ylmethyl-NH-Me | N-methyl-N-(2-hydroxyethyl)amino | —NHMe | | |

-continued
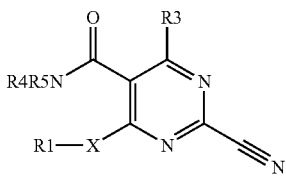
| Example | X—R1 | R3 | NR4R5 | MS (M⁺ + 1) | Rf value (solvent) |
|---|---|---|---|---|---|
| 136 | | | —NHMe | | |
| 137 | | | —NHMe | | |
| 138 | | | —NHMe | | |
| 139 | | | —NHMe | | |
| 140 | | | —NHMe | | |

-continued
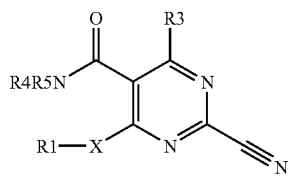
| Example | X—R1 | R3 | NR4R5 | MS (M⁺ + 1) | Rf value (solvent) |
|---|---|---|---|---|---|
| 141 | | | —NHMe | | |
| 142 | | | —NHMe | | |
| 143 | | | —NHMe | | |
| 144 | | | —NHMe | | |
| 145 | | | —NHMe | | |
| 146 | | | —NHMe | | |
| 147 | | | —NHMe | | |

US 7,704,996 B2

103                                                                                                                    104

-continued

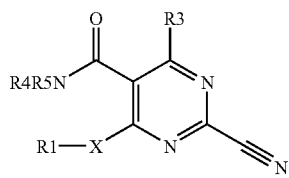

| Example | X—R1 | R3 | NR4R5 | MS (M⁺ + 1) | Rf value (solvent) |
|---|---|---|---|---|---|
| 148 | spiro[3.5]nonyl-CH2-NH- | trans-2-((methylamino)methyl)cyclohexan-1-ol | —NHMe | | |
| 149 | spiro[3.5]nonyl-CH2-NH- | 3-amino-1-methylpyrrolidinyl | —NHMe | | |
| 150 | spiro[3.5]nonyl-CH2-NH- | 3-acetamido-1-methylpyrrolidinyl | —NHMe | | |
| 151 | spiro[3.5]nonyl-CH2-NH- | ethyl 2-methoxyacetate | —NHMe | | |
| 152 | spiro[3.5]nonyl-CH2-NH- | cyclopropylmethyl(methyl)amine | —NHMe | | |
| 153 | spiro[3.5]nonyl-CH2-NH- | (1-methylpyrrolidin-2-yl)methanol | —NHMe | | |
| 154 | spiro[3.5]nonyl-CH2-NH- | 4-(2-(methylamino)ethyl)phenol | —NHMe | | |

-continued

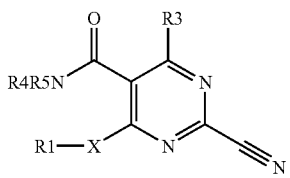

| Example | X—R1 | R3 | NR4R5 | MS (M⁺ + 1) | Rf value (solvent) |
|---|---|---|---|---|---|
| 155 | spiro[3.5]nonyl-CH2-NH- | MeO-CH2CH2-N(Me)-CH2CH2-OMe | —NHMe | | |
| 156 | spiro[3.5]nonyl-CH2-NH- | (S)-1-methyl-2-(methoxymethyl)pyrrolidinyl | —NHMe | | |
| 157 | spiro[3.5]nonyl-CH2-NH- | (R)-1-phenyl-ethyl-NH-CH2CH2-OMe | —NHMe | | |
| 158 | spiro[3.5]nonyl-CH2-NH- | 5-ethyl-2-(2-methoxyethyl)pyridyl | —NHMe | | |
| 159 | spiro[3.5]nonyl-CH2-NH- | tetrahydropyran-2-yl-O-CH2CH2-OMe | —NHMe | | |
| 160 | spiro[3.5]nonyl-CH2-NH- | (S)-1-methyl-pyrrolidine-2-carbaldehyde | —NHMe | | |
| 161 | spiro[3.5]nonyl-CH2-NH- | (S)-2-amino-3,3-dimethyl-1-methoxy-butyl | —NHMe | | |

-continued

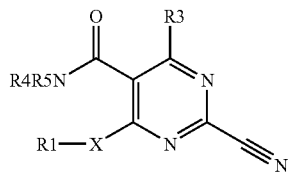

| Example | X—R1 | R3 | NR4R5 | MS (M⁺ + 1) | Rf value (solvent) |
|---|---|---|---|---|---|
| 162 | | | —NHMe | | |
| 163 | | | —NHMe | | |
| 164 | | | —NHMe | | |

HPLC conditions: Phenomenex Luna reverse phase C18 3 micron 30×4.6 mm column. Linear gradient from 90% water with 0.08% formic acid: 10% acetonitrile to 100% acetonitrile over 10 min. Detection at 254 nm.

(i) Compound of Example 114: Melting point=159° C.

Example 165

N-{2-Cyano-4-[2-(1-methylpiperidin-4-yl)ethoxy]-6-[(spiro[3.5]non-7-ylmethyl)amino]pyrimidin-5-yl}-C-phenylmethanesulfonamide Followed by the synthetic procedures for 4-[2-(1-methylpiperidin-4-yl)ethoxy]-6-[(spiro[3.5]non-7-ylmethyl)amino]pyrimidine-2-carbonitrile, 4-(2-{2-cyano-5-phenylmethanesulfonylamino-6-[(spiro[3.5]non-7-ylmethyl)amino]pyrimidin-4-yloxy}ethyl)piperidine-1-carboxylic acid tert-butyl ester is converted to N-{2-cyano-4-[2-(1-methylpiperidin-4-yl)ethoxy]-6-[(spiro[3.5]non-7-ylmethyl)amino]pyrimidin-5-yl}-C-phenylmethanesulfonamide.

Step 165.1: (4,6-Dichloro-2-methylsulfanylpyrimidin-5-yl)carbamic acid allyl ester To a solution of 4,6-dichloro-2-methylsulfanylpyrimidine-5-carboxylic acid (5.5 mmol) in dioxane (10 mL) are added diphenyl phosphoryl azide (6.6 mmol), triethylamine (6.6 mmol) and allyl alcohol (11 mmol) at room temperature under N₂ atmosphere. After stirring at 100° C. for 1 h, the reaction mixture is cooled to room temperature and diluted with AcOEt. The organic layer is washed twice with H₂O and evaporated in vacuo. The resulting residue is purified by silica gel column chromatography to give (4,6-dichloro-2-methylsulfanylpyrimidin-5-yl)carbamic acid allyl ester.

Step 165.2: 4-[2-(5-Allyloxycarbonylamino-6-chloro-2-methylsulfanylpyrimidin-4-yloxy)ethyl]piperidine-1-carboxylic acid tert-butyl ester Followed by the synthetic procedures as described in Reference Ex. 2, step 2.0, (4,6-di chloro-2-methylsulfanylpyrimidin-5-yl)carbamic acid allyl ester is converted to 4-[2-(5-allyloxycarbonylamino-6-chloro-2-methylsulfanylpyrimidin-4-yloxy)ethyl]piperidine-1-carboxylic acid tert-butyl ester.

Step 165.3: 4-[2-(5-Allyloxycarbonylamino-6-chloro-2-cyano-pyrimidin-4-yloxy)ethyl]piperidine-1-carboxylic acid tert-butyl ester Followed by the synthetic procedures as described in Reference Example 2 for 4-[2-(6-chloro-2-cyanopyrimidin-4-yloxy)ethyl]piperidine-1-carboxylic acid tert-butyl ester, 4-[2-(5-allyloxycarbonyl amino-6-chloro-2-methylsulfanylpyrimidin-4-yloxy)ethyl]piperidine-1-carboxylic acid tert-butyl ester is converted to 4-[2-(5-Allyloxycarbonylamino-6-chloro-2-cyano-pyrimidin-4-yloxy)ethyl]piperidine-1-carboxylic acid tert-butyl ester.

Step 165.4: 4-(2-{5-Allyloxycarbonylamino-2-cyano-6-[(spiro[3.5]non-7-ylmethyl)-amino]pyrimidin-4-yloxy}ethyl)piperidine-1-carboxylic acid tert-butyl ester Followed by the synthetic procedures as described in Reference Example 2, step 2.2, for 4-(2-[2-cyano-6-[(spiro[3.5]non-7-ylmethyl)-amino]pyrimidin-4-yloxy]ethyl)piperidine-1-carboxylic acid tert-butyl ester, 4-[2-(5-Allyloxycarbonylamino-6-chloro-2-cyano-pyrimidin-4-yloxy)ethyl]piperidine-1-carboxylic acid tert-butyl ester is converted to 4-(2-{5-allyloxy carbonylamino-2-cyano-6-[(spiro[3.5]non-7-ylmethyl)amino]pyrimidin-4-yloxy}ethyl)piperidine-1-carboxylic acid tert-butyl ester.

Step 165.5: 4-(2-{5-Amino-2-cyano-6-[(spiro[3.5]non-7-ylmethyl)amino]pyrimidin-4-yloxy}ethyl)piperidine-1-carboxylic acid tert-butyl ester To a solution of the crude 4-(2-{5-allyloxycarbonylamino-2-cyano-6-[(spiro[3.5]non-7-ylmethyl)amino]pyrimidin-4-yloxy}ethyl)piperidine-1-carboxylic acid tert-butyl ester (230 mg) in THF (10 mL) are added triethylamine (1.25 mmol) and Pd(PPh$_3$)$_4$ (catalytic amount) at room temperature under N$_2$ atmosphere. After stirring at the same temperature for 1 h, the reaction mixture is diluted with AcOEt. The organic layer is washed with H$_2$O and evaporated in vacuo. The resulting residue is purified by silica gel column chromatography to give 4-(2-{5-Amino-2-cyano-6-[(spiro[3.5]non-7-ylmethyl)amino]pyrimidin-4-yloxy}ethyl)piperidine-1-carboxylic acid tert-butyl ester; $^1$H-NMR (CDCl$_3$), δ: 0.97-1.07 (2H, m), 1.13-1.28 (4H, m), 1.42-1.88 (25H, m), 2.69 (2H, t), 3.22 (2H, s), 3.31 (2H, t), 4.04-4.16 (2H, m), 4.40 (2H, t), 4.51 (1H, t).

Step 165.6: 4-(2-{2-Cyano-5-phenylmethanesulfonylamino-6-[(spiro[3.5]non-7-ylmethyl)amino]pyrimidin-4-yloxy}ethyl)piperidine-1-carboxylic acid tert-butyl ester Benzylsulfonylchloride (0.50 mmol) is added to a solution of 4-(2-{5-amino-2-cyano-6-[(spiro[3.5]non-7-ylmethyl)amino]pyrimidin-4-yloxy}ethyl)piperidine-1-carboxylic acid t-butyl ester (167 mg) and pyridine (0.66 mmol) in CH$_2$Cl$_2$ (3 mL) are added at 0° C. After stirring at room temperature for 1 h, benzylsulfonylchloride (0.50 mmol), pyridine (0.66 mmol) and DMAP (catalytic amount) are added to the reaction mixture again. The reaction mixture is stirred at room temperature for 1 h and diluted with AcOEt. The organic layer is washed with H$_2$O and evaporated in vacuo. The resulting residue is purified by silica gel column chromatography to give 4-(2-{2-cyano-5-phenylmethanesulfonylamino-6-[(spiro[3.5]non-7-ylmethyl)amino]pyrimidin-4-yloxy}ethyl)piperidine-1-carboxylic acid tert-butyl ester.

Examples 166 and 167

By repeating the procedures described above using appropriate starting materials and conditions, the following compounds are obtained.

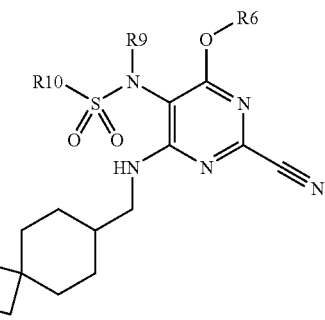

| Example | R6 | R10 | R9 | MS (M$^+$ + 1) | Rf value (solvent) |
|---|---|---|---|---|---|
| 166 | 4-propyl-1-isopropylpiperidine | Me | i-Pr | 561 | 0.40 (CH$_2$Cl$_2$:MeOH = 5:1) |
| 167 | 4-propyl-1-methylpiperidine | —(CH$_2$)$_3$— | | 517 | 0.50 (CH$_2$Cl$_2$:MeOH = 5:1) |

Example 168-173

By repeating the procedures described above using appropriate starting materials and conditions, the following compounds can be obtained.

| Example | R2 | X | —O—R6 |
|---|---|---|---|
| 168 (ii) | spiro[3.5]nonyl-methyl | iso-propyl | NH | 1-methylpiperidin-4-yloxy |
| 169 | spiro[3.5]nonyl-methyl | methyl | NH | 2-methoxyethoxy |
| 170 | spiro[3.5]nonyl-methyl | —C(O)N(Me)H | NMe | 2-methoxyethoxy |
| 171 | spiro[3.5]nonyl-methyl | —C(O)NMe₂ | NH | 2-methoxyethoxy |
| 172 | spiro[3.5]nonyl-methyl | —C(O)NMe₂ | NMe | 2-methoxyethoxy |
| 173 | spiro[2.5]octyl-methyl | —C(O)N(Me)H | NH | 2-methoxyethoxy |

Me=methyl (ii) Compound of Example 168: Melting point=131° C.; (M+H)⁺=412.

Example 174

Soft Capsules 5000 soft gelatin capsules, each comprising as active ingredient 0.05 g of one of the compounds of formula I mentioned in the preceding Examples, are prepared as follows:

Composition

| | |
|---|---|
| Active ingredient | 250 g |
| Lauroglycol | 2 litres |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:

1. A 2-cyanopyrimidine of the formula

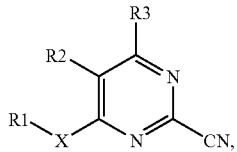

(I)

wherein $R_1$ denotes a radical of the formula

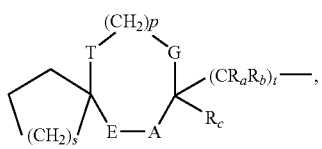

(Ia)

wherein A, E and G independently of each other represent O, S or $CH_2$, under the proviso that at least one of A and E represents $CH_2$;

T is O, S or a bond, if G is $CH_2$, and T is a bond, if G is O or S;

Ra, Rb and Rc independently of each other represent hydrogen or $C_1$-$C_4$alkyl;

s is 0, 1 or 2, t is 1, 2, 3, or 4 and p is 0, 1 or 2;

$R_2$ denotes halogen, $C_1$-$C_4$alkyl, unsubstituted or substituted aryl, 5 or 6 membered heterocyclyl, —C(O)NR_4R_5, —NHC(O)R_4 or —CH_2NHC(O)R_4, wherein $R_4$ represents (a) $C_1$-$C_7$alkyl which is unsubstituted or substituted by halogen; amino, which is mono- or disubstituted by $C_3$-$C_5$cycloalkyl or $C_1$-$C_6$alkyl which in each case are unsubstituted or mono-, di- or trisubstituted by halogen; unsubstituted or substituted $C_4$-$C_8$-aliphatic heterocyclyl comprising at least one nitrogen atom; unsubstituted or substituted phenyl; unsubstituted or substituted hetaryl; unsubstituted or substituted spiro[4.5]decane which contains 1 or 2 heteroatoms selected from oxygen, nitrogen and sulfur; unsubstituted or substituted $C_3$-$C_6$cycloalkyl; or 1-aza-($C_5$-$C_8$)bicycloalkyl;

(b) unsubstituted or substituted N—($C_1$-$C_4$alkyl) piperidinyl or N—($C_4$-$C_6$cycloalkyl) piperidinyl;

(c) unsubstituted or substituted aryl;

(d) unsubstituted or substituted $C_3$-$C_6$cycloalkyl; or (e) unsubstituted or substituted 5 or 6 membered hetaryl containing one nitrogen atom; and $R_5$ represents hydrogen or $C_1$-$C_4$alkyl; or $R_4$ and $R_5$ together with the nitrogen to which they are attached represent unsubstituted or substituted $C_4$-$C_8$-aliphatic heterocyclyl comprising at least one nitrogen atom; or $R_2$ denotes —N($R_9$)SO$_2$R$_{10}$, $R_9$ represents hydrogen or $C_1$-$C_4$alkyl; and $R_{10}$ represents $C_1$-$C_4$alkyl, which is unsubstituted or substituted by aryl; or $R_9$ and $R_{10}$ together form a radical —(CRR')$_m$—, wherein m is an integer from and including 2 up to and including 5 and R and R' both represent independently of each other hydrogen or $C_1$-$C_4$alkyl;

$R_3$ denotes hydrogen, halogen, phenyl, pyridyl, which is unsubstituted or mono-, di- or trisubstituted by halogen, Y—$R_6$ or NR$_7$R$_8$ wherein Y represents O, $CH_2$, S, SO, $SO_2$ or NR$_N$, wherein $R_N$ denotes hydrogen or $C_1$-$C_4$alkyl which is unsubstituted or substituted by $C_1$-$C_4$alkoxy;

$R_6$ represents $C_1$-$C_6$alkyl, aryl, five or six-membered nitrogen containing hetaryl-(CH$_2$)$_q$—, wherein q is an integer from 0 to 4, or five or six-membered aliphatic heterocyclyl -(CH$_2$)$_n$—, wherein n is an integer from 0 to 4 and the heterocyclyl moiety contains at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety contains at least one nitrogen atom;

X denotes O, HN, $C_1$-$C_4$alkyl—N, S, SO, SO$_2$, O(CH$_2$)$_g$NH, wherein g is 1 or 2, (CH$_2$)$_h$, wherein h is 1 or 2, or phenyl, which is unsubstituted or mono-, di- or trisubstituted by halogen, $C_1$-$C_4$alkyl or $C_1$-$C_4$alkoxy;

or a tautomer and/or salt of such 2-cyano-pyrimidine.

2. A 2-cyano-pyrimidine according to claim 1 of the formula I, wherein $R_1$ denotes a radical of formula

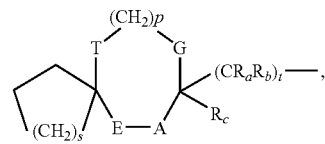

(Ia)

wherein A, E and G independently of each other represent O, S or $CH_2$, under the proviso that at least one of A and E represents $CH_2$;

T is O, S or a bond, if G is $CH_2$, and T is a bond, if G is O or S;

Ra, Rb and Rc independently of each other represent hydrogen or $C_1$-$C_4$alkyl;

s is 0 or 2, t is 1, 2, 3 or 4 and p is 0, 1 or 2;

$R_2$ denotes halogen, $C_1$-$C_4$ alkyl, unsubstituted or substituted phenyl, 5 or 6 membered heterocyclyl, —C(O)NR$_4$R$_5$, —NHC(O)R$_4$, —CH$_2$NHC(O)R$_4$ or —N(R$_9$)SO$_2$R$_{10}$, wherein $R_4$ represents (a) $C_1$-$C_7$alkyl which is unsubstituted or substituted by
amino, which is mono- or disubstituted by $C_3$-$C_5$cycloalkyl or $C_1$-$C_6$alkyl which is unsubstituted or trisubstituted by halogen;
aza-($C_4$-$C_8$)cycloalkyl, which is unsubstituted or substituted by halogen, $C_1$-$C_4$alkoxy, $C_1$-$C_4$alkoxy $C_1$-$C_4$alkyl, $C_1$-$C_4$alkyl amino, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;
piperazinyl, which is mono- or disubstituted by $C_1$-$C_4$alkyl or phenyl; or phenyl, which is unsubstituted or mono- or disubstituted by halogen, morpholinyl, trifluoromethyl or $C_1$-$C_4$alkoxy;

halogen, $C_3$-$C_5$cycloalkyl, morpholinyl, thienyl, furyl, pyridyl, 2-oxa-6-aza-spiro[4.5]decane or 1-aza-($C_5$-$C_7$)bicycloalkyl;

(b) N—($C_1$-$C_4$alkyl) piperidinyl, which is substituted by phenyl;

(c) phenyl, which is mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl) piperazinyl, N—($C_1$-$C_4$alkyl) piperidinyloxy or N—($C_1$-$C_4$alkyl) piperidinyl $C_1$-$C_4$alkoxy;

(d) $C_3$-$C_5$cycloalkyl;

(e) isoxazolyl, imidazolyl or pyrazolyl, which in each case is mono- or disubstituted by pyridyl or phenyl; or (f) N—($C_1$-$C_6$alkyl) piperidinyl or N—($C_4$-$C_6$cycloalkyl) piperidinyl which in both cases is substituted by phenyl $C_1$-$C_4$alkyl, wherein phenyl is unsubstituted or mono-substituted by halogen; and $R_5$ represents hydrogen or $C_1$-$C_4$alkyl; or $R_4$ and $R_5$ together with the nitrogen to which they are attached represent pyrrolidinyl or piperidinyl which is unsubstituted or substituted by hydroxy;

$R_9$ represents hydrogen or $C_1$-$C_4$alkyl; and $R_{10}$ represents $C_1$-$C_4$alkyl, which is unsubstituted or substituted by phenyl; or $R_9$ and $R_{10}$ together form a radical —(CRR')$_m$—, wherein m is an integer from and including 2 up to and including 4 and R and R' both represent hydrogen;

$R_3$ denotes hydrogen, halogen, phenyl, pyridyl, which is unsubstituted or monosubstituted by halogen or piperazinyl, Y—$R_6$ or NR$_7$R$_8$ wherein Y represents O, $CH_2$, S, SO, $SO_2$ or NR$_N$, wherein R$_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl—(CH$_2$)$_q$—, wherein q is an integer from 0 to 4, or five or six-membered aliphatic heterocyclyl—(CH$_2$)$_n$—, wherein n is an integer from $_0$ to $_4$ and the heterocyclyl moiety contains at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety contains at least one nitrogen atom;

X denotes O, HN, $C_1$-$C_4$alkyl—N, S, SO, $SO_2$, $OCH_2CH_2NH$, $CH_2$ or phenyl, which is unsubstituted or monosubustituted by halogen;

or a tautomer and/or salt of such 2-cyano-pyrimidine.

3. A 2-cyano-pyrimidine according to claim 1 of the formula I, wherein $R_1$ denotes a radical of formula

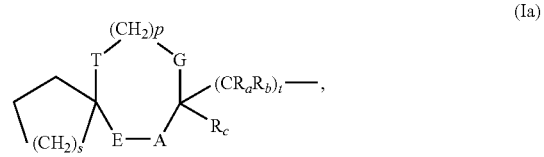

wherein A, E and G independently of each other represent O, S or $CH_2$, under the proviso that at least one of A and E represents $CH_2$;

T is O, S or a bond, if G is $CH_2$, and T is a bond, if G is O or S;

Ra, Rb and Rc independently of each other represent hydrogen or $C_1$-$C_4$alkyl;

s is 0 or 1, t is 1, 2, 3 or 4 and p is 0, 1 or 2;

$R_2$ denotes bromo, chloro, $C_1$-$C_4$ alkyl, unsubstituted phenyl or a 6 membered heterocyclyl group containing at least one oxygen atom, —C(O)—NR$_4$R$_5$ or —N(R$_9$)—$SO_2$—R$_{10}$, wherein $R_4$ represents (a) $C_1$-$C_7$alkyl which is unsubstituted or substituted by amino, which is mono- or disubstituted by $C_3$-$C_5$cycloalkyl or $C_1$-$C_6$alkyl which is unsubstituted or trisubstituted by halogen;

aza-($C_4$-$C_8$)cycloalkyl, which is unsubstituted or substituted by halogen, $C_1$-$C_4$alkoxy, $C_1$-$C_4$alkoxy $C_1$-$C_4$alkyl, $C_1$-$C_4$alkyl amino, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;

piperazinyl, which is mono- or disubstituted by $C_1$-$C_4$alkyl or phenyl; or phenyl, which is unsubstituted or mono- or disubstituted by halogen, morpholinyl, trifluoromethyl or $C_1$-$C_4$alkoxy;

halogen, $C_3$-$C_5$cycloalkyl, morpholinyl, thienyl, furyl, pyridyl, 2-oxa-6-aza-spiro [4.5] decane or 1-aza-($C_5$-$C_7$)bicycloalkyl;

(b) N—($C_1$-$C_4$alkyl) piperidinyl, which is substituted by phenyl;

(c) phenyl, which is mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl) piperazinyl, N—($C_1$-$C_4$alkyl) piperidinyloxy or N—($C_1$-$C_4$alkyl) piperidinyl $C_1$-$C_4$alkoxy;

(d) $C_3$-$C_5$cycloalkyl;

(e) pyrazolyl, which is mono- or disubstituted by pyridyl or phenyl; or (f) N—($C_1$-$C_6$alkyl) piperidinyl or N—($C_4$-$C_6$cycloalkyl) piperidinyl which in both cases is substituted by phenyl $C_1$-$C_4$alkyl, wherein phenyl is unsubstituted or mono-substituted by halogen; and $R_5$ represents hydrogen or $C_1$-$C_4$alkyl; or $R_4$ and $R_5$ together with the nitrogen to which they are attached represent pyrrolidinyl;

$R_9$ represents hydrogen or $C_1$-$C_4$alkyl; and $R_{10}$ represents $C_1$-$C_4$alkyl, which is unsubstituted or substituted by phenyl; or $R_9$ and $R_{10}$ together form a radical $-(CRR')_m-$, wherein m is an integer from and including 2 up to and including 4 and R and R' both represent hydrogen;

$R_3$ denotes hydrogen, $Y-R_6$ or $NR_7R_8$ wherein

Y represents O or $NR_N$, wherein $R_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl—$(CH_2)_q$—, wherein q is an integer from 0 to 4, or five or six-membered aliphatic heterocyclyl -$(CH_2)_n$—, wherein n is an integer from 0 to 4 and the heterocyclyl moiety contains at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety contains at least one nitrogen atom;

X denotes HN, $C_1$-$C_4$alkyl-N or O;

or a tautomer and/or salt of such 2-cyano-pyrimidine.

4. A 2-cyano-pyrimidine according to claim 1 of the formula I, wherein $R_1$ denotes a radical of formula

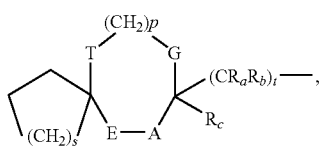

(Ia)

wherein A, E and G independently of each other represent O or $CH_2$, under the proviso that at least one of A and E represents $CH_2$;

T is O or a bond, if G is $CH_2$, and T is a bond, if G is O;

Ra, Rb and Rc all represent hydrogen;

s is 0 or 1, t is 1, or 2 and p is 1;

$R_2$ denotes bromo, chloro, isopropyl, unsubstituted phenyl or a 6 membered heterocyclyl group containing two oxygen atoms, $-C(O)-NR_4R_5$ or $-N(R_9)-SO_2-R_{10}$, wherein $R_4$ represents (a) $C_1$-$C_7$alkyl which is unsubstituted or substituted by amino, which is mono- or disubstituted by $C_3$-$C_5$cycloalkyl or $C_1$-$C_6$alkyl which is unsubstituted or trisubstituted by halogen;

1-aza-($C_7$-$C_8$)cycloalkyl, which is unsubstituted or substituted by $C_1$-$C_4$alkyl;

1-aza-($C_4$cycloalkyl, which is unsubstituted or substituted by $C_1$-$C_4$alkyl;

pyrrolidinyl, which is unsubstituted or substituted by halogen, $C_1$-$C_4$alkoxy, $C_1$-$C_4$alkoxy $C_1$-$C_4$alkyl or $C_1$-$C_4$alkyl amino;

piperidinyl, which is unsubstituted or mono- or disubstituted by halogen, pyrrolidinyl, piperidinyl, di(halo)-piperidinyl, ($C_4$-$C_6$)cycloalkyl or $C_1$-$C_6$alkyl which is unsubstituted or mono- or disubstituted by hydroxy or halogen;

piperazinyl, which is mono- or disubstituted by $C_1$-$C_4$alkyl or phenyl; or phenyl, which is unsubstituted or mono- or disubstituted by halogen, morpholinyl, trifluoromethyl or $C_1$-$C_4$alkoxy;

halogen, $C_3$-$C_5$cycloalkyl, morpholinyl, thienyl, furyl, pyridyl, 2-oxa-6-aza-spiro[4.5]decane or 1-aza-($C_5$-$C_7$)bicycloalkyl;

(b) N—($C_1$-$C_4$alkyl) piperidinyl, which is substituted by phenyl;

(c) phenyl, which is mono-, di- or trisubstituted by phenyl, $C_3$-$C_5$cycloalkyloxy, $C_1$-$C_4$alkoxy, $C_1$-$C_4$alkoxy $C_1$-$C_4$alkoxy, $C_1$-$C_4$alkoxy phenyl, di($C_1$-$C_4$alkyl)-amino $C_1$-$C_4$alkoxy, N—($C_1$-$C_4$alkyl) piperazinyl, N—($C_1$-$C_4$alkyl) piperidinyloxy or N—($C_1$-$C_4$alkyl) piperidinyl $C_1$-$C_4$alkoxy;

(d) $C_3$-$C_5$cycloalkyl;

(e) pyrazolyl, which is mono- or disubstituted by pyridyl or phenyl; or (f) N—($C_1$-$C_6$alkyl) piperidinyl or N—($C_4$-$C_6$cycloalkyl) piperidinyl which in both cases is substituted by phenyl $C_1$-$C_4$alkyl, wherein phenyl is unsubstituted or mono-substituted by halogen; and $R_5$ represents hydrogen or $C_1$-$C_4$alkyl; or $R_4$ and $R_5$ together with the nitrogen to which they are attached represent pyrrolidinyl;

$R_9$ represents hydrogen or $C_1$-$C_4$alkyl; and $R_{10}$ represents $C_1$-$C_4$alkyl, which is unsubstituted or substituted by phenyl; or $R_9$ and $R_{10}$ together form a radical $-(CRR')_m-$, wherein m is an integer from and including 2 up to and including 4 and R and R' both represent hydrogen;

$R_3$ denotes hydrogen, $Y-R_6$ or $NR_7R_8$ wherein

Y represents O or $NR_N$, wherein $R_N$ denotes hydrogen or $C_1$-$C_4$alkyl which is unsubstituted or substituted by $C_1$-$C_4$alkoxy;

$R_6$ represents $C_1$-$C_6$alkyl, phenyl, five or six-membered nitrogen containing hetaryl-$(CH_2)_q$—, wherein q is an integer from 0 to 4, or five or six-membered aliphatic heterocyclyl-$(CH_2)_n$—, wherein n is an integer from 0 to 4 and the heterocyclyl moiety contains at least one ring nitrogen atom, which radicals in each case can be unsubstituted or substituted;

$R_7$ and $R_8$ together with the nitrogen to which they are attached represent unsubstituted or substituted five or six-membered aliphatic heterocyclyl, wherein the heterocyclyl moiety contains at least one nitrogen atom;

X denotes HN, $C_1$-$C_4$alkyl—N or O;

or a tautomer and/or salt of such 2-cyano-pyrimidine.

5. A method for the treatment of neuropathic pain, which comprises administering a 2-cyano-pyrimidine according to claim 1 of the formula I or a tautomer thereof, or a pharmaceutically acceptable salt of such a compound or tautomer, in a quantity effective against said disease, to a warm-blooded animal requiring such treatment.

6. A pharmaceutical preparation, comprising a 2-cyano-pyrimidine according to claim 1 of the formula I or a tautomer thereof, or a pharmaceutically acceptable salt of such a compound or tautomer and at least one pharmaceutically acceptable carrier.

7. A process for the preparation of a 2-cyano-pyrimidine of the formula

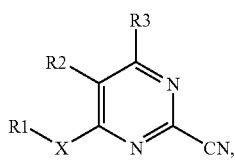
(I)

wherein
$R_1$ denotes a radical of formula

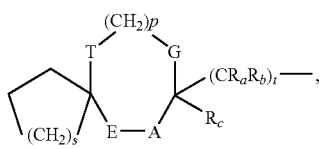
(Ia)

wherein A, E and G independently of each other represent O, S or $CH_2$, under the proviso that at least one of A and E represents $CH_2$;
  T is O, S or a bond, if G is $CH_2$, and T is a bond, if G is O or S;
  Ra, Rb and Rc independently of each other represent hydrogen or $C_1$-$C_4$alkyl;
  s is 0, 1 or 2, t is 1, 2, 3 or 4 and p is 0, 1 or 2;
$R_2$ denotes halogen, $C_1$-$C_4$ alkyl, unsubstituted or substituted aryl, 5 or 6 membered heterocyclyl, —C(O)$NR_4R_5$, —NHC(O)$R_4$ or —$CH_2$NHC(O)$R_4$, wherein $R_4$ represents
  (a) $C_1$-$C_7$alkyl which is unsubstituted or substituted by halogen; amino, which is mono- or disubstituted by $C_3$-$C_5$cycloalkyl or $C_1$-$C_6$alkyl which in each case are unsubstituted or mono-, di- or trisubstituted by halogen; unsubstituted or substituted $C_4$-$C_8$-aliphatic heterocyclyl comprising at least one nitrogen atom; unsubstituted or substituted phenyl; unsubstituted or substituted hetaryl; unsubstituted or substituted spiro[4.5]decane which comprises 1 or 2 heteroatoms selected from oxygen, nitrogen and sulfur; unsubstituted or substituted $C_3$-$C_6$cycloalkyl; or 1-aza-($C_5$-$C_8$)bicycloalkyl;
  (b) unsubstituted or substituted N—($C_1$-$C_4$alkyl) piperidinyl or N—($C_4$-$C_6$cycloalkyl) piperidinyl;
  (c) unsubstituted or substituted aryl;
  (d) unsubstituted or substituted $C_3$-$C_6$cycloalkyl; or
  (e) unsubstituted or substituted 5 or 6 membered hetaryl containing one nitrogen atom; and
$R_5$ represents hydrogen or $C_1$-$C_4$alkyl; or
$R_4$ and $R_5$ together with the nitrogen to which they are attached represent unsubstituted or substituted $C_4$-$C_8$-aliphatic heterocyclyl comprising at least one nitrogen atom; or
$R_2$ denotes —N($R_9$)$SO_2R_{10}$,
$R_9$ represents hydrogen or $C_1$-$C_4$alkyl; and
$R_{10}$ represents $C_1$-$C_4$alkyl, which is unsubstituted or substituted by aryl; or
$R_9$ and $R_{10}$ together form a radical —(CRR')$_m$—, wherein m is an integer from and including 2 up to and including 5 and R and R' both represent independently of each other hydrogen or $C_1$-$C_4$alkyl;
$R_3$ denotes hydrogen, halogen, phenyl, pyridyl, which is unsubstituted or mono-, di- or trisubstituted by halogen, Y—$R_6$ or $NR_7R_8$ wherein Y represents O, $CH_2$, S, SO, $SO_2$ or $NR_N$, wherein $R_N$ denotes hydrogen or $C_1$-$C_4$alkyl which is unsubstituted or substituted by $C_1$-$C_4$alkoxy;
$R_6$ represents $C_1$-$C_6$alkyl, aryl, five or six-membered nitrogen containing hetaryl—($CH_2$)$_q$—, wherein q is an integer from 0 to 4, or five or six-membered aliphatic heterocyclyl ($CH_2$)$_n$—, wherein n is an integer from 0 to 4 and the heterocyclyl moiety comprises at least one ring nitrogen atom, which radicals in each case can be unsubstituted or substituted;
$R_7$ and $R_8$ together with the nitrogen to which they are attached represent unsubstituted or substituted five or six-membered aliphatic heterocyclyl, wherein the heterocyclyl moiety comprises at least one nitrogen atom;
X denotes O, HN, $C_1$-$C_4$alkyl—N, S, SO, $SO_2$, O($CH_2$)$_g$NH, wherein g is 1 or 2, ($CH_2$)$_h$, wherein h is 1 or 2, or phenyl, which is unsubstituted or mono-, di- or trisubstituted by halogen, $C_1$-$C_4$alkyl or $C_1$-$C_4$alkoxy;
the process comprising:
a) for the synthesis of a compound of the formula I wherein $R_2$ represents —C(O)$NR_4R_5$, $R_3$denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl—N, O($CH_2$)$_g$NH, O or S and the remaining radicals and symbols $R_1$, $R_4$, $R_5$, $R_6$, $R_7$, $R_8$ and g are as defined in claim 1 for a compound of the formula I,
reacting the 5-pyrimidyl carboxylic acid of formula II

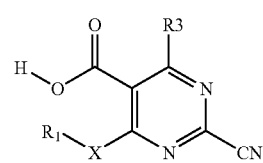
(II)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl—N, O($CH_2$)$_g$NH, O or S, and the remaining radicals and symbols $R_1$, $R_6$, $R_7$, $R_8$ and g are as defined in claim 1 for a compound of the formula I,
with an amine of formula III

(III)

wherein the symbols $R_4$ and $R_5$ are as defined for a compound of the formula I;
b) for the synthesis of a compound of the formula I wherein $R_2$ represents C(O)$NR_4R_5$, $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl—N, O($CH_2$)$_g$NH, O or S and the remaining radicals and symbols $R_1$, $R_4$, $R_5$, $R_6$, $R_7$, $R_8$ and g are as defined in claim 1 for a compound of the formula I, reacting the 6-chloro pyrimidine derivative of formula IV

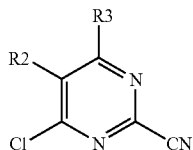

(IV)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, and the remaining radicals $R_2$, $R_6$, $R_7$ and $R_8$ are as defined in claim 1 for a compound of the formula I, with a compound of formula V $R_1$—X—H   (V)

wherein X denotes HN, $C_1$-$C_4$alkyl—N, $O(CH_2)_g$NH, O or S and $R_1$ has the meaning as defined in claim 1 for a compound of the formula I;

c) for the synthesis of a compound of the formula I wherein $R_2$ denotes —$N(R_9)SO_2R_{10}$, $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl—N, $O(CH_2)_g$NH, O or S and the remaining radicals and symbols $R_1$, $R_6$, $R_7$, $R_8$, $R_9$, $R_{10}$ and g are as defined for a compound of the formula I, reacting the 5-amino pyrimidine of formula VI

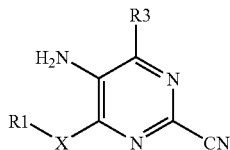

(VI)

wherein $R_3$ denotes hydrogen, halogen, phenyl, pyridyl, which is unsubstituted or mono-, di- or trisubstituted by halogen, Y—$R_6$, wherein Y represents O, NH or S, or $NR_7R_8$, X denotes HN, $C_1$-$C_4$alkyl—N, $O(CH_2)_g$NH, O or S and the remaining radicals and symbols $R_1$, $R_6$, $R_7$, $R_8$ and g are as defined for a compound of the formula I, with a sulfonyl halide of formula VII

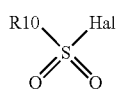

(VII)

wherein the radical $R_{10}$ is as defined for a compound of the formula I and Hal denotes halide, optionally followed by replacing the hydrogen atom in the sulfonamide function of the obtained compound of formula I by the group $R_9$ by means of an alkylation reaction;

wherein in all cases the staffing materials of formula II to VII may also be present with functional groups in protected form, if necessary, and/or in the form of salts, provided a salt-forming group is present and the reaction in salt form is possible;

wherein any protecting groups in a protected derivative of a compound of the formula I are subsequently removed; and, if so desired, an obtainable compound of formula I is converted into another compound of formula I, a free compound of formula I is converted into a salt, and/or an obtainable salt of a compound of formula I is converted into the free compound or another salt.

* * * * *